United States Patent
Cataldo et al.

(10) Patent No.: US 10,675,588 B2
(45) Date of Patent: Jun. 9, 2020

(54) METHOD OF PURIFYING A BIOLOGICAL MATERIAL OF INTEREST IN A SAMPLE USING NANOFIBER ULTRAFILTRATION MEMBRANES OPERATED IN TANGENTIAL FLOW FILTRATION MODE

(71) Applicant: EMD Millipore Corporation, Burlington, MA (US)

(72) Inventors: William Cataldo, Bradford, MA (US); Mikahil Kozlov, Lexington, MA (US); Alex Xenopoulos, Cambridge, MA (US); Dennis Aquino, Chelmsford, MA (US); Clifton Ngan, Chelmsford, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 15/561,579

(22) PCT Filed: Feb. 17, 2016

(86) PCT No.: PCT/US2016/018146
§ 371 (c)(1),
(2) Date: Sep. 26, 2017

(87) PCT Pub. No.: WO2016/167871
PCT Pub. Date: Oct. 20, 2016

(65) Prior Publication Data
US 2018/0085710 A1    Mar. 29, 2018

Related U.S. Application Data

(60) Provisional application No. 62/148,793, filed on Apr. 17, 2015.

(51) Int. Cl.
| | | |
|---|---|---|
| *B01D 61/00* | (2006.01) | |
| *B01D 71/60* | (2006.01) | |
| *B01D 61/14* | (2006.01) | |
| *B01D 39/16* | (2006.01) | |
| *B01D 67/00* | (2006.01) | |
| *B01D 71/54* | (2006.01) | |
| *C07K 1/34* | (2006.01) | |
| *B01D 71/56* | (2006.01) | |

(52) U.S. Cl.
CPC ....... *B01D 61/145* (2013.01); *B01D 39/1623* (2013.01); *B01D 67/0004* (2013.01); *B01D 71/54* (2013.01); *B01D 71/56* (2013.01); *C07K 1/34* (2013.01); *B01D 2239/025* (2013.01); *B01D 2315/16* (2013.01); *B01D 2323/39* (2013.01)

(58) Field of Classification Search
None
See application file for complete search history.

(56) References Cited

U.S. PATENT DOCUMENTS

| | | |
|---|---|---|
| 552,291 A | 12/1895 | Keefer |
| 692,631 A | 2/1902 | Cooley |
| 705,691 A | 7/1902 | Morton |
| 1,699,615 A | 1/1929 | Kiyohiko |
| 1,975,504 A | 10/1934 | Anton |
| 1,975,594 A | 10/1934 | Stroud et al. |
| 2,048,651 A | 7/1936 | Norton |
| 2,158,415 A | 5/1939 | Anton |
| 2,158,416 A | 5/1939 | Anton |
| 2,160,962 A | 6/1939 | Anton |
| 2,168,027 A | 8/1939 | Gladding |
| 2,349,950 A | 5/1944 | Anton |
| 3,585,126 A | 6/1971 | Cannon et al. |
| 3,620,970 A | 11/1971 | Klug et al. |
| 3,864,289 A | 2/1975 | Rendall |
| 3,876,738 A | 4/1975 | Marinaccio et al. |
| 3,994,258 A | 11/1976 | Simm |
| 4,043,331 A | 8/1977 | Martin et al. |
| 4,069,026 A | 1/1978 | Simm et al. |
| 4,127,706 A | 11/1978 | Martin et al. |
| 4,143,196 A | 3/1979 | Simm et al. |
| 4,261,834 A | 4/1981 | Dewinter |
| 4,323,525 A | 4/1982 | Bornat |
| 4,510,047 A | 4/1985 | Thompson |
| 4,604,326 A | 8/1986 | Manabe et al. |
| 4,629,563 A | 12/1986 | Wrasidlo |
| 4,650,506 A | 3/1987 | Barris et al. |
| 4,657,793 A | 4/1987 | Fisher |
| 4,704,324 A | 11/1987 | Davis et al. |
| 4,717,498 A | 1/1988 | Maxon |
| 4,778,601 A | 10/1988 | Lopatin et al. |

(Continued)

FOREIGN PATENT DOCUMENTS

| | | |
|---|---|---|
| CN | 2390670 Y | 8/2000 |
| CN | 1471421 A | 1/2004 |

(Continued)

OTHER PUBLICATIONS

Grzenia et al. Tangential flow filtration for virus purification. Journal of Membrane Science 321 (2008) 373-380.*
van Reis et al. Membrane separations in biotechnology. Current Opinion in Biotechnology 2001, 12:208-211.*
Tang et al. Design and Fabrication of Electrospun Polyethersulfone Nanofibrous Scaffold for High-Flux Nanofiltration Membranes. J Polym Sci Part B: Polym Phys 47: 2288-2300, 2009.*
Schwartz. Diafiltration for Desalting or Buffer Exchange. BioProcess International. May 2003, pp. 43-49.*
What is cross-flow velocity. https://www.environmental-expert.com/articles/what-is-cross-flow-velocity-703133. Obtained online Aug. 29, 2019.*

(Continued)

*Primary Examiner* — Nianxiang Zou
(74) *Attorney, Agent, or Firm* — EMD Millipore Corporation

(57) ABSTRACT

Embodiments described herein relate to electrospun nanofiber ultrafiltration membrane compositions capable of operating in tangential filtration mode and methods of using the same.

9 Claims, 22 Drawing Sheets

(56) References Cited

U.S. PATENT DOCUMENTS

| | | |
|---|---|---|
| 4,824,568 A | 4/1989 | Allegrezza, Jr. et al. |
| 4,839,203 A | 6/1989 | Davis et al. |
| 4,849,127 A | 7/1989 | Maxon |
| 4,853,129 A | 8/1989 | Wan |
| 4,938,869 A | 7/1990 | Bayerlein et al. |
| 4,983,268 A | 1/1991 | Kirkpatrick et al. |
| 4,983,288 A | 1/1991 | Karbachsch et al. |
| 5,096,473 A | 3/1992 | Sassa et al. |
| 5,228,994 A | 7/1993 | Tkacik et al. |
| 5,238,106 A | 8/1993 | Nguyen et al. |
| 5,238,568 A | 8/1993 | Fely et al. |
| 5,248,424 A | 9/1993 | Cote et al. |
| 5,264,165 A | 11/1993 | Knight |
| 5,283,106 A | 2/1994 | Seiler et al. |
| 5,435,957 A | 7/1995 | Degen et al. |
| 5,500,167 A | 3/1996 | Degen |
| 5,507,847 A | 4/1996 | George et al. |
| 5,522,601 A | 6/1996 | Murphy |
| 5,522,991 A | 6/1996 | Tuccelli et al. |
| 5,536,413 A | 7/1996 | Bormann et al. |
| 5,620,790 A | 4/1997 | Holzki et al. |
| 5,652,050 A | 7/1997 | Pall et al. |
| 5,693,231 A | 12/1997 | Johnson et al. |
| 5,731,164 A | 3/1998 | Becker et al. |
| 5,739,316 A | 4/1998 | Beer et al. |
| 5,846,438 A | 12/1998 | Pall et al. |
| 5,968,650 A | 10/1999 | Tennent et al. |
| 5,985,112 A | 11/1999 | Fischer |
| 6,045,899 A | 4/2000 | Wang et al. |
| 6,074,869 A | 6/2000 | Pall et al. |
| 6,113,794 A | 9/2000 | Kumar et al. |
| 6,143,675 A | 11/2000 | McCollam et al. |
| 6,153,098 A | 11/2000 | Bayerlein et al. |
| 6,315,805 B1 | 11/2001 | Strauss |
| 6,321,915 B1 | 11/2001 | Wilson et al. |
| 6,464,881 B2 | 10/2002 | Thoraval |
| 6,513,666 B2 | 2/2003 | Meyering et al. |
| 6,554,881 B1 | 4/2003 | Healey |
| 6,598,749 B2 | 7/2003 | Paul et al. |
| 6,604,925 B1 | 8/2003 | Dubson |
| 6,713,011 B2 | 3/2004 | Chu et al. |
| 6,743,273 B2 | 6/2004 | Chung et al. |
| 6,746,517 B2 | 6/2004 | Benson et al. |
| 6,770,204 B1 | 8/2004 | Koslow |
| 6,796,169 B2 | 9/2004 | Makino et al. |
| 6,797,169 B1 | 9/2004 | Ide et al. |
| D500,167 S | 12/2004 | Wong |
| 6,835,311 B2 | 12/2004 | Koslow |
| 6,858,057 B2 | 2/2005 | Healey |
| 6,866,704 B2 | 3/2005 | Koslow |
| 6,866,794 B1 | 3/2005 | Zhang et al. |
| 6,872,311 B2 | 3/2005 | Koslow |
| 6,913,154 B2 | 7/2005 | Koslow |
| 6,924,028 B2 | 8/2005 | Chung et al. |
| 6,953,604 B2 | 10/2005 | Koslow |
| 6,955,775 B2 | 10/2005 | Chung et al. |
| 6,959,820 B2 | 11/2005 | Koslow |
| 6,974,490 B2 | 12/2005 | Gillingham et al. |
| 6,994,811 B2 | 2/2006 | Kools |
| 6,998,058 B2 | 2/2006 | Koslow |
| 7,008,465 B2 | 3/2006 | Graham et al. |
| 7,008,537 B2 | 3/2006 | Koslow |
| 7,070,640 B2 | 7/2006 | Chung et al. |
| 7,070,836 B2 | 7/2006 | Czado |
| 7,090,712 B2 | 8/2006 | Gillingham et al. |
| 7,090,715 B2 | 8/2006 | Chung et al. |
| 7,097,694 B1 | 8/2006 | Jaroszczyk et al. |
| 7,105,228 B2 | 9/2006 | Averdung et al. |
| 7,108,791 B2 | 9/2006 | Tkacik et al. |
| 7,109,136 B2 | 9/2006 | Senecal et al. |
| 7,115,150 B2 | 10/2006 | Johnson et al. |
| 7,144,533 B2 | 12/2006 | Koslow |
| 7,179,317 B2 | 2/2007 | Chung et al. |
| 7,229,665 B2 | 6/2007 | Kools |
| 7,235,122 B2 | 6/2007 | Bryner et al. |
| 7,270,692 B2 | 9/2007 | Gillingham et al. |
| 7,270,693 B2 | 9/2007 | Chung et al. |
| 7,318,853 B2 | 1/2008 | Chung et al. |
| 7,341,663 B2 | 3/2008 | Offeman et al. |
| 7,378,020 B2 | 5/2008 | Ieraci et al. |
| 7,419,601 B2 | 9/2008 | Cooper et al. |
| 7,459,085 B2 | 12/2008 | Koguma et al. |
| 7,470,639 B2 | 12/2008 | Angelini et al. |
| 7,555,195 B2 | 6/2009 | Yamashita et al. |
| 7,585,437 B2 | 9/2009 | Jirsak et al. |
| 7,743,929 B2 | 6/2010 | Kools |
| 7,789,930 B2 | 9/2010 | Ensor et al. |
| 7,790,135 B2 | 9/2010 | Lennhoff |
| 7,875,380 B2 | 1/2011 | Chun et al. |
| 7,927,885 B2 | 4/2011 | Nishita |
| 7,993,523 B2 | 8/2011 | Chen et al. |
| 8,038,013 B2 | 10/2011 | Chen et al. |
| 8,222,166 B2 | 7/2012 | Chu et al. |
| 8,282,712 B2 | 10/2012 | Chi et al. |
| 8,361,180 B2 | 1/2013 | Lim et al. |
| 8,366,797 B2 | 2/2013 | Chung et al. |
| 8,679,217 B2 | 3/2014 | Chi et al. |
| 8,689,985 B2 | 4/2014 | Bates, III et al. |
| 9,174,152 B2 | 11/2015 | Dai et al. |
| 9,180,393 B2 | 11/2015 | Chen et al. |
| 9,623,352 B2 | 4/2017 | Kas et al. |
| 9,750,829 B2 * | 9/2017 | Kozlov .............. A61L 2/0017 |
| 9,889,214 B2 | 2/2018 | Kozlov et al. |
| 9,943,616 B2 | 4/2018 | Kozlov et al. |
| 10,064,965 B2 | 9/2018 | Kozlov et al. |
| 10,252,199 B2 | 4/2019 | Kas et al. |
| 2002/0046656 A1 | 4/2002 | Benson et al. |
| 2002/0084178 A1 | 7/2002 | Dubson et al. |
| 2002/0096246 A1 | 7/2002 | Sennet et al. |
| 2002/0100725 A1 | 8/2002 | Lee et al. |
| 2002/0117439 A1 | 8/2002 | Paul et al. |
| 2002/0124953 A1 | 9/2002 | Sennett et al. |
| 2002/0175124 A1 | 11/2002 | Tkacik et al. |
| 2003/0010002 A1 | 1/2003 | Johnson et al. |
| 2003/0026985 A1 | 2/2003 | Greiner et al. |
| 2003/0121844 A1 | 7/2003 | Koo et al. |
| 2003/0137083 A1 | 7/2003 | Ko et al. |
| 2003/0177909 A1 | 9/2003 | Koslow |
| 2003/0213218 A1 | 11/2003 | Dubson |
| 2003/0213744 A1 | 11/2003 | Kools et al. |
| 2004/0017011 A1 | 1/2004 | Narita et al. |
| 2004/0036014 A1 | 2/2004 | Simon |
| 2004/0038013 A1 | 2/2004 | Schaefer et al. |
| 2004/0038014 A1 | 2/2004 | Schaefer et al. |
| 2004/0070118 A1 | 4/2004 | Czado |
| 2004/0080083 A1 | 4/2004 | Czado |
| 2004/0116025 A1 | 6/2004 | Gogins et al. |
| 2004/0118770 A1 | 6/2004 | Sale et al. |
| 2004/0159609 A1 | 8/2004 | Chase |
| 2004/0206693 A1 | 10/2004 | Charkoudian et al. |
| 2004/0206694 A1 | 10/2004 | Charkoudian |
| 2004/0207126 A1 | 10/2004 | Czado |
| 2004/0255783 A1 | 12/2004 | Graham et al. |
| 2005/0026526 A1 | 2/2005 | Verdegan et al. |
| 2005/0048274 A1 | 3/2005 | Rabolt et al. |
| 2005/0051487 A1 | 3/2005 | Koslow |
| 2005/0053782 A1 | 3/2005 | Sen et al. |
| 2005/0067732 A1 | 3/2005 | Kim et al. |
| 2005/0073075 A1 | 4/2005 | Chu et al. |
| 2005/0142973 A1 | 6/2005 | Bletsos et al. |
| 2005/0163955 A1 | 7/2005 | Schaefer et al. |
| 2005/0210844 A1 | 9/2005 | Kahlbaugh et al. |
| 2005/0235619 A1 | 10/2005 | Heinz et al. |
| 2005/0247236 A1 | 11/2005 | Frey et al. |
| 2005/0260381 A1 | 11/2005 | Ditter et al. |
| 2005/0272925 A1 | 12/2005 | Charkoudian et al. |
| 2006/0016748 A1 | 1/2006 | Koguma et al. |
| 2006/0053782 A1 | 3/2006 | Kobayashi et al. |
| 2006/0057377 A1 | 3/2006 | Harrison et al. |
| 2006/0060519 A1 | 3/2006 | Tkacik et al. |
| 2006/0068668 A1 | 3/2006 | Kameoka et al. |
| 2006/0084340 A1 | 4/2006 | Bond et al. |
| 2006/0084341 A1 | 4/2006 | Bodaghi et al. |
| 2006/0086657 A1 | 4/2006 | Kools |

(56) References Cited

U.S. PATENT DOCUMENTS

| | | |
|---|---|---|
| 2006/0094320 A1 | 5/2006 | Chen et al. |
| 2006/0096912 A1 | 5/2006 | Nussbaumer et al. |
| 2006/0097431 A1 | 5/2006 | Hovanec |
| 2006/0135020 A1 | 6/2006 | Weinberg et al. |
| 2006/0137317 A1 | 6/2006 | Bryner et al. |
| 2006/0137318 A1 | 6/2006 | Lim et al. |
| 2006/0138710 A1 | 6/2006 | Bryner et al. |
| 2006/0138711 A1 | 6/2006 | Bryner et al. |
| 2006/0144782 A1 | 7/2006 | Buck |
| 2006/0149561 A1 | 7/2006 | Govender |
| 2006/0151094 A1 | 7/2006 | Angelini et al. |
| 2006/0160064 A1 | 7/2006 | Carbonell |
| 2006/0213829 A1 | 9/2006 | Rutledge et al. |
| 2006/0230731 A1 | 10/2006 | Kalayci et al. |
| 2006/0246798 A1 | 11/2006 | Reneker et al. |
| 2006/0264139 A1 | 11/2006 | Czado |
| 2006/0264140 A1 | 11/2006 | Andrady et al. |
| 2006/0286446 A1 | 12/2006 | Chun et al. |
| 2006/0286886 A1 | 12/2006 | Komura et al. |
| 2006/0290031 A1 | 12/2006 | Jirsak et al. |
| 2006/0293116 A1 | 12/2006 | Hocknell et al. |
| 2006/0293169 A1 | 12/2006 | Srinivasan et al. |
| 2007/0009736 A1 | 1/2007 | Chuang et al. |
| 2007/0018361 A1 | 1/2007 | Xu |
| 2007/0021021 A1 | 1/2007 | Verdegan et al. |
| 2007/0040305 A1 | 2/2007 | Armantrout et al. |
| 2007/0042069 A1 | 2/2007 | Armantrout et al. |
| 2007/0062855 A1 | 3/2007 | Chase et al. |
| 2007/0074628 A1 | 4/2007 | Jones et al. |
| 2007/0075015 A1 | 4/2007 | Bates, III et al. |
| 2007/0084786 A1 | 4/2007 | Smithies |
| 2007/0113530 A1 | 5/2007 | Morozov et al. |
| 2007/0125700 A1 | 6/2007 | Ding et al. |
| 2007/0134151 A1 | 6/2007 | Jo et al. |
| 2007/0151921 A1 | 7/2007 | Nakano et al. |
| 2007/0163217 A1 | 7/2007 | Frey et al. |
| 2007/0175196 A1 | 8/2007 | Tepper et al. |
| 2007/0196401 A1 | 8/2007 | Naruse et al. |
| 2007/0240576 A1 | 10/2007 | Von Blucher et al. |
| 2007/0298072 A1 | 12/2007 | Kitazono et al. |
| 2008/0004205 A1 | 1/2008 | Tkacik et al. |
| 2008/0004206 A1 | 1/2008 | Rosen et al. |
| 2008/0010959 A1 | 1/2008 | Gillingham et al. |
| 2008/0020192 A1 | 1/2008 | Yen et al. |
| 2008/0022024 A1 | 1/2008 | Mao |
| 2008/0026041 A1 | 1/2008 | Tepper et al. |
| 2008/0034967 A1 | 2/2008 | Ping |
| 2008/0060328 A1 | 3/2008 | Devine |
| 2008/0070463 A1 | 3/2008 | Arora et al. |
| 2008/0073296 A1 | 3/2008 | Dema et al. |
| 2008/0099398 A1 | 5/2008 | Hu et al. |
| 2008/0110342 A1 | 5/2008 | Ensor et al. |
| 2008/0110822 A1 | 5/2008 | Chung et al. |
| 2008/0134652 A1 | 6/2008 | Lim et al. |
| 2008/0136063 A1 | 6/2008 | Chuang et al. |
| 2008/0149561 A1 | 6/2008 | Chu et al. |
| 2008/0150192 A1 | 6/2008 | Perret et al. |
| 2008/0150197 A1 | 6/2008 | Chang et al. |
| 2008/0164214 A1 | 7/2008 | Lerner et al. |
| 2008/0207076 A1 | 8/2008 | Jirsak et al. |
| 2008/0213574 A1 | 9/2008 | Mckee et al. |
| 2008/0217239 A1 | 9/2008 | Chen et al. |
| 2008/0217241 A1 | 9/2008 | Smithies et al. |
| 2008/0217807 A1 | 9/2008 | Lee et al. |
| 2008/0220241 A1 | 9/2008 | Abdelsalam et al. |
| 2008/0237934 A1 | 10/2008 | Reneker et al. |
| 2008/0242171 A1 | 10/2008 | Huang et al. |
| 2008/0264258 A1 | 10/2008 | Mares et al. |
| 2008/0264259 A1 | 10/2008 | Leung |
| 2008/0274312 A1 | 11/2008 | Schelling et al. |
| 2008/0284050 A1 | 11/2008 | Mares et al. |
| 2008/0302074 A1 | 12/2008 | Gebert et al. |
| 2009/0026137 A1 | 1/2009 | Chen et al. |
| 2009/0065436 A1 | 3/2009 | Kalayci et al. |
| 2009/0110873 A1 | 4/2009 | Jiang et al. |
| 2009/0199717 A1 | 8/2009 | Green et al. |
| 2009/0220241 A1 | 9/2009 | Katagiri et al. |
| 2010/0096066 A1 | 4/2010 | Ramaswamy et al. |
| 2010/0139224 A1 | 6/2010 | Lim et al. |
| 2010/0193428 A1 | 8/2010 | Hane et al. |
| 2010/0206803 A1 | 8/2010 | Ward et al. |
| 2010/0316988 A1 | 12/2010 | Sehgal |
| 2011/0163035 A1 | 7/2011 | Cheng et al. |
| 2011/0198282 A1 | 8/2011 | Chu et al. |
| 2011/0206973 A1 | 8/2011 | Brant et al. |
| 2011/0233152 A1 | 9/2011 | Wieczorek et al. |
| 2011/0266213 A1 | 11/2011 | Jo et al. |
| 2011/0305872 A1 | 12/2011 | Li et al. |
| 2012/0061314 A1 | 3/2012 | Choi et al. |
| 2012/0061332 A1 | 3/2012 | Kas et al. |
| 2012/0091072 A1 | 4/2012 | Kozlov et al. |
| 2012/0125847 A1 | 5/2012 | Sehgal |
| 2013/0092622 A1 | 4/2013 | Kas et al. |
| 2014/0061114 A1 | 3/2014 | Ramirez |
| 2014/0116945 A1* | 5/2014 | Kas .................. B01D 67/0004 210/651 |
| 2015/0037055 A1 | 2/2015 | Kitagawa et al. |
| 2015/0298070 A1 | 10/2015 | Koslov et al. |
| 2015/0360157 A1 | 12/2015 | Hwang et al. |
| 2016/0016124 A1 | 1/2016 | Zheng et al. |
| 2016/0136558 A1 | 5/2016 | Zheng et al. |
| 2016/0136584 A1 | 5/2016 | Hwang et al. |
| 2016/0166961 A1 | 6/2016 | Haberkamp et al. |
| 2016/0175748 A1 | 6/2016 | Park |
| 2016/0193555 A1 | 7/2016 | Park |
| 2017/0173509 A1 | 6/2017 | Giglia et al. |
| 2017/0173511 A1 | 6/2017 | Kas et al. |
| 2017/0360969 A1 | 12/2017 | Kozlov et al. |

FOREIGN PATENT DOCUMENTS

| | | |
|---|---|---|
| CN | 1625429 A | 6/2005 |
| CN | 1942616 A | 4/2007 |
| CN | 101272840 A | 9/2008 |
| CN | 101318090 A | 12/2008 |
| CN | 101564656 A | 10/2009 |
| CN | 102227247 A | 10/2011 |
| CN | 102448508 A | 5/2012 |
| CN | 102917777 A | 2/2013 |
| CN | 104321133 A | 1/2015 |
| CN | 106457079 A | 2/2017 |
| DE | 19545701 C1 | 5/1997 |
| EP | 257635 A2 | 3/1988 |
| EP | 320033 A1 | 6/1989 |
| EP | 497594 A1 | 8/1992 |
| EP | 168783 B1 | 6/1994 |
| EP | 781600 A2 | 7/1997 |
| EP | 1743975 A1 | 1/2007 |
| EP | 1745808 A1 | 1/2007 |
| EP | 1829603 A1 | 9/2007 |
| EP | 1878482 A1 | 1/2008 |
| EP | 1673493 B1 | 7/2009 |
| EP | 2174703 A1 | 4/2010 |
| EP | 2599908 A1 | 6/2013 |
| EP | 2222385 B1 | 6/2016 |
| GB | 1519070 A | 7/1978 |
| JP | 2-161954 A | 6/1990 |
| JP | 4-351645 A | 12/1992 |
| JP | 7-213876 A | 8/1995 |
| JP | 2000-61277 A | 2/2000 |
| JP | 2000-325764 A | 11/2000 |
| JP | 2005-515880 A | 6/2005 |
| JP | 2005-270965 A | 10/2005 |
| JP | 2005-536347 A | 12/2005 |
| JP | 2006082006 A | 3/2006 |
| JP | 2006-326579 A | 12/2006 |
| JP | 2006341233 A | 12/2006 |
| JP | 2007-75739 A | 3/2007 |
| JP | 2007-105724 A | 4/2007 |
| JP | 2007-301436 A | 11/2007 |
| JP | 2007-332342 A | 12/2007 |
| JP | 2008049239 A | 3/2008 |
| JP | 2008-162098 A | 7/2008 |
| JP | 2009-509754 A | 3/2009 |

(56) References Cited

FOREIGN PATENT DOCUMENTS

| | | |
|---|---|---|
| JP | 2009050851 A | 3/2009 |
| JP | 2009-148748 A | 7/2009 |
| JP | 2009148746 A | 7/2009 |
| JP | 2009183879 A | 8/2009 |
| JP | 2009233550 A | 10/2009 |
| JP | 2010-094962 A | 4/2010 |
| JP | 2011529778 A | 12/2011 |
| JP | 2012-520761 A | 9/2012 |
| JP | 2012-523320 A | 10/2012 |
| JP | 2014208342 A | 11/2014 |
| KR | 10-2005-0077304 A | 8/2005 |
| KR | 10-2006-0079211 A | 7/2006 |
| KR | 10-0871440 B1 | 12/2008 |
| KR | 1020100023152 A | 3/2010 |
| KR | 10-2010-0037055 A | 4/2010 |
| WO | 97/20622 A1 | 6/1997 |
| WO | WO-9742835 A1 | 11/1997 |
| WO | 9916810 A1 | 4/1999 |
| WO | WO-0005358 A1 | 2/2000 |
| WO | 00/45933 A1 | 8/2000 |
| WO | 0056804 A1 | 9/2000 |
| WO | 0058388 A1 | 10/2000 |
| WO | 0101047 A1 | 1/2001 |
| WO | WO-0107599 A1 | 2/2001 |
| WO | 01/14047 A1 | 3/2001 |
| WO | 03/016601 A1 | 2/2003 |
| WO | 03037959 A1 | 5/2003 |
| WO | 03/064013 A1 | 8/2003 |
| WO | 03/080905 A1 | 10/2003 |
| WO | 2004/018079 A2 | 3/2004 |
| WO | 2005/024101 A1 | 3/2005 |
| WO | 2005073441 A1 | 8/2005 |
| WO | 2006016800 A1 | 2/2006 |
| WO | 2006/068100 A1 | 6/2006 |
| WO | 2006/131081 A1 | 12/2006 |
| WO | 2006131061 A1 | 12/2006 |
| WO | 2007/001405 A2 | 1/2007 |
| WO | 2007011477 A2 | 1/2007 |
| WO | 2007/041311 A2 | 4/2007 |
| WO | 2007/054039 A1 | 5/2007 |
| WO | 2007/054040 A2 | 5/2007 |
| WO | 2007054050 A1 | 5/2007 |
| WO | 2007/054040 A3 | 8/2007 |
| WO | 2007098889 A1 | 9/2007 |
| WO | 2007/111477 A1 | 10/2007 |
| WO | 2007/137530 A2 | 12/2007 |
| WO | 2007144189 A2 | 12/2007 |
| WO | 2008/034190 A1 | 3/2008 |
| WO | 2008/073507 A2 | 6/2008 |
| WO | 2008/106903 A2 | 9/2008 |
| WO | 2008/109117 A1 | 9/2008 |
| WO | 2008106803 A1 | 9/2008 |
| WO | 2008142023 A2 | 11/2008 |
| WO | 2009/010020 A1 | 1/2009 |
| WO | 2009/017086 A1 | 2/2009 |
| WO | 2009/032040 A1 | 3/2009 |
| WO | 2009/064767 A2 | 5/2009 |
| WO | 2009063067 A2 | 5/2009 |
| WO | 2009064757 A1 | 5/2009 |
| WO | 2009/071909 A1 | 6/2009 |
| WO | 2009119638 A1 | 10/2009 |
| WO | 2010/042647 A2 | 4/2010 |
| WO | 2010042706 A1 | 4/2010 |
| WO | 2010049535 A1 | 5/2010 |
| WO | 2010/069296 A1 | 6/2010 |
| WO | 2010/107503 A1 | 9/2010 |
| WO | 2010/120668 A1 | 10/2010 |
| WO | 2010127634 A1 | 11/2010 |
| WO | 2010147763 A2 | 12/2010 |
| WO | 2011/019686 A1 | 2/2011 |
| WO | 2011/151314 A1 | 12/2011 |
| WO | 2012/021308 A2 | 2/2012 |
| WO | 2012021208 A2 | 2/2012 |
| WO | 2012/135679 A2 | 10/2012 |
| WO | 2012/135679 A9 | 1/2013 |
| WO | 2013/013241 A2 | 1/2013 |
| WO | 2014/093345 A1 | 6/2014 |
| WO | 2014/159124 A1 | 10/2014 |
| WO | 2015/200239 A1 | 12/2015 |

OTHER PUBLICATIONS

International Search Report received for PCT Application No. PCT/US2013/074132, dated Mar. 21, 2014, 3 pages.

International Search Report and Written Opinion Received for PCT Application No. PCT/US2015/037055, dated Sep. 15, 2015, 7 pages.

International Search Report and Written Opinion Received for PCT Application No. PCT/US2016/018146, dated Jun. 7, 2016, 11 pages.

Raghavan et al., "Novel Electrospun Poly(vinylidene fluoride-co-hexafluoropropylene)-In Situ $SiO_2$ Composite Membrane-Based Polymer Electrolyte for Lithium Batteries", Journal of Power Sources, vol. 184, Issue 2, Oct. 1, 2008, pp. 437-443.

Roche et al., "Methods Used to Validate Microporous Membranes for the Removal of Mycoplasma", BioPharm, vol. 5, Issue 3, Apr. 1992, pp. 22-23.

Rutledge et al., "Formation of Fibers by Electrospinning", Advanced Drug Delivery Reviews, vol. 59, Issue 14, Dec. 10, 2007, pp. 1384-1391.

Sang et al., "Filtration by a Novel Nanofiber Membrane and Alumina Adsorption to Remove Copper(II) from Groundwater", Journal of Hazardous Materials, vol. 153, Issues 1-2, May 1, 2008, pp. 860-866.

Sang et al., "Heavy Metal-Contaminated Groundwater Treatment by a Novel Nanofiber Membrane", Desalination, vol. 223, Issues 1-3, Mar. 1, 2008, pp. 349-360.

Sill et al., "Electrospinning: Applications in Drug Delivery and Tissue Engineering", Biomaterials, vol. 29, Issue 13, May 2008, pp. 1989-2006.

Smit et al., "Continuous Yarns from Electrospun Fibers", Polymer, vol. 46, Issue 8, Mar. 29, 2005, pp. 2419-2423.

Strathmann, H., "Preparation of Microporous Membranes by Phase Inversion Processes", Membranes and Membrane Processes, Springer, 1986, pp. 115-135.

Tan et al., "Systematic Parameter Study for Ultra-Fine Fiber Fabrication via Electrospinning Process", Polymer, vol. 46, Issue 16, Jul. 25, 2005, pp. 6128-6134.

Teo et al., "A Review on Electrospinning Design and Nanofibre Assemblies", Nanotechnology, vol. 17, No. 14, Aug. 2006, pp. R89-R106.

Wang et al., "Electrospun Nanofibrous Membranes for High Flux Microfiltration", Journal of Membrane Science, vol. 392-393, Mar. 1, 2012, pp. 167-174.

Yarin et al., "Upward Needleless Electrospinning of Multiple Nanofibers", Polymer, vol. 45, Issue 9, Apr. 2004, pp. 2977-2980.

Yoon et al., "High Flux Ultrafiltration Membranes based on Electrospun Nanofibrous PAN Scaffolds and Chitosan Coating", Polymer, vol. 47, Issue 7, Mar. 22, 2006, pp. 2434-2441.

Yoshimatsu et al., "Selective Molecular Adsorption using Electrospun Nanofiber Affinity Membranes", Biosensors and Bioelectronics, vol. 23, Issue 7, Feb. 28, 2008, pp. 1208-1215.

Yun et al., "Nanoparticle Filtration by Electrospun Polymer Fibers", Chemical Engineering Science, vol. 62, Issue 17, Sep. 2007, pp. 4751-4759.

Zeman et al., "Steric Rejection of Polymeric Solutes by Membranes with Uniform Pore Size Distribution", Separation Science and Technology, vol. 16, No. 3, Apr. 1981, pp. 275-290.

Zhao et al., "Preparation and Properties of Electrospun Poly (Vinylidene Fluoride) Membranes", Journal of Applied Polymer Science, vol. 97, Apr. 2005, pp. 466-474.

Zwijnenberg et al., "Acetone-Stable Nanofiltration Membranes in Deacidifying Vegetable Oil", Journal of the American Oil Chemists' Society, vol. 76, No. 1, 1999, pp. 83-87.

ASTM International, "Standard Test Methods for Pore Size Characteristics of Membrane Filters by Bubble Point and Mean Flow Pore Test1", Designation: F316-03, 2003, pp. 1-7.

(56) References Cited

OTHER PUBLICATIONS

ASTM International, "Standard Test Method for Determining Bacterial Retention of Membrane Filters Utilized for Liquid Filtration", ASTM F838-05, 2005, 6 pages.
Extended European Search Report received for EP Patent Application No. 07114167.5, dated Nov. 6, 2007, 7 pages.
Extended European Search Report received for EP Patent Application No. 10181774.0, dated Nov. 25, 2010, 5 pages.
ASTM International, "Standard Test Method for Pore Size Characteristics of Membrane Filters using Automated Liquid Porosimeter", E 1294-89, Reapproved 1999, 2 pages.
ASTM International, "Standard Method for Thickness of Textile Materials", Designation: D 1777-64, Reapproved 1975, pp. 477-478.
ASTM International, "Standard Test Method for Determining Bacterial Retention of Membrane Filters Utilized for Liquid Filtration", Designation: F838-15a, 2015, 6 pages.
ASTM International, "Standard Test Method for Thickness of Textile Materials", ASTM D1777-96 (Reapproved 2015), Sep. 2015, 5 pages.
ASTM International, "Standard Test Methods for Pore Size Characteristics of Membrane Filters by Bubble Point and Mean Flow Pore Test", Designation: F316-03 (Reapproved 2011), 2011, 7 pages.
Aussawasathien et al., "Separation of Micron to Sub-Micron Particles from Water: Electrospun Nylon-6 Nanofibrous Membranes as Pre-Filters", Journal of Membrane Science, vol. 315, 2008, pp. 11-19.
Barhate et al., "Nanofibrous Filtering Media: Filtration Problems and Solutions from Tiny Materials", Journal of Membrane Science, vol. 296, Issues 1-2, Jun. 15, 2007, pp. 1-8.
Barhate et al., "Preparation and Characterization of Nanofibrous Filtering Media", Journal of Membrane Science, vol. 283, Issues 1-2, Oct. 20, 2006, pp. 209-218.
Bhanushali et al., "Advances in Solvent-Resistant Nanofiltration Membranes: Experimental Observations and Applications", Annals of the New York Academy of Sciences, vol. 984, Mar. 2003, pp. 159-177.
Bjorge et al., "Performance Assessment of Electrospun Nanofibers for Filter Applications", Desalination, doi:10.1016/j.desal.2009.06.064, 2009, 7 pages.
Blackwell, James V., "Mycoplasma—Recent Developments in Detecting and in Preventing Bioreactor Contamination", BioProcess Technology Consultants, Inc., ISPE Annual Meeting Scottsdale, Arizona, Nov. 6-10, 2005, 38 pages.
Blanchard, Mark M., "Quantifying Sterilizing Membrane Retention Performance", BioProcess International, vol. 5, No. 5, May 2007, 6 pages.
Blond et al., "Strong, Tough, Electrospun Polymer-Nanotube Composite Membranes with Extremely Low Density", Advanced Functional Materials, vol. 18, Issue 17, Sep. 10, 2008, pp. 2618-2624.
Database WPI, "Week 200935", Thomson Scientific London, GB, 2009-F08014; XP-002726900, 2 pages.
Deitzel et al., "The Effect of Processing Variables on the Morphology of Electrospun Nanofibers and Textiles", Polymer, vol. 42, Issue 1, Jan. 2001, pp. 261-272.
Dimmock et al., "Introduction to Modern Virology", Blackwell Publishing Limited, Appendixes: Survey of Virus Properties, Viruses with ssDNA genomes (class 2), 2007, p. 450.
Doshi et al., "Electrospinning Process and Applications of Electrospun Fibers", Journal of Electrostatics, vol. 35, Issues 2-3, Aug. 1995, pp. 151-160.
Duan et al., "Preparing Graphitic Nanoribbons from Ultrathin Electrospun Poly(methyl methacrylate) Nanofibers by Electron Beam Irradiation", 2nd IEEE International Nanoelectronics Conference (INEC 2008), Mar. 24-27, 2008, pp. 33-38.
Ebert et al., "Solvent Resistant Nanofiltration Membranes in Edible Oil Processing", Membrane Technology, vol. 107, 1999, pp. 5-8.

Galka, Ned, "Life Sciences: Trends in Biopharmaceutical Filtration and Clarification", Filtration & Separation, vol. 44, No. 3, Apr. 2007, pp. 18-21.
Gibson et al., "Transport Properties of Porous Membranes Based on Electrospun Nanofibers", Colloids and Surfaces A: Physicochemical and Engineering Aspects, vols. 187-188, Aug. 31, 2001, pp. 469-481.
Gopal et al., "Electrospun Nanofibrous Polysulfone Membranes as Pre-filters: Particulate Removal", Journal of Membrane Science, vol. 289, 2007, pp. 210-219.
Granath et al., "Molecular Weight Distribution Analysis by Gel Chromatography on Sephadex", Journal of Chromatography A, vol. 28, 1967, pp. 69-81.
Guo et al., "Cellulose Membrane used as Stationary Phase of Membrane Affinity Chromatography", Chinese Chemical Letters, vol. 5, No. 10, 1994, pp. 869-872.
Aranha, Hazel, "Ensuring Safety of Biopharmaceuticals: Virus and Prion Safety Considerations", Chapter 20, Edited by Meltzer et al., Filtration and Purification in the Biopharmaceutical Industry, 2nd edition, Informa Healthcare USA, Inc., 2008, pp. 543-577.
Hou et al., "Poly(p-xylylene) Nanotubes by Coating and Removal of Ultrathin Polymer Template Fibers", Macromolecules, vol. 35, 2002, pp. 2429-2431.
Huang et al., "Electrospun Polymer Nanofibres with Small Diameters", Nanotechnology, vol. 17, No. 6, Feb. 21, 2006, pp. 1558-1563.
Kim et al., "Characterization and Properties of P(VdF-HFP)-Based Fibrous Polymer Electrolyte Membrane Prepared by Electrospinning", Journal of the Electrochemical Society, vol. 152, No. 2, Jan. 2005, pp. A295-A300.
Lev et al., "Water Filtration by Nanotextiles", Nanocon 2010, Oct. 2010, 6 pages.
Levit et al., "Supercritical CO2-Assisted Electrospinning", The Journal of Supercritical Fluids, vol. 31, Issue 3, Nov. 2004, pp. 329-333.
Li et al., "Collecting Electrospun Nanofibers with Patterned Electrodes", Nano Letters, vol. 5, No. 5, 2005, pp. 913-916.
Lin et al., "Preparation of Poly(ether sulfone) Nanofibers by Gas-Jet/Electrospinning", Journal of Applied Polymer Science, vol. 107, 2008, pp. 909-917.
Lyons et al., "Melt Electrospinning of Polymers: A Review", Polymer News, vol. 30, No. 6, 2005, pp. 170-178.
Ma et al., "Electrospun Cellulose Nanofiber as Affinity Membrane", Journal of Membrane Science, vol. 265, Issues 1-2, Nov. 15, 2005, pp. 115-123.
Ma et al., "Surface Modified Nonwoven Polysulphone (PSU) Fiber Mesh by Electrospinning: A Novel Affinity Membrane", Journal of Membrane Science, vol. 272, Issues 1-2, Mar. 15, 2006, pp. 179-187.
Meltzer, T. H., "In Filtration in the Pharmaceutical Industry", Marcel Dekker: New York, 1987, p. 103.
Na et al., "Effect of Hot-Press on Electrospun Poly(vinylidene fluoride) Membranes", Polymer Engineering & Science, vol. 48, Issue 5, May 2008, pp. 934-940.
International Preliminary Report on Patentability and Written Opinion Received for PCT Application No. PCT/US2012/047865, dated Jan. 21, 2014, 9 pages.
International Preliminary Report on Patentability and Written Opinion Received for PCT Application No. PCT/US2013/074132, dated Jun. 16, 2015, 5 pages.
International Preliminary Report on Patentability and Written Opinion received for PCT Patent Application No. PCT/US012/031549, dated Oct. 10, 2013, 10 pages.
International Search Report and Written Opinion received for PCT Patent Application No. PCT/US012/031549, dated Nov. 28, 2012, 15 pages.
International Preliminary Report on Patentability received for PCT Application No. PCT/US2010/000826 dated Sep. 29, 2011, 9 pages.
International Search Report received for PCT Application No. PCT/US2010/000826 dated Aug. 16, 2010, 5 pages.
International Preliminary Report on Patentability and Written Opinion received for PCT Patent Application No. PCT/US2011/045905, dated Feb. 21, 2013, 7 pages.

(56) References Cited

OTHER PUBLICATIONS

International Search Report and Written Opinion received for PCT patent Application No. PCT/US2011/045905, dated Mar. 19, 2012, 13 pages.
International Search Report and Written Opinion received for PCT Patent Application No. PCT/US2012/047865, dated Feb. 26, 2013, 18 pages.
"ASTM E1294-89 Withdrawal Notice", 2008, p. 1.
"ASTM International, Designation: F838-83, Standard Test Method for Determining Bacterial Retention of Membrane Filters Utilized for Liquid Filtration," 2005, pp. 1-9.
ATCC, "Product Data Sheet, Brevundimonas diminuta, ATCC 19146", pp. 1-2.
Extended European Search Report issued in European Application No. 17195327.6, dated Aug. 16, 2018, 10 pages.
Huang, et al., "A Review on Polymer Nanofibers by Electrospinning and their Applications in Nanocomposites", Composites Science and Technology, vol. 63, No. 15., 2003, pp. 2223-2253.
Jiang, et al., "Professional Knowledge of Traditional Chinese Pharmacology", Jun. 2007, 233 pages.
"International Search Report and Written Opinion issued in International Application No. PCT/US2012/047665", dated Jan. 10, 2012, 8 pages.
"International Preliminary Report on Patentability issued in International Application No. PCT/US2015/037055", dated Jan. 5, 2017, 7 pages.
Sajid, et al., "Designs, Formats and Applications of Lateral Flow Assay: A Literature Review", Journal of Saudi Chemical Society, vol. 19, Sep. 16, 2014, pp. 689-705.
Segers, et al., "Classification of Pseudomonas diminuta Leifson and Hugh 1954 and Pseudomonas vesicularis Busing, Doll, and Freytag 1953 in *Brevundimonas* gen. nov. as Brevundimonas diminuta comb. nov. and Brevundimonas vesicularis comb. nov., Respectively", International Journal of Systematic Bacteriology, vol. 44, No. 3, Jul. 1994, pp. 499-510.

* cited by examiner

SEM Image of NF UF at 100,000X

SEM Image of PES UF at 100,000X

NF UF fiber diameter measurements

Water permeability vs Mean Flow Bubble Point (IPA)

Dextran Sieving Curves used to determine Dextran R90 cutoffs for NF UF and PES UF Gel Permeation Chromatogram of Feed A (0.0385% w/w) in pH 7.0, 50 mM phosphate buffer Gel Permeation Chromatogram of Feed B (0.844% w/w) in pH 7.0, 50 mM phosphate buffer Flux vs TMP for NF UF and PES UF with Feed A
(0.0385% w/w)

Flux vs TMP for NF UF and PES UF with Feed B
(0.844% w/w)

Flux vs TMP for NF UF and PES UF with Feed C
(8.44% w/w)

Gel permeation chromatograms showing Mass Transport through NF UF during Flux vs TMP for Feed A (0.0385% w/w)

Gel permeation chromatograms showing Mass Transport through PES UF during Flux vs TMP for Feed A (0.0385% w/w)

Mass/Concentration Transport of D7250, D2000, D110 for NF UF and PES UF through the Flux vs TMP experiment for feed A (0.0385% w/w)

Mass/Concentration Transport of D7250, D2000, D110 for NF UF and PES UF through the Flux vs TMP experiment for feed B (0.844% w/w)

Selectivity D110/D2000 and D110/D7250 vs Flux for NF UF and PES UF throught the Flux vs TMP experiment for Feed A (0.0385% w/w)

Selectivity D110/D2000 and D110/D7250 vs Flux for NF UF and PES UF throught the Flux vs TMP experiment for Feed B (0.844% w/w)

Feed, Retentate, and Permeate Gel permeation chromatograms of Feed A (0.0385% w/w) during Diafiltration using NF UF at 30 LMH and 640 RPM Feed, Retentate, and Permeate Gel permeation chromatograms of Feed A (0.0385% w/w) during Diafiltration using PES UF at 30 LMH and 640 RPM Retentate $C/C_O$ vs diavolumes of Feed A (0.0385% w/w) for NF UF and PES UF during Diafiltration at 30 LMH and 640 RPM Selectivity in Retentate D7250/D110 and D2000/D110 vs diavolumes for NF UF and PES UF during Diafiltration at 30 LMH and 640 RPM Retentate C/C₀ vs diavolumes of Feed A (0.0385% w/w) for NF UF and PES UF during Diafiltration at 60 LMH and 320 RPM Selectivity in Retentate D7250/D110 and D2000/D110 vs diavolumes for NF UF and PES UF during Diafiltration at 60 LMH and 320 RPM Flux vs Concentration factor for NF UF and PES UF during Ultrafiltration concentration of Feed A (0.0385% w/w) at 0.5 psi constant TMP and 600 RPM $C/C_{theo}$ vs Concentration factor for NF UF and PES UF during 2, 4, 8x Ultrafiltration concentration of Feed A (0.0385% w/w) at 0.5 psi constant TMP and 600 RPM C/C$_{theo}$ vs Flux for NF UF and PES UF during 2, 4, 8x (Left to Right) Ultrafiltration concentration of Feed A (0.0385% w/w) at 0.5 psi constant TMP and 600 RPM C/C$_{theo}$ vs Flux for NF UF and PES UF during 2, 4, 8x (Left to Right) Ultrafiltration concentration of Feed B (0.844% w/w) at 5 psi constant TMP and 600 RPM C/Ctheo vs Flux for NF UF and PES UF during 2, 4, 8x (Left to Right) Ultrafiltration concentration of Feed B (0.844% w/w) at 7 psi constant TMP and 600 RPM Flux vs Concentration factor for NF UF and PES UF during Ultrafiltration concentration of Feed C (8.44% w/w) at 5 psi constant TMP and 300 RPM. TMP was increased to 12 psi after the 2x concentration point.

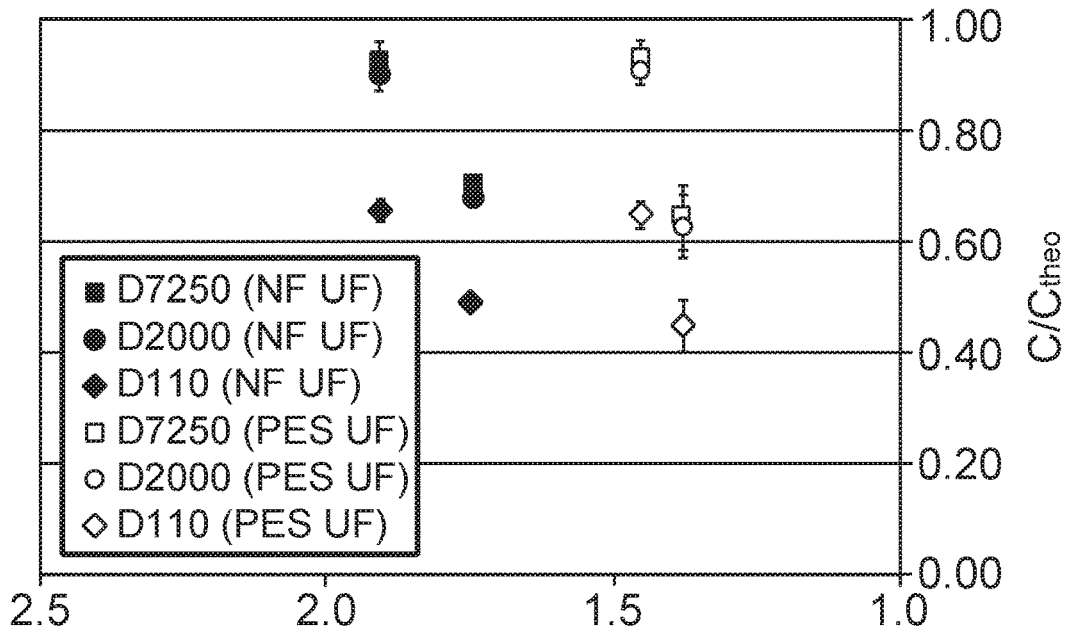

Figure 31

C/Ctheo vs Flux for NF UF and PES UF during 2 and 3x (Left to Right) Ultrafiltration concentration of Feed C (8.44% w/w) at 5 psi constant TMP and 300 RPM. TMP was increased to 12 psi after the 2x concentration point.

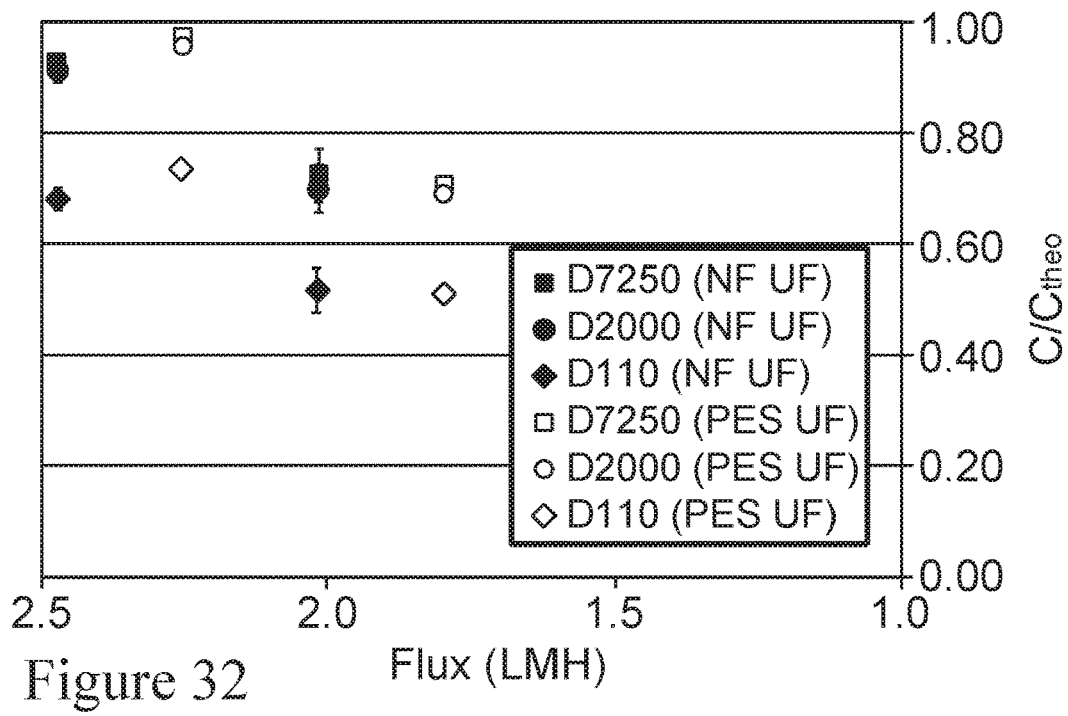

Figure 32

C/Ctheo vs Flux for NF UF and PES UF during 2 and 3x (Left to Right) Ultrafiltration concentration of Feed C (8.44% w/w) at 7 psi constant TMP and 300 RPM. TMP was increased to 12 psi after the 2x concentration point.

METHOD OF PURIFYING A BIOLOGICAL MATERIAL OF INTEREST IN A SAMPLE USING NANOFIBER ULTRAFILTRATION MEMBRANES OPERATED IN TANGENTIAL FLOW FILTRATION MODE

CROSS-REFERENCE TO RELATED APPLICATIONS

The present application is a US National Stage application of International Application No. PCT/US2016/018146, filed Feb. 17, 2016, which claims the benefit of priority of U.S. Provisional Application No. 62/148,793, filed Apr. 17, 2015, each of which is incorporated by reference herein in its entirety.

Embodiments disclosed herein relate to nanofiber ultrafiltration compositions capable of operating in tangential filtration mode and methods of using the same.

BACKGROUND

Membrane filtration is a separation technique widely used both for bench scale as well as process scale purification of biological materials. There are different types of membranes used in filtration, which are classified as microfiltration or ultrafiltration membranes depending on the pore size. Microfiltration membranes generally have pore size ranging between 0.1 µm and 10 µm; whereas, ultrafiltration membranes have a much smaller pore size, ranging between 0.001 and 0.1 µm. Because of the difference in the pore size, these membranes are used for different purposes. For example, microfiltration membranes are generally used for clarification, sterilization, and removal of microparticulates or for cell harvesting and ultrafiltration membranes are generally used for fractionation or for concentrating molecules (such as, for example, proteins, peptides, nucleic acids, carbohydrates, and other biological materials). Ultrafiltration membranes are typically classified by molecular weight cutoff, rather than pore size.

There are two main types of filtration modes which are generally employed with microfiltration and ultrafiltration membranes. One of the filtration modes is called Normal Flow Filtration (NFF) mode, also known as "dead-end" filtration, which generally applies the feed stream perpendicular to the membrane face and attempts to pass 100% of the fluid through the membrane. Another filtration mode is called Tangential Flow Filtration (TFF), where the feed stream is parallel to the membrane face, where one portion passes through the membrane (i.e., permeate) while the remainder is retained and may be recirculated back to the feed reservoir (i.e., retentate).

TFF mode of filtration is preferred for the purification of certain types of biological materials, for example those having a size of 500 kDa or larger than 500 kDa, where TFF is employed for concentration and impurity clearance. Most TFF applications employ ultrafiltration membranes which are useful for concentration and buffer exchange steps etc. One example of an ultrafiltration membrane which is used in TFF mode for manufacturing of certain biological materials (e.g., proteins, vaccines and virus-like particles) is a solution immersion cast ultrafiltration membrane made from polyethersulfone (PES).

Most ultrafiltration membranes widely used in TFF mode are required to be shipped in wet state and also with preservatives to prevent contamination by micoorganisms. However, not only is shipping in wet state difficult as it requires controlling the environmental conditions to prevent drying out and freezing of the membrane but the preservatives added to the membrane material often have to be removed prior to use in the purification of biological materials in order to avoid the preservatives from ending up in the sample containing the final product, e.g., a therapeutic protein or a vaccine.

SUMMARY

Embodiments disclosed herein demonstrate the applicability of electrospun nanofiber membrane compositions in the manufacturing of biological materials such as, for example, virus-like particles, proteins and conjugated polysaccharide vaccines (generally biological materials having a molecular weight about or greater than 500 KDa) and provide an alternative to and an improvement over currently used solution immersion cast PES membranes. Specifically, in contrast to the solution immersion cast PES membranes, the electrospun nanofiber membranes can be shipped in a dry state and also do not require the use of preservatives.

The electrospun nanofiber membranes used in the embodiments described herein have an equivalent or improved performance to the solution immersion cast PES ultrafiltration membrane in Tangential Flow Filtration (TFF) mode.

In various embodiments, method of purifying a biological material of interest in a sample is provided, wherein the method comprises the steps of: (a) providing a sample containing the biological material of interest having a molecular weight equal to or greater than 500 KDa; (b) contacting the sample in tangential filtration mode with an electrospun nanofiber membrane composition comprising nanofibers having an average fiber diameter less than 15 nm, thereby resulting in a permeate and a retentate; and (c) collecting the retentate containing the biological material of interest, thereby to purify the biological material of interest.

In some embodiments, the biological material of interest is selected from a therapeutic protein, a conjugated polysaccharide vaccine and a virus-like particle.

In some embodiments, the collecting step comprises increasing the concentration of the biological material of interest. In other embodiments, the collecting step comprises diafiltration.

In some embodiments, the electrospun nanofiber compositions exhibit higher water permeability in TFF mode compared to a solution cast polymeric membrane.

In some embodiments, the electrospun nanofiber membrane compositions exhibit a higher flux in TFF mode compared to a solution cast polymeric membrane.

In some embodiments, the electrospun nanofiber membrane composition is made from Nylon-6.

In some embodiments, the methods of purification result in at least 90% yield or greater than 90% yield of the biological material of interest.

In various embodiments, the electrospun nanofiber membrane composition is incorporated into a device suitable for TFF, such as, for example, a cassette, or a spiral wound device.

BRIEF DESCRIPTION OF THE DRAWINGS

In FIG. 13, the gel permeation chromatograms of Feed A permeates for 1 of the 2 duplicates of the NF UF and their feeds are shown. The x-axis is Dextran molecular weight in Daltons (Da) on a lop) scale. The area on the y-axis translates from refractive index detector response in milliVolts after integration with the GPC molecular weight standards.

FIG. 14 shows the gel permeation chromatograms of Feed A permeates through 1 of the 2 duplicates of the PES UF membrane and their feeds. The x-axis is Dextran molecular weight in Daltons (Da) on a $\log_{10}$ scale. The area on the y-axis translates from refractive index detector response in milliVolts after integration with the GPC molecular weight standards.

FIG. 19 shows the feed as the largest peak and the retentates in solid lines at each increasing diavolume in decreasing height. The permeates are shown by dashed lines where increasing diavolumes results in lower peaks.

FIG. 20 shows the feed as the largest peak and the retentates in solid lines at each increasing diavolume in decreasing height. The permeates are shown by dashed lines where increasing diavolumes results in lower peaks.

FIG. 31 is a graph depicting the average $C/C_{theo}$ on the y-axis versus average feed flux in LMH on the x-axis during 2 and 3× (Left to Right) ultrafiltration concentration of Feed C for the NF UF and the PES UF membranes at 5 psi constant TMP and 300 RPM in Example 9. Permeate volume over time determines the flux and tracks concentration factors. Retentate samples are taken at each concentration factor for GPC analysis to determine yield and selectivity of D7250, D2000, and D110 as described in Example 4. The flux units are Liters of Feed C per square meter of membrane times hours (LMH) on the y-axis.

FIG. 32 is a graph depicting the average $C/C_{theo}$ on the y-axis versus average feed flux in LMH on the x-axis during 2 and 3× (Left to Right) ultrafiltration concentration of Feed C for the NF UF and the PES UF membranes at 7 psi constant TMP and 300 RPM in Example 9. Permeate volume over time determines the flux and tracks concentration factors. Retentate samples are taken at each concentration factor for GPC analysis to determine yield and selectivity of D7250, D2000, and D110 as described in Example 4. The flux units are Liters of Feed C per square meter of membrane times hours (LMH) on the y-axis.

DETAILED DESCRIPTION

Figure 1:
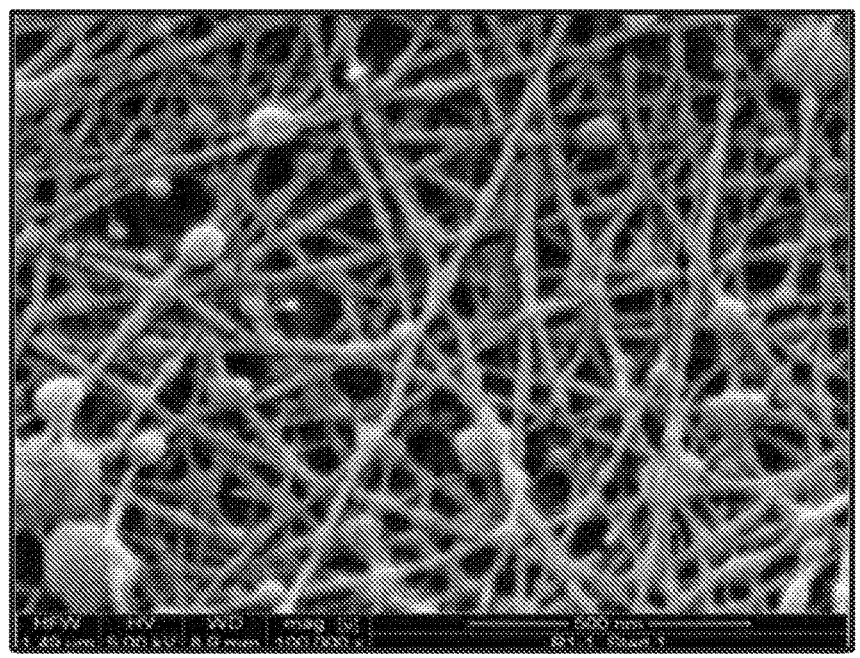
FIG. 1 depicts a scanning electron micrograph of an electrospun Nylon-6 nanofiber ultrafiltration membrane (referred to as "NF UF") at 100,000 times magnification.

The embodiments described herein employ electrospun nanofiber membrane compositions, as previously described in PCT Publication no. WO2014093345, in TFF mode for the purification of biological materials of interest such as, for example, therapeutic proteins, virus-like particles and conjugated polysaccharide vaccines. The electrospun nanofiber membrane compositions used in the methods described herein are of exceptionally high uniformity and exhibit increased permeability and a higher process flux relative to solution immersion cast ultrafiltration membranes which are typically used in the purification of biological materials.

Most conventional polymeric ultrafiltration membranes are made by the solution phase inversion process. This process involves the conversion of a homogeneous polymer solutions of two or more components into a two-phase system with a solid, polymer-rich phase forming the rigid membrane structure and a liquid, polymer-poor phase forming the membrane pores. (see, for example, Membranes and Membrane Processes, 1986 Springer US, Drioli, Enrico; Nakagaki, Masayuki. Preparation of Microporous Membranes by Phase Inversion Processes, Strathmann, H., p 115-135). This can be accomplished with a variety of polymers and mixtures but is often challenging because of the sensitive kinetic and thermodynamic conditions required to generate membranes with the desired properties. Multiple variables exist that can affect membrane formation including polymer molecular weight, concentration, temperature, miscibility, solvent and non-solvent properties and composition, humidity, and substrates and often require complex process and environmental controls.

However, electrospun nanofiber ultrafiltration membranes (e.g., NF UF described herein) can be made using a much simpler manufacturing process using polymers such as Nylon-6. Nanofibers are simply drawn out of polymer solution using a high voltage source. Electrospinning does not rely on the complexity and sensitive nature of phase inversion (like traditional membranes), which depends on a variety parameters and is usually much more difficult to control.

The embodiments described herein are based, at least in part, on the surprising and unexpected finding that the electrospun nanofiber membrane compositions perform similarly to or better than solution immersion cast ultrafiltration membranes made from polymers such as polyethersulfone (PES), when used in TFF mode for the purification of biological materials having at least 500 KDa molecular weight such as, for example, certain therapeutic proteins, virus-like particles and conjugated polysaccharide vaccines and other similar sized biological materials. In some embodiments, the electrospun nanofiber compositions used in the embodiments described herein result in at least 90% product yield, or greater than 90% product yield, or at least 95% product yield, or greater than 95% product yield.

The NF UF membranes exhibit a higher water permeability that translates into higher process flux and greater mass transport when used in TFF mode over conventional membranes that are used in TFF mode, e.g., a polyethersulfone ultrafiltration membrane. This also results in faster process times and smaller membrane area required to process the same feed amount, in turn translating into lower costs. As demonstrated by the Examples herein, an improvement of about 30% is observed in case of the NF UF membrane relative to PES UF membrane.

Electrospun nanofiber membrane or mat compositions are highly porous polymeric materials, where the "pore" size of the composition is linearly proportional to the fiber diameter of the electrospun nanofiber, while the porosity of the membrane or mat is relatively independent of the fiber diameter and usually falls in the narrow range of 85-90%.

The random nature of electrospun nanofiber mat or membrane formation has led to the general assumption that such compositions are generally unsuitable for any critical filtration of liquid streams. Applications of electrospun compositions for the removal of relatively large particles (such as bacteria) from solutions using normal filtration have recently begun to appear in the literature (see, for example, International PCT Publication No. WO2010/107503; Wang et al., 'Electrospun nanofibrous membranes for high flux microfiltration", Journal of Membrane Science, 392-393 (2012) 167-174)). However, there have been no published reports describing the use of electrospun nanofiber mats/membranes in TFF mode for the purification of biological materials of interest, as described herein.

In order that the embodiments disclosed herein may be more readily understood, certain terms are first defined. Additional definitions are set forth throughout the detailed description.

I. Definitions

The phrase "Tangential Flow Filtration" or "TFF" refers to a mode of filtration which is useful for clarifying, concentrating and purifying biological materials, e.g., proteins and vaccines. In Tangential Flow Filtration (TFF) mode of filtration, the fluid is pumped tangentially along the surface of the membrane. An applied pressure serves to force a portion of the sample through the membrane to the filtrate side (referred to as the permeate). Biological materials and particulates that are too large to pass through the membrane pores are retained on the upstream side (referred to as retentate). However, in contrast to normal filtration mode, the retained materials do not build up at the surface of the membrane. Instead, they are swept along the face of the membrane by tangential flow of fluid. TFF may also be referred to as "cross-flow filtration."

The phrase "Transmembrane Pressure" or "TMP" refers to the average applied pressure from the feed to the filtrate side of the membrane. TMP is calculated as follows: TMP [bar]=[($P_F$+$P_R$)/2]−Pf, where [bar] is a metric unit of pressure exactly equal to 100000 Pascal, where Pascal is defined as one Newton per square meter; $P_F$ is the applied pressure of the feed; $P_R$ is the pressure of the retentate; and $P_r$ is the pressure of the filtrate The term "ultrafiltration" of "UF" refers to membrane filtration technique which employs controlled pore, semi permeable membranes to concentrate or fractionate dissolved molecules. Molecules much larger than the pores are retained in the feed solution and are concentrated in direct proportion to the volume of liquid that passes through the membrane. Molecules having a size which is close to the pore size of the membrane concentrate to a lesser extent with some of the molecules passing through the membrane in the permeate. The concentration of freely permeable molecules (salts) in the sample remains essentially unchanged. Membranes suitable for ultrafiltration (referred to as ultrafiltration or UF membranes) are defined by the molecular weight cut-off (MWCO) of the membrane used. Ultrafiltration can be applied in cross-flow or dead-end mode.

The term "diafiltration" refers to a technique that uses ultrafiltration membranes to completely remove, replace or lower the concentration of salts or solvents from solutions containing proteins, peptides, nucleic acids, and other biomolecules. The process selectively utilizes permeable (porous) membrane filters to separate the components of solutions and suspensions based on their molecular size. An ultrafiltration membrane retains molecules that are larger than the pores of the membrane while smaller molecules such as salts, solvents and water, which are 100% permeable, freely pass through the membrane. During diafiltration, buffer is introduced into the recycle tank while filtrate is removed from the unit operation. In processes where the product is in the retentate, diafiltration washes components out of the product pool into the filtrate, thereby exchanging buffers and reducing the concentration of undesirable species. When the product is in the filtrate, diafiltration washes it through the membrane into a collection vessel.

The term "diavolume" refers to a measure of the extent of washing that has been performed during a diafiltration step. It is based on the volume of diafiltration buffer introduced into a unit operation compared to the retentate volume. If a constant volume diafiltration is being performed, where the retentate volume is held constant and diafiltration buffer enters at the same rate that filtrate leaves, a diavolume is calculated as follows: DV=total buffer volume introduced into the operation during diafiltration/retentate volume.

The term "concentration factor" refers to the amount by which a product has been concentrated in the feed stream.

The term "concentration" refers to the relative amount of a given substance contained within a solution or in a particular volume of space or the amount of solute per unit volume of solution. As used herein, concentration is measured by the number of biological molecules or materials of interest per solution volume.

The term "polymer" refers to a large molecule, or macromolecule, composed of many repeated subunits. Polymers range from familiar synthetic plastics such as polystyrene to natural biopolymers such as DNA and proteins that are fundamental to biological structure and function. Polymers, both natural and synthetic, are generally created via polymerization of many small molecules, known as monomers. Polymers suitable for use in the formation of nanofiber compositions used in the embodiments described herein include thermoplastic and thermosetting polymers. Additional exemplary polymers which may be used for making nanofiber compositions as described below.

The term "nylon" as used herein refers to nylon-6, nylon-6,6, nylon 6,6-6,10, and copolymers, derivative compounds, blends and combinations thereof.

The term "nanofibers" refers to fibers having diameters varying from a few tens of nanometers up to several hundred nanometers, but generally less than one micrometer.

The term "nanofiber composition," as used herein, refers to an assembly of multiple nanofibers in the form of a mat or membrane, such that the thickness of the mat or membrane is at least about 10 times greater than the diameter of a single fiber in the mat or membrane. The nanofibers can be arranged randomly in the mat or membrane, or be aligned along one or multiple axes.

The term "electrospinning," as used herein, refers to an electrostatic spinning process of producing nanofibers from a polymer solution or melt by applying an electric potential to such solution. The electrostatic spinning process for making an electrospun nanofiber mat or membrane for a filtration medium, including suitable apparati for performing the electrostatic spinning process are described in detail in International Publication Nos. WO 2005/024101, WO 2006/131081, and WO 2008/106903, each of which is incorporated by reference herein. In some embodiments, the nanofiber compositions are made from a single nanofiber, wherein the single nanofiber is made by a single pass of a moving collection apparatus positioned between the spinning drum and the collector through the process. A fibrous web of nanofibers can be formed by one or more spinning drums running simultaneously above the same moving collection apparatus.

In some embodiments, a fibrous mat/membrane is made by depositing nanofiber (s) from a nylon solution. The nanofiber mat/membrane has a basis weight of between about 5 g/m$^2$ and about 15 g/m$^2$, as measured on a dry basis, i.e., after the residual solvent has been evaporated or removed.

The phrase "electrospun nanofiber composition" or "electrospun nanofiber membrane composition" refers to a porous nanofiber mat or membrane made from a polymer using the electrospinning process. The electrospun nanofiber composition generally has a porosity ranging from about 80% to about 95%, a thickness ranging from about 1 μm to about 500 μm or from about 50 μm to about 200 μm, and a liquid permeability greater than about 300 LMH/psi. In some embodiments of described herein, electrospun nanofibers are produced having an average diameter of less than 15 nm. In some embodiments, the average diameter of the electrospun nanofibers is between 6 nm and 13 nm.

In some embodiments, the electrospun nanofiber compositions are incorporated into a suitable TFF device or a module, such as, for example, a cassette such as a Millipore Pellicon® 3 cassette, a spiral wound device or a hollow fiber device. The NF UF membranes may be easier to incorporate into devices, such as spiral wound or flat cassettes, and may exhibit greater product recovery, higher concentration factors, require less equipment and energy to operate, smaller manufacturing footprint, require lower pumping capacity, and provide less air-liquid interface, lower risk of contamination, and better product quality.

In general, the use of the nanofiber compositions in TFF mode results in greater product recovery (greater than 90% yield or greater than 95% yield), higher concentration factors, less equipment use and energy to operate, lower pumping capacity, smaller manufacturing footprint, less air-liquid interface, as well as potentially lower risk of contamination, and better product quality.

Screens are often inserted into the feed and/or filtrate channels in spiral wound and flat plate or cassette modules to increase turbulence in the channels and reduce concentration polarization. This is not an option, however, with hollow fiber modules. In a hollow fiber module, the feed stream is pumped into the lumen (inside) of the tube and filtrate passes through the membrane to the shell side, where it is removed. Because of the very open feed flowpath, low shear is generated even with moderate crossflow rates. While this may be useful for highly shear sensitive products, in general it reduces the efficiency of the module by requiring very high pumping capacity to achieve competitive fluxes.

The terms "flux" and "flow rate" are used interchangeably herein to refer to the rate at which a volume of fluid passes through the electrospun nanofiber compositions described herein.

The term "filtrate" or "permeate," as used interchangeably herein, refers to the solution that crosses a filter or membrane, e.g., an electrospun nanofiber composition used herein, as well as the solution that has already crossed a filter or membrane.

The term "retentate," as used herein, refers to the component or portion of the solution that is retained and does not cross a filter or membrane, e.g., a electrospun nanofiber composition used herein, as well as that which has not yet crossed a filter or membrane. In case a Stirred Cell is employed, the liquid with solute that remains on the upstream side of the filter or membrane in a Stirred Cell is referred to as the retentate. In case of a TFF cassette or spiral device, the liquid which flows through the feed/retentate channels of a cassette or spiral device and returns from the device back to the feed tank is referred to as the retentate.

The term "Stirred Cell," as used herein, refers to an apparatus that simulates or creates tangential flow filtration with stirring to generate cross-flow on the retentate side of a membrane, where gas pressure is applied directly to Stirred Cell. Solutes above the membrane's molecular weight (MW) cut-off are retained in cell, while water and solutes below the cut-off pass into the filtrate and out of cell.

The term "effective pore size", as used herein, describes a structural property of a porous material assessed with a functional, rather than visual, method. For the purposes of comparing porous materials with dramatically different structures, such as solution-cast membranes and nanofiber mats/membranes, visual methods like microscopy are usually inadequate in predicting whether these materials would be expected to perform similarly in the same application. However, functional methods, such as bubble point measurements, liquid-liquid porometry, intrusion porosimetry, sieving of macromolecules and/or particles of given sizes, allow one of skilled in the art to compare the properties of different materials. Thus, comparisons are possible between different materials, which can be described having "smaller," "larger" or "similar" effective pore sizes depending on how they perform in a functional test.

The term "dextran" as used herein refers to a complex, branched glucan (polysaccharide made of many glucose molecules) composed of chains of varying lengths (from 3 to 10,000 kilodaltons).

The term "polysaccharide" or "polysaccharides" are polymeric carbohydrate molecules composed of long chains of monosaccharide units bound together by glycosidic linkages and on hydrolysis give the constituent monosaccharides or oligosaccharides. Polysaccharides range in structure from linear to highly branched. Examples include storage polysaccharides such as starch and glycogen, and structural polysaccharides such as cellulose and chitin.

Polysaccharides are often quite heterogeneous, containing slight modifications of the repeating unit. Depending on the structure, these macromolecules can have distinct properties from their monosaccharide building blocks. They may be amorphous or even insoluble in water. When all the monosaccharides in a polysaccharide are the same type, the polysaccharide is called a homopolysaccharide or homoglycan, but when more than one type of monosaccharide is present they are called heteropolysaccharides or heteroglycans.

The term "conjugated polysaccharide vaccine" as used herein refers to a vaccine which is created by covalently attaching an antigen (e.g., a polysaccharide or polysaccharide based organism) to a carrier protein (preferably from the same microorganism), thereby conferring the immunological attributes of the carrier on the attached antigen. An unconjugated polysaccharide antigen cannot be loaded onto the MHC complex, which can only bind peptides, and thus will not be presented to a T cell for activation of the presenting B cell. In the case of a conjugated polysaccharide vaccine, the carrier peptide linked to the polysaccharide target antigen is able to be presented on the MHC molecule. The T cell that recognizes the carrier peptide will activate the B cell, causing it to produce antibodies to the polysaccharide antigen that it had originally bound. This technique for the creation of an effective immunogen is most often applied to bacterial polysaccharides for the prevention of invasive bacterial disease. Examples of conjugated polysaccharide vaccines known in the art include, but are not limited to, *Haemophilus influenzae* B (Hib; bacterial meningitis and pneumonia) [Merck, Sanofi, GSK], *Neissera meningitides* (bacterial meningitis), [Wyeth Pharmaceuticals, Inc., a subsidiary of Pfizer Inc.], and *Streptococcus pneumonia* (bacterial pneumonia) includes the 13-valent pneumococcal conjugate vaccine (PCV13 [Prevnar 13, Wyeth Pharmaceuticals, Inc., a subsidiary of Pfizer Inc.]). Bioconjugate vaccines against. *S. aureus* and *P. aeruginosa*, are also under development.

The term "virus-like particles" refers to biological materials which resemble viruses, but are non-infectious because they do not contain any viral genetic material. The expression of viral structural proteins, such as Envelope or Capsid, can result in the self-assembly of virus like particles (VLPs). VLPs derived from the Hepatitis B virus and composed of the small HBV derived surface antigen (HBsAg) were described over 40 years ago from patient sera. More recently, VLPs have been produced from components of a wide variety of virus families including Parvoviridae (e.g. adeno-associated virus), Retroviridae (e.g. HIV), and Flaviviridae (e.g. Hepatitis C virus). VLPs can be produced in a variety of cell culture systems including mammalian cell lines, insect cell lines, yeast, and plant cells.

The phrase "biological material of interest," as used herein, refers to proteins, virus like particles and vaccines, especially conjugated polysaccharide vaccines, which may be purified using the embodiments described herein. Such biological materials of interest typically have a molecular weight of about 500,000 Daltons or greater than 50000 Daltons.

II. Exemplary Nanofiber Polymeric Materials

Polymers which may be employed for making nanofiber compositions used in the methods described herein include thermoplastic and thermoset polymers. Nonlimiting examples of suitable polymers include nylon, polyimide, aliphatic polyamide, aromatic polyamide, polysulfone, cellulose, cellulose acetate, polyether sulfone, polyurethane, poly(urea urethane), polybenzimidazole, polyetherimide, polyacrylonitrile, poly(ethylene terephthalate), polyethylene, polypropylene, polyaniline, poly(ethylene oxide), poly (ethylene naphthalate), poly(butylene terephthalate), styrene butadiene rubber, polystyrene, poly(vinyl chloride), poly (vinyl alcohol), poly(vinyl acetate), poly(vinylidene fluoride), poly(vinyl butylene), copolymers, derivative compounds, blends and combinations thereof. Suitable polyamide condensation polymers, include nylon-6; nylon-4,6; nylon-6,6; nylon 6,6-6,10; copolymers of the same, and other linear generally aliphatic nylon compositions and the like.

III. Exemplary Methods for Forming a Fibrous Mat/Membrane

In various embodiments, the nanofiber compositions used in the various embodiments described herein are made using electrospinning processes, which are previously known in the art.

In some embodiments, a fibrous mat/membrane is made by depositing nanofiber(s) from a nylon solution. The nanofiber mat/membrane has a basis weight of between about 0.1 $g/m^2$ and about 10 $g/m^2$, as measured on a dry basis, (i.e., after the residual solvent has evaporated or otherwise been removed).

In other embodiments, nylon is dissolved in a mixture of solvents including, but not limited to, formic acid, sulfuric acid, acetic acid, 2,2,2-trifluoroethanol, 2,2,2,3,3,3-hexafluoropropanol, and water.

In some embodiments, the nylon solution is prepared by dissolving dry nylon polymer in one group of solvents, i.e. first preparing a stock solution, and then adding other solvents to make the solution ready for electrospinning.

In some embodiments, the nylon polymer (i.e., starting solution) is partially hydrolyzed over the course of solution preparation, such that the average molecular weight of the partially hydrolyzed nylon polymer (i.e., ending solution) is less than the average molecular weight of the starting nylon polymer.

In an additional embodiment of the invention, conductivity of the nylon solution is adjusted with a suitable ionizable compound in a given solvent. Examples of such suitable ionizable compounds include, but are not limited to, organic and inorganic salts, acids and bases. An example of a preferred compound used to adjust the conductivity of a nylon solution is ammonium formate.

In another embodiment of the invention, the environment inside the electrospinning chamber is controlled to ensure that ambient humidity is kept at dew point above approximately 12° C.

In one embodiment of the invention, a variety of porous single or multilayered substrates or supports are arranged on a moving or stationary collection belt to collect and combine with the electrospun nanofiber mat medium, forming a composite filtration device.

IV. Methods of Using the Membranes in TFF Filtration Mode

In various embodiments described herein, the electrospun nanofiber compositions are used in TFF mode to purify a biological material of interest (e.g., a protein, conjugated polysaccharide vaccine or a virus-like particle) having a molecular weight of about or greater than 500 KDa.

In case of operation in TFF mode, a pump is generally used to generate flow of the feed stream through the channel between two membrane surfaces. During each pass of fluid over the surface of the membrane, the applied pressure forces a portion of the fluid through the membrane and into the filtrate stream. The result is a gradient in the feedstock concentration from the bulk conditions at the center of the channel to the more concentrated wall conditions at the membrane surface. There is also a concentration gradient along the length of the feed channel from the inlet to the outlet (retentate) as progressively more fluid passes to the filtrate side.

In some embodiments, the electrospun Nylon-6 Nanofiber Ultrafiltration membrane (NF UF) can be incorporated into Tangential flow filtration modules of several format types similar to the PES UF membrane. The most common formats used for tangential flow filtration are flat plate cassettes (e.g., Pellicon® 3) or spiral wound devices. The NF UF can be made into flat sheet tangential flow filtration packets in a layered structure containing the membrane, retentate and permeate screens, and an outer polymeric film having retentate and permeate ports and then over-molded or injection molded into a flat cassette device with retentate and permeate ports. Alternatively, the NF UF can be wound into a spiral with retentate and permeate screens and sealed on the edges to provide a retentate and permeate flow path and then placed in a cylindrical holder with sealed flow paths to separate retentate and permeate ports. Polymer screens are inserted into the retentate and/or permeate channels in spiral wound and flat plate modules to increase turbulence in the channels and reduce concentration polarization. The turbulence promoted channels have higher mass transfer coefficients at lower cross flow rates, meaning that higher fluxes are achieved with lower pumping requirements. Turbulence-promoted retentate channels are, therefore, more efficient than open channels. Using a suspended screen in a flat plate module gives some of the benefits of both open and turbulence-promoted channels.

Tangential flow filtration using NF UF membrane can concentrate and purify a biological material of interest such as a conjugated polysaccharide vaccine to a higher purity level by permeating out the smaller impurities and reducing the volume to increase the concentration to 20 mg/mL of the vaccine product. Also the NF UF membrane can retain the biological material and diafilter or perform a buffer exchange of small salts or pH buffers salts for additional purification steps or final formulation. The experiments described in the Examples below can be used to purify, concentrate, or buffer exchange a conjugate polysaccharide vaccine or biological molecule of interest in the same way as the model Dextrans used herein.

Embodiments are further illustrated by the following examples which should not be construed as limiting. The contents of all references, patents and published patent applications cited throughout this application, as well as the Figures, are incorporated herein by reference.

EXAMPLES

Example 1: Preparation of Nanofiber Mats/Membranes

Electrospun Nylon-6 nanofiber composite parvovirus retentive mats are made as described in the PCT published patent application no. WO2014093345, incorporated herein by reference, and are designated NF UF (i.e., Nanofiber UF membrane). Nylon-6 under the trademark Ultramid B24 (BASF Corp., Florham Park, N.J., USA) is used to electrospin the bilayered composite base and active retentive layer nanofiber mats from solution onto a smooth Hirose nonwoven substrate (Hirose Paper Manufacturing Co., Ltd, Tosa-City, Kochi, Japan, part number # HOP-60HCF). The base layer is electrospun from 10.3% w/w Nylon-6 in Acetic: Formic Acid mixture (2:1) and is approximately 25-30 microns thick with an average fiber diameter of 70 nm. The active retentive layer with an average fiber diameter of 10 nm is electrospun from a solution of 8.0% w/w Nylon-6 in Acetic acid:Formic acid:water: 2,2,2-trifluroethanol (TFE): Ammonium Formate mixture (20.5:20.5:10.3:40:0.7) and is estimated to be a few microns thick. The electospun Nanofiber UF membranes are produced on a pilot scale electrospinning apparatus from Elmarco (Liberec, Czech Republic) using three rotating electrodes at 60 Hz, distance of 140 mm, controlled humidity between 10° and 16° dew point, voltage of 60 kV, and line speed of 2 cm/min.

Example 2: Preparation of Polyethersulfone Ultrafiltration Membranes

Polyethersulfone ultrafiltration membranes (PES UF) are custom made using solution immersion casting onto a polyolefin nonwoven substrate using custom membrane casting equipment (EMD Millipore, Jaffrey, N.H. USA).

Generally, the solution immersion process involves the conversion of a homogeneous polymer solutions of two or more components into a two-phase system with a solid, polymer-rich phase forming the rigid membrane structure and a liquid, polymer-poor phase forming the membrane pores. (see, e.g., as described in: Membranes and Membrane Processes, 1986 Springer US, Drioli, Enrico; Nakagaki, Masayuki. Preparation of Microporous Membranes by Phase Inversion Processes, Strathmann, H., p 115-135).

Example 3: Investigation of Membrane Characterizations

The characteristics of the two membranes, NF UF and PES UF, are investigated using various techniques described below.

1. SEM Images and Fiber Diameter

Figure 2:
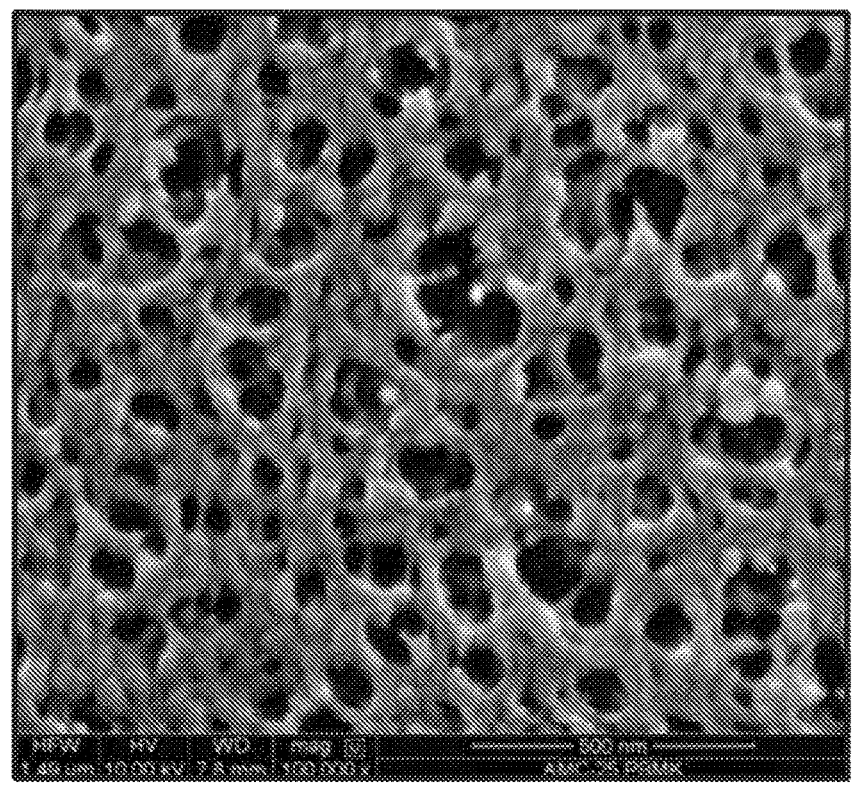
FIG. 2 depicts a scanning electron micrograph of the polyethersulfone ultrafiltration membrane (referred to as "PES UF") at 100,000 times magnification that is made using solution immersion casting.

Representative scanning electron micrographs (SEM images) of the electrospun Nylon-6 Nanofiber ultrafiltration membrane (NF UF) and the polyethersulfone ultrafiltration membrane (PES UF) are shown in FIGS. 1 and 2, respectively. In FIG. 1, samples are cut from the discs and mounted on an aluminum SEM stub with double-sided conductive carbon tape. They are then coated with 5 nm of iridium using a Cressington 208HR high resolution sputter coater. The samples are imaged in a FEI Quanta 200F field emission scanning electron microscope (FESEM) at 5 kV. The image shows that the Nylon-6 nanofibers are a random overlaying non-woven mat of polymeric fibers with a diameter on the order of ~10 nanometers relative to the 500 nanometer scale bar. The porosity in the electrospun NylonNF UF results from the spaces between the overlapping fibers.

FIG. 2 depicts that the porosity of a polyethersulfone ultrafiltration membrane (PES UF) made using a solution phase inversion process. Samples are cut from membrane disks and then mounted on an aluminum SEM stub with double-sided conductive carbon tape. They are then coated with 5 nm of iridium using a Cressington 208HR high resolution sputter coater. The sample images are taken in an FEI Quanta 200F field emission scanning electron microscope (FESEM) at 5 kV.

Comparing the PES UF in FIG. 2 to FIG. 1 of the electrospun Nylon-6 NF UF shows how drastically different they are in terms of 3-dimensional structure or morphology.

Figure 3:
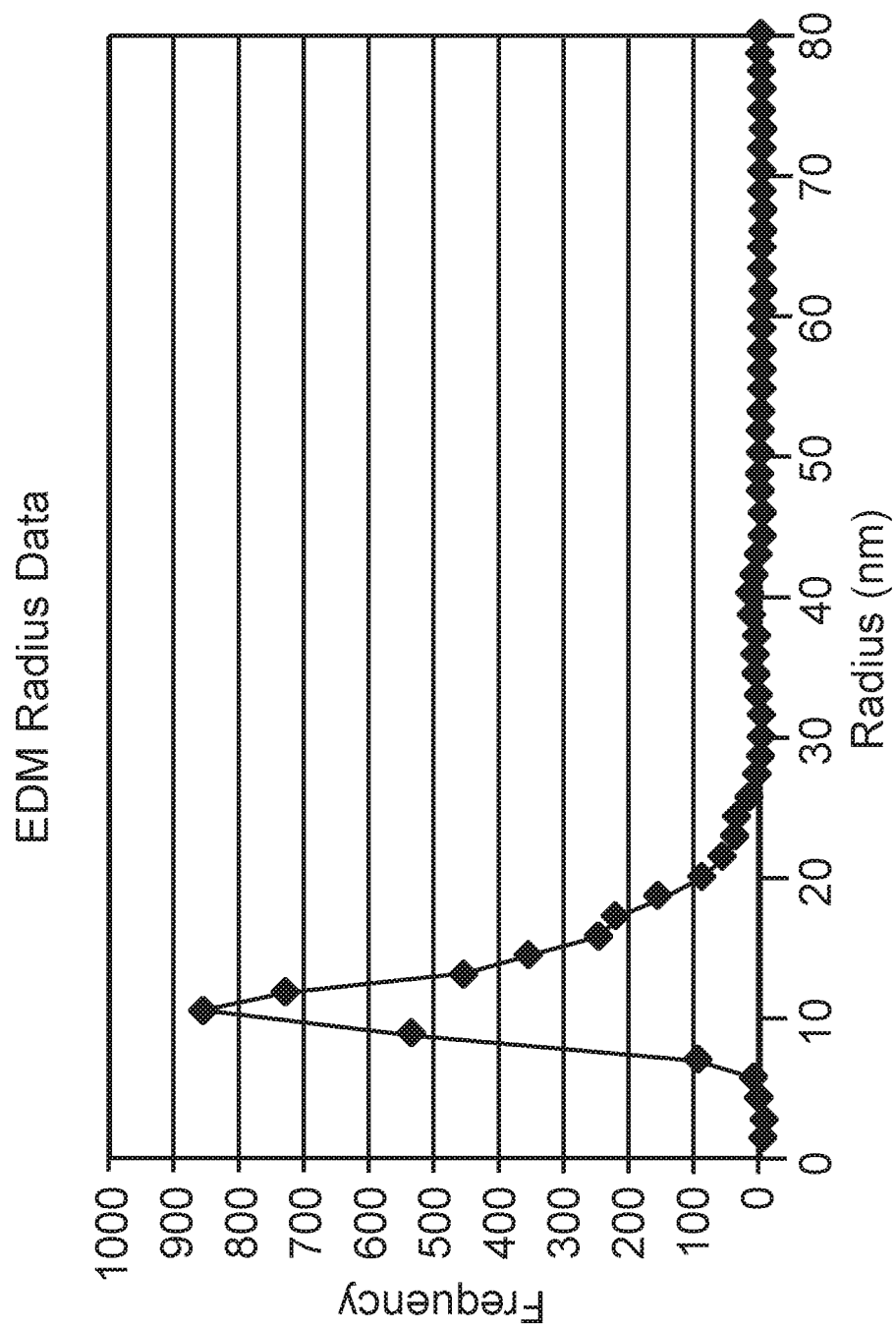
FIG. 3 depicts a graph measuring the diameter of the NF UF membrane fibers. The NF UF random fiber radius measurements are made using a Scanning Electron Micrograph (SEM) similar to that in FIG. 1 and a custom Euclidean Distance Map (EDM) routine within Image Pro Plus v6.0. The x-axis is the radius of the fibers in nanometers. The y-axis is the frequency or number of measurements for each radius in nanometers on the x-axis.

Fiber radius, as shown in FIG. 3, is measured utilizing a custom developed Euclidean Distance Map (EDM) routine within Image Pro Plus v6.0. The average fiber diameter of each nanofiber layer sample is calculated and the final diameter is determined by subtracting the 5 nm of the metal coating applied during sample preparations for SEM. The mean fiber diameter of the Electrospun Nylon-6 Nanofiber Ultrafiltration membrane (NF UF) is two times the mean radius, then subtracting the 5 nanometers of the metal coating of the sample preparation for SEM.

2. Mean Flow Bubble Point and Water Permeability

This experiment describes the measurement of the mean bubble point and water permeability, as measured for the NF UF and the PES UF membranes. As demonstrated herein and shown in FIG. 4, the NF UF membrane samples exhibit higher water permeability at similar or higher mean flow bubble points than the 4 different samples of the PES UF membranes prescreened for benchmarking.

Mean flow bubble point is measured according to ASTM E1294-89, "Standard Test Method for Pore Size Characteristics of Membrane Filters Using Automated Liquid Porosimeter". The automated bubble point method according to ASTM F316 using a custom-built capillary flow porosimeter is similar, in principle, to a commercial apparatus from Porous Materials, Inc. (Ithaca, N.Y., USA). Nanofiber UF (NF UF) membrane samples die cut to 25 mm in diameter with a polyolefin nonwoven substrate are wetted with perfluorohexane Fluorinert™ FC-72 (10 dynes/cm), commercially available from (3M, St. Paul, Minn. USA). Each sample is placed in a holder, a differential pressure of air is applied and the fluid removed from the sample. The differential pressure at which wet flow is equal to one-half the dry flow (flow without wetting solvent) is used to calculate the mean flow pore size using supplied software.

Figure 4:
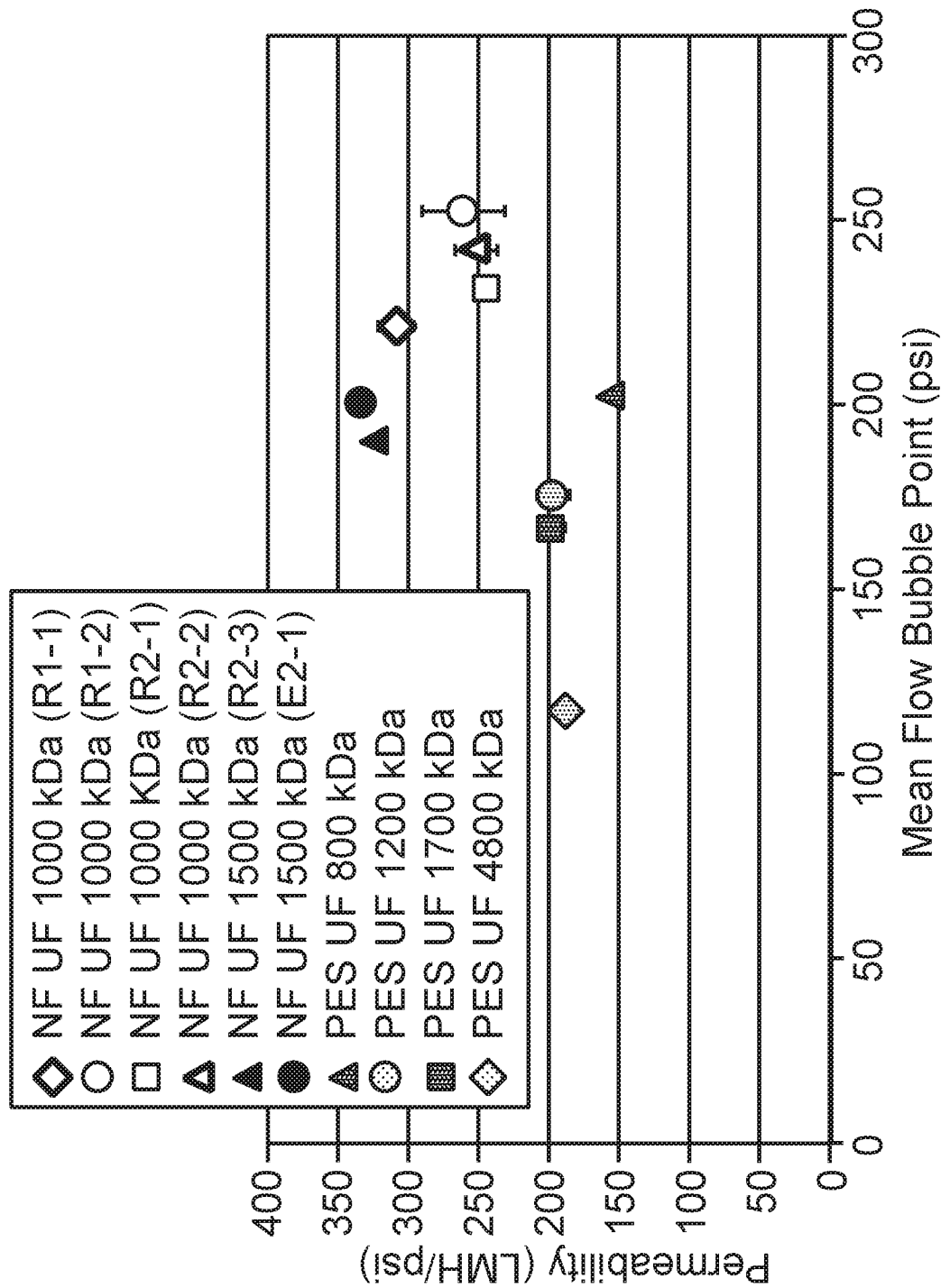
FIG. 4 is a graph depicting the average water permeability in LMH/psi (y-axis) versus mean flow bubble point in psi (x-axis) for six different samples of the NF UF membrane and four different samples of the PES UF membranes. The six NF UF membrane samples are: NF UF 1000 kDa (R1-1); (R1-2); (R2-1); (R2-2); and NF UF 1500 kDa (R2-3); and (E2-1), as shown in the figure key. The four PES UF membrane samples are: PES UF 800 kDa; 1200 kDa; 1700 kDa; and 4800 kDa, as shown in the figure key. The numbers before the unit kDa (kiloDaltons) indicate the Dextran sieving R90 cutoffs for the UF membranes, where a membrane retains 90% of Dextrans with a molecular weight above the kDa value. The water permeability units are Liters of water per square meter of membrane×hours X pounds per square inch of applied pressure (LMH/psi) on the y-axis. The mean flow bubble point unit is pounds per square inch (psi) for the solvent 2-propanol.

Mean flow bubble points of the Polyethersulfone UF (PES UF) membranes are measured using 2-propanol. NF UF membrane mean flow bubble points are adjusted to the surface tension of 2-propanol (21.4 dynes/cm) for comparison to PES UF samples, as shown in FIG. 4. FIG. 4 shows that four samples of the Electrospun Nylon-6 NF UF membranes with Dextran sieving R90 cutoffs of 1000 kDa have greater water permeability and higher Mean Flow Bubble Points than the PES UF membranes with a Dextran sieving R90 cutoff of 1200 kDa.

Water permeability in LMH/psi is measured using 44.5 mm diameter membrane disks in 50 mL Stirred Cells (Model 8050, EMD Millipore, Billerica, Mass.) with a filter area of 13.4 $cm^2$ area and 0.5 mL hold-up volume at 3 psi. NF UF membranes die cut with a polyolefin nonwoven substrate are placed dry onto a second polyolefin nonwoven substrate and secured into the Stirred Cell. PES UF membranes are wet with ethanol, exchanged into water, and secured into the Stirred Cell on a second polyolefin nonwoven disk. Samples are water wet and flushed with 2×50 mL water at 5 psi to remove all air.

3. Dextran R90 Cutoffs

Figure 5:
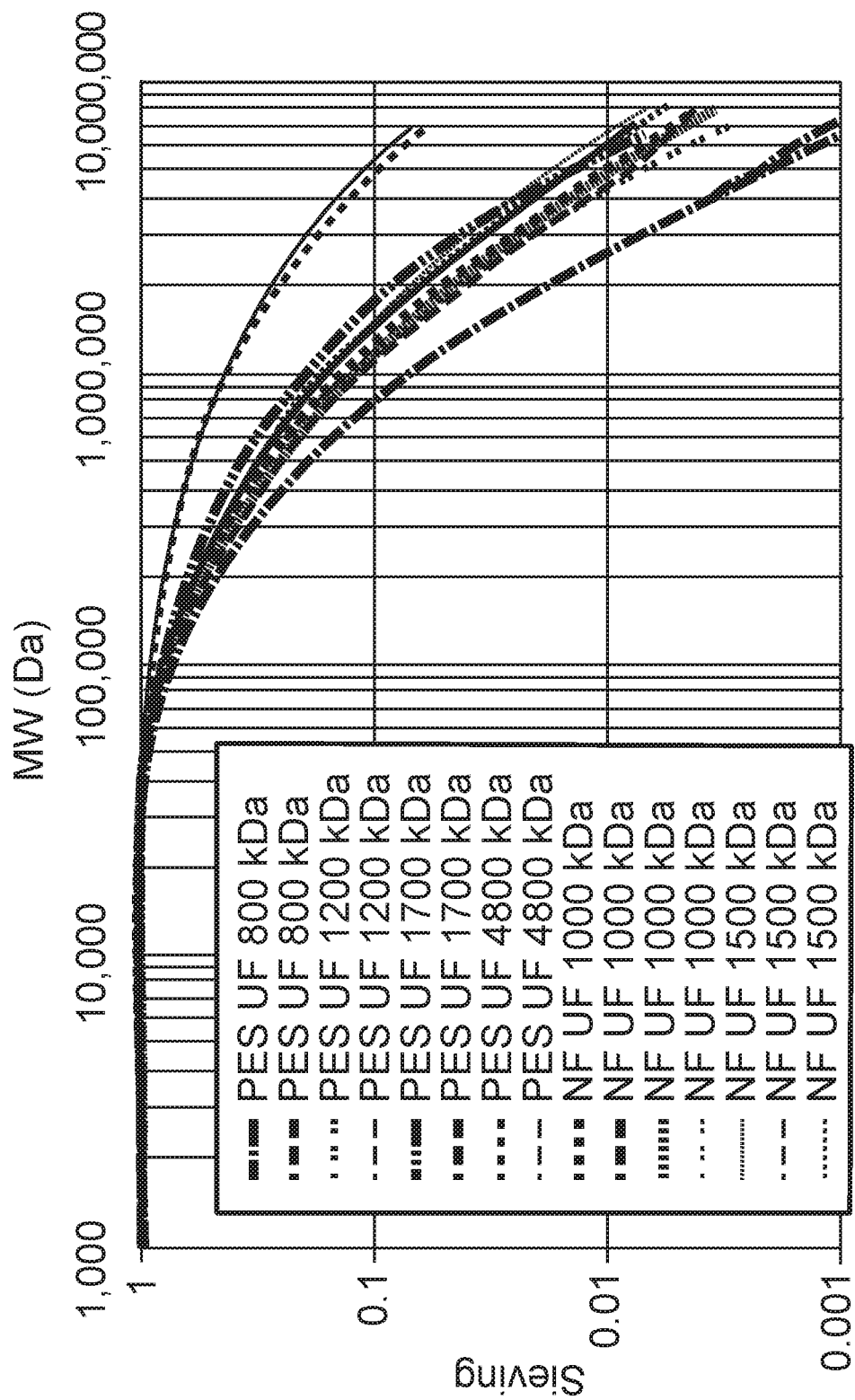
FIG. 5 is a graph depicting the Dextran sieving curves for duplicate samples of PES UF membrane with Dextran R90 values of 800, 1200, 1700, and 4800 kDa and four samples of the NF UF membrane with Dextran R90 values of 1000 kDa and three samples at 1500 kDa, as shown in the figure key. The plot is a $\log_{10}$ versus $\log_{10}$, where the x-axis is Dextran molecular weight in the unit Daltons (Da) and the y-axis is the Dextran sieving $\text{Log}_{10}$ scale from 0.001-1, obtained from comparing the membrane sample permeate gel permeation chromatogram relative to the feed gel permeation chromatography (GPC) of the initial challenge solution on the membrane retentate side.

In this experiment, Dextran rejection measurements are used to determine Dextran R90 cutoffs for the NF UF and PES UF membranes, as shown in FIG. 5. NF UF samples included Dextran R90 cutoffs of 1000 and 1500 kDa. Four different PES UF membrane samples have Dextran R90 cutoffs of 800, 1200, 1700 and 4800 kDa. The four PES UF membranes are common in the industry for the ultrafiltration of macromolecules and demonstrate similar Dextran retention curves to those of the NF UF membrane samples, as shown in FIG. 5. FIG. 5 shows that four samples of the electrospun Nylon-6 NF UF membrane with Dextran sieving R90 cutoffs of 1000 kDa have similar Dextran sieving curves on both the x and y-axis and in terms of slope relative to duplicate samples of the PES UF membrane with a Dextran sieving R90 cutoff of 1200 kDa.

Figure 6:
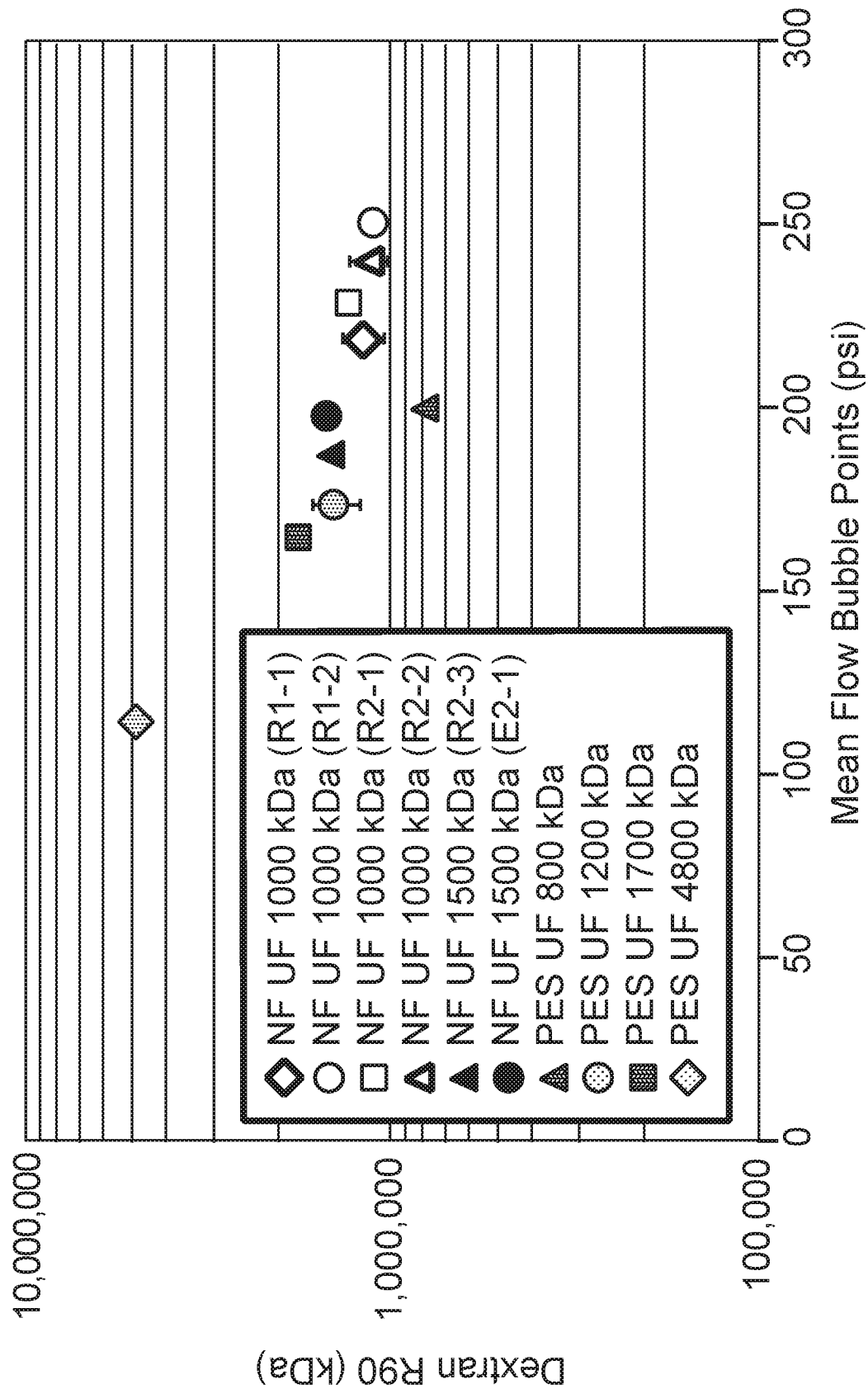
FIG. 6 is a graph depicting the average Dextran sieving R90 in kiloDaltons (kDa) on $\log_{10}$ scale (y-axis) versus mean flow bubble point in psi (on x-axis) for six samples of the NF UF membrane and four different PES UF membrane samples. The six NF UF membrane samples are: NF UF 1000 kDa (R1-1); (R1-2); (R2-1); (R2-2) and NF UF 1500 kDa (R2-3); and (E2-1), as shown in the figure key. The four PES UF membrane samples are: PES UF 800 kDa; 1200 kDa; 1700 kDa; and 4800 kDa, as shown in the figure key. The numbers before the unit kDa (kiloDaltons) indicates the membranes Dextran sieving R90 cutoffs from FIG. 5.
Figure 7:
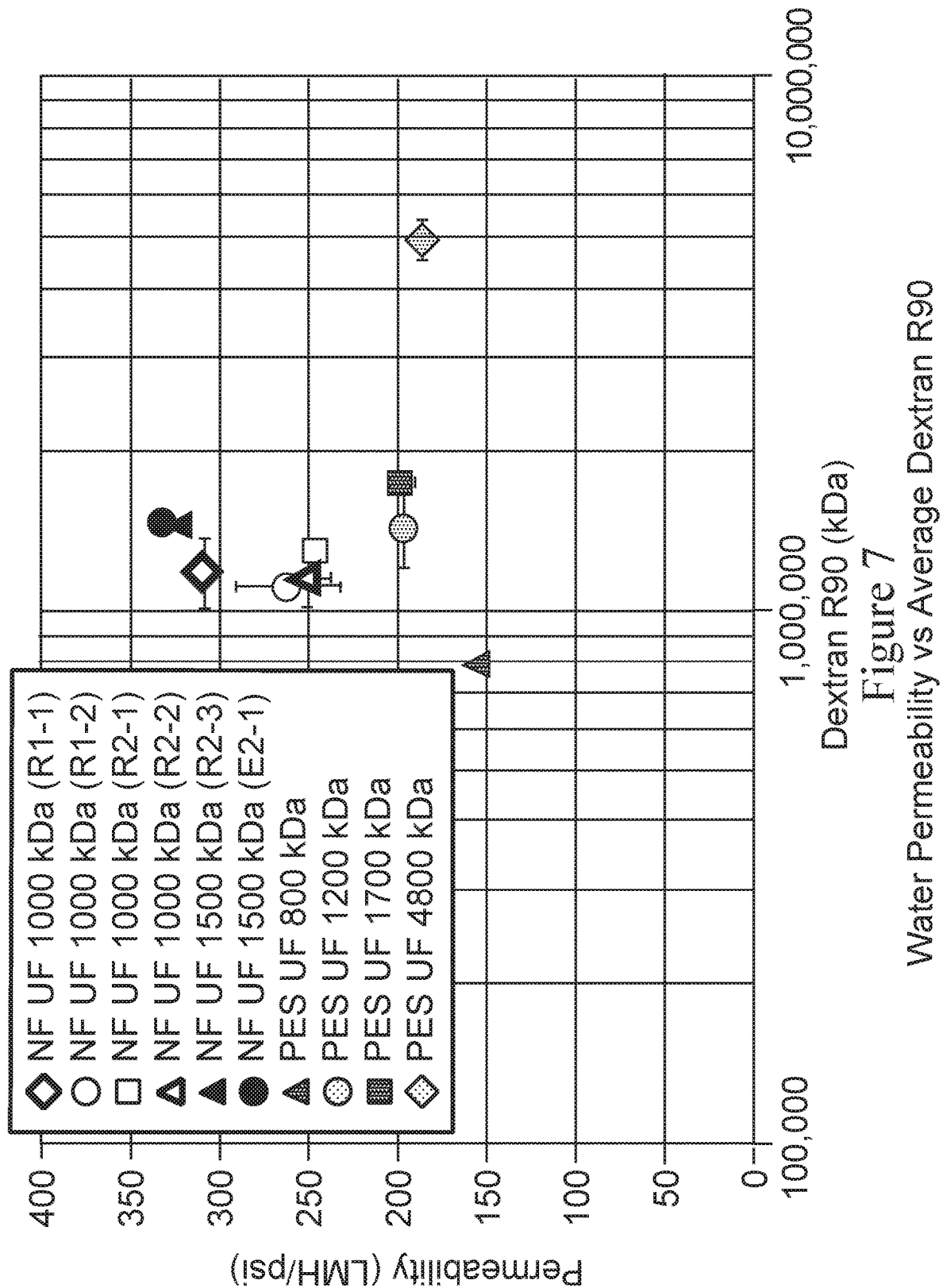
FIG. 7 is a graph depicting the average water permeability in LMH/psi (y-axis) versus average Dextran sieving R90 in kiloDaltons (kDa) on $\log_{10}$ scale (on x-axis) for six samples of the NF UF membrane and four different PES UF membrane samples. The six NF UF membrane samples are: NF UF 1000 kDa (R1-1); (R1-2); (R2-1); (R2-2) and NF UF 1500 kDa (R2-3); (E2-1), as shown in the figure key. The four PES UF membrane samples are the PES UF 800 kDa; 1200 kDa; 1700 kDa; and 4800 kDa, as shown in the figure key. The numbers before the unit kDa (kiloDaltons) indicate the membranes Dextran sieving R90 cutoffs from FIG. 5.

NF UF membranes are similar in Dextran R90 and mean flow bubble point to the PES UF membranes, as demonstrated in FIG. 6 and show higher water permeability at similar Dextran R90, as shown in FIG. 7.

FIG. 6 shows that four samples of the electrospun Nylon-6 NF UF membrane samples with Dextran sieving R90 cutoffs of 1000 kDa have lower Dextran sieving R90 cutoffs and higher mean flow bubble points than the PES UF membrane samples with a Dextran sieving R90 cutoff of 1200 kDa. The Electrospun Nylon-6 Nanofiber Ultrafiltration membrane (NF UF) has smaller average pore size that provides higher bubble points and lower Dextran sieving R90 cutoffs.

FIG. 7 shows that four samples of the Electrospun Nylon-6 NF UF membrane samples with Dextran sieving R90 cutoffs of 1000 kDa have greater water permeability and lower Dextran sieving R90 than the PES UF membrane samples with a higher Dextran sieving R90 cutoff of 1200 kDa.

Dextran molecular weight sieving measurements of the NF UF and PES UF membranes are made using a custom Dextran retention test. All membrane samples are prepared in Stirred Cells and pre-flushed as described in Example 3-2. Analytical size-exclusion chromatography of the feed and permeate samples is used to generate the MW rejection and sieving curves from which the Dextran R90 cutoff is determined for each membrane.

A mixed Dextran feed of 0.75% w/w Dextrans in pH 7.0 50 mM phosphate buffer is used to challenge the NF UF or PES UF membranes. Dextrans are purchased from Pharmacosmos A/S (Roervangsvej 30, DK-4300, Holbaek, Denmark). The average molecular weights (Mw) of the Dextrans used are as follows: 1,000 Da (Dextran T1, 5510 0001 4000); 3,500 Da (Dextran T3.5, 5510 0003 4007); 10,000 Da (Dextran T10, 5510 0010 4007); 40,000 Da (Dextran T40, 5510 0040 4007); 70,000 Da (Dextran T70, 5510 0070 4007); 500,000 Da (Dextran T500, 5510 0500 4006); and 2,000,000 Da (Dextran T2000, 5510 2000 4007).

40 mL of the mixed Dextran feed is poured into the Stirred Cell. A standard magnetic stir bar is placed in the cell and set to stir on a magnetic stir plate at 320 RPM. PVC tubing 1/16" ID (Fisher scientific catalog no. 14-190-118) attached to a peristaltic pump is connected to the permeate side to draw liquid at constant flow rate of 0.22 mL/min. Under constant Flux of 10 LMH, the first 2 to 3 ml is discarded, then re-circulated for about one hour to allow equilibration, and a permeate sample is collected for further analysis using gel permeation chromatography (GPC).

Analytical size-exclusion chromatography of Dextrans is performed with a Waters 2695 separation module and a Waters 2414 refractive index detector using a Phenomenex Shodex OH pak 13 μm SB-806 M HQ gel filtration column (part number: SB-806MHQ, column size: 300×8 mm, Phenomenex Inc., Torrance, Calif.). The isocratic mobile phase is composed of 50 mM potassium phosphate at pH 7.0 with 10 mg/L of sodium azide. The column is run at a flow rate of 1.0 mL/min for 20 min at a temperature of 35° C.

Molecular weight Dextran standards used to calibrate molecular weight from retention time are purchased from Sigma-Aldrich (St. Louis, Mo.), Glucose, MW=180 Da (#158968), Maltoheptaose, MW=1,153 Da (#284017) and American Polymer Standards (Mentor, Ohio) Dextrans: $M_p$=2,800 Da (DXT3K), $M_p$=6,300 Da (DXT7K), $M_p$=20,500 Da (DXT25K), $M_p$=43,000 Da (DXT47K), $M_p$=85,000 Da (DXT97K), $M_p$=245,000 Da (DXT325K), $M_p$=350,000 Da (DXT550K), $M_p$=1,465,000 Da (DXT2100K), $M_p$=6,300,000 Da (DXT5900K), and $M_p$=9,110,000 Da (DXT 8035K), where $M_p$ is the mean peak molecular weight.

Example 4: TFF (UF/DF) Membrane Application Comparison Using Custom Feeds

The Nanofiber UF with a R90=1000 kDa and PES UF membrane with a R90=1200 kDa are chosen for the membrane comparison in TFF (UF/DF) modes using custom Dextran feeds summarized in Table 1 below. The aforementioned membranes are designated NF UF and PES UF and have the physical properties which are demonstrated in FIGS. 4-7.

The electrospun NF UF membrane has an equivalent or improved performance to the solution immersion cast PES UF membrane in Tangential Flow Filtration (TFF) mode. Both ultrafiltration and diafiltration modes for Dextran concentration and low molecular weight clearance showed the Nanofiber membrane behaves like an ultrafiltration membrane with respect to yield, selectivity, and filtration flux, as summarized in Table 1.

TABLE 1

| Example # | Model Feed Membrane | Water | | Feed A (0.0385% w/w) | | Feed B (0.844% w/w) | | Feed C (8.44% w/w) | |
|---|---|---|---|---|---|---|---|---|---|
| | | NF UF | PES UF | NF UF | PES UF | NF UF | PES UF | NF UF | PES UF |
| 5, 6, 7 | Transport & Selectivity | TMP = 3 psi | | TMP = 0.25-7 psi | | TMP = 3-20 psi | | TMP = 3-20 psi | |
| 3-2 | Water Permeability | NF UF > PES UF | | N/A | | N/A | | N/A | |
| 5 | Flux vs TMP | N/A | | NF UF > PES UF | | NF UF > PES UF | | NF UF > PES UF | |
| 6 | Mass Transport vs TMP | | | NF UF > PES UF | | NF UF > PES UF | | NF UF > PES UF | |
| 7 | Selectivity vs Flux | | | NF UF ≅ PES UF | | NF UF ≅ PES UF | | NF UF ≅ PES UF | |
| 8 | Diafiltration | N/A | | 1.) 30 LMH @ 640 RPM 2.) 60 LMH @ 320 RPM | | N/A | | N/A | |
| 8 | Yield | N/A | | NF UF ≅ PES UF | | N/A | | N/A | |
| 8 | Selectivity | N/A | | NF UF ≅ PES UF | | N/A | | N/A | |

TABLE 1-continued

| Model Feed | | Water | | Feed A (0.0385% w/w) | | Feed B (0.844% w/w) | | Feed C (8.44% w/w) | |
|---|---|---|---|---|---|---|---|---|---|
| Example # | Membrane | NF UF | PES UF | NF UF | PES UF | NF UF | PES UF | NF UF | PES UF |
| 9 | Ultrafiltration | | N/A | 1.) 0.5 psi @ 600 RPM Concentrate 2, 4, and 8x | | 1.) 5 psi @ 600 RPM 2.) 7 psi @ 600 RPM Concentrate 2, 4, 8x | | 1.) 5 psi @ 300 RPM 2.) 7 psi @ 300 RPM Concentrate 2 and 3x | |
| 9 | Yield | | N/A | NF UF ≅ PES UF | | NF UF ≅ PES UF | | NF UF ≅ PES UF | |
| 9 | Selectivity | | N/A | NF UF ≅ PES UF | | NF UF ≅ PES UF | | NF UF ≅ PES UF | |
| 9 | Flux | | N/A | NF UF > PES UF | | NF UF > PES UF | | NF UF > PES UF | |

The membranes are examined side-by-side in duplicate in TFF mode for transport and selectivity, diafiltration and ultrafiltration. Table 1 and the remaining examples summarize the experimental comparison. The transport and selectivity are measured by Flux versus TMP, Mass Transport versus TMP and Selectivity versus Flux by sampling retentates and permeates through the Flux versus TMP experiment.

Three custom Dextran feeds are prepared for the NF UF and PES UF TFF (UF/DF) membrane evaluations in order to simulate the concentration and separation steps used in the conjugated polysaccharide vaccine industry.

The Dextrans used are commercially available from Pharmacosmos A/S (Roervangsvej 30, DK-4300, Holbaek, Denmark): 2,000,000 Da Dextran (T2000, 5510 2000 9007) and 110,000 Da Dextran (T110, 5510 0110 9006) with weight average molecular weights ($M_w$) of 1,950,000 and 112,000 Da. The three feeds A, B, and C covering 3 orders of magnitude are: 0.0385; 0.844; and 8.44% w/w total Dextran mass percent in pH 7.0 50 mM phosphate buffer, as shown in Table 2. Table 2 details the mass % of each Pharmacosmos stock number, mass ratios, and viscosity at 20° C.

TABLE 2

Summary of TFF (UF/DF) membrane application comparison

| Feed | Total Dextran (% w/w) | μ, 20° C. (cP) | Mass Ratio (T2000:T110) | T2000 (% w/w) | T110 (% w/w) |
|---|---|---|---|---|---|
| A | 0.0385 | 3.1 | 10:1 | 0.0350 | 0.0035 |
| B | 0.844 | 4.5 | 18:1 | 0.800 | 0.044 |
| C | 8.44 | 27.4 | 18:1 | 8.00 | 0.44 |

Figure 8:
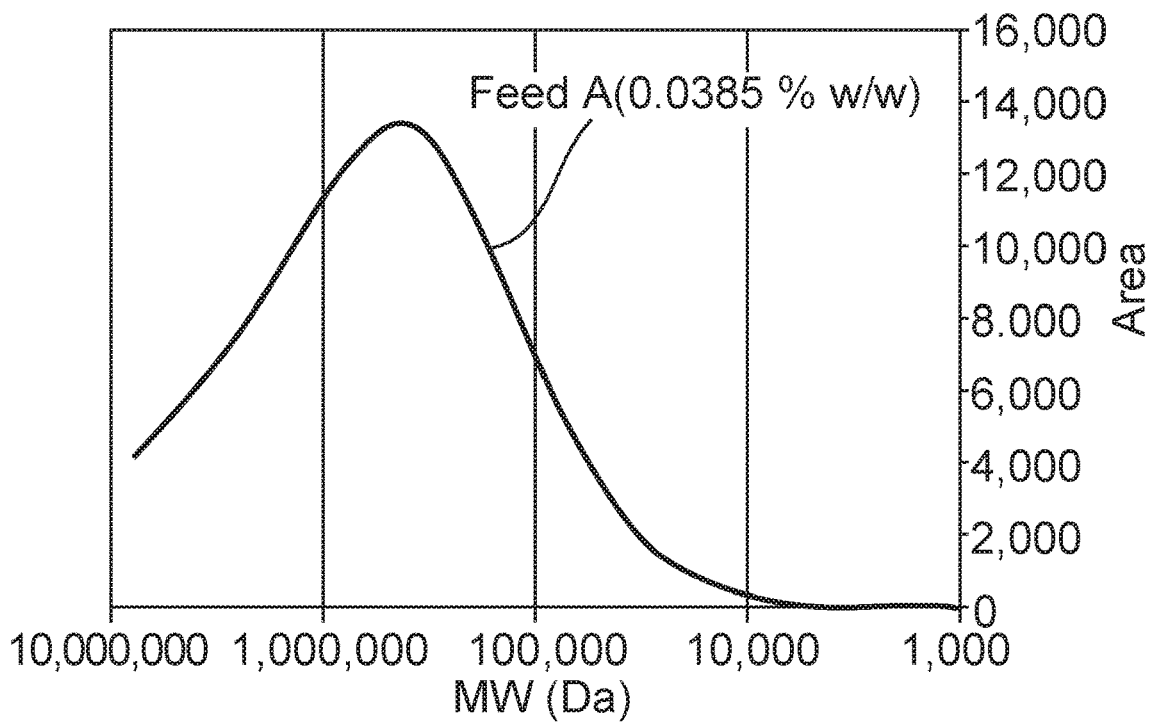
FIG. 8 is a gel permeation chromatogram of Feed A (0.0385% w/w) at pH 7.0, 50 mM phosphate buffer from Example 4. The x-axis is Dextran molecular weight in Daltons (Da) on a lop) scale. The area on the y-axis translates from refractive index detector response in milliVolts after integration with the GPC molecular weight standards.
Figure 9:
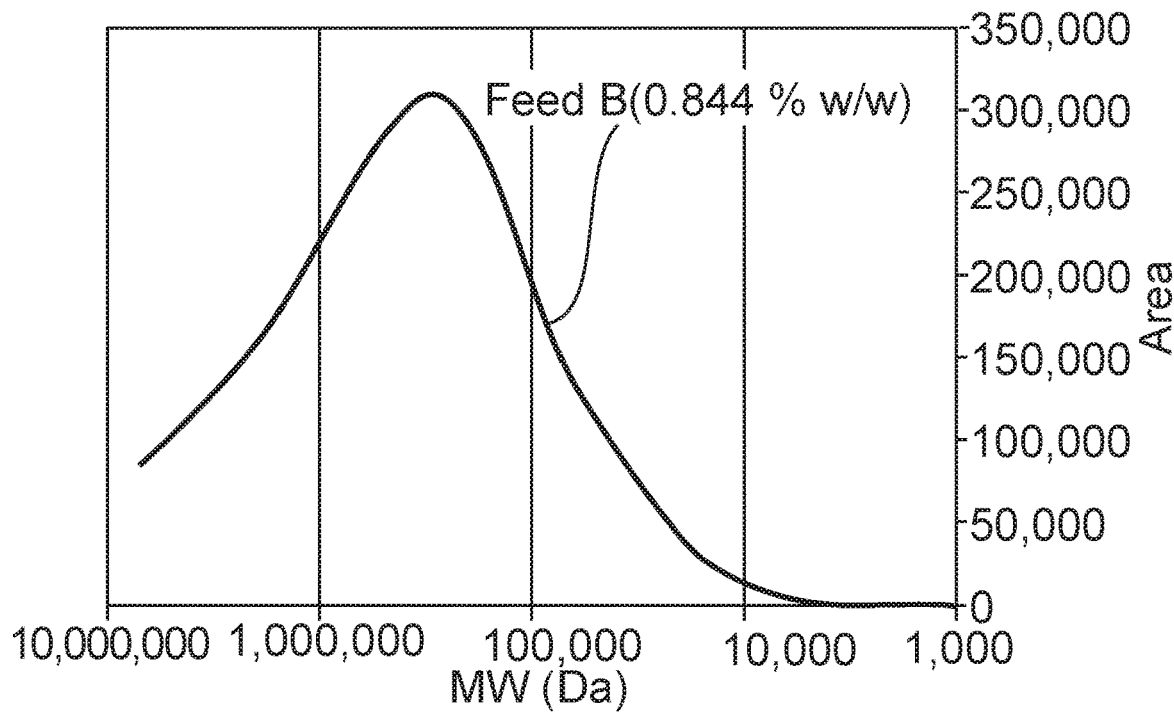
FIG. 9 is a gel permeation chromatogram of Feed B (0.844% w/w) at pH 7.0, 50 mM phosphate buffer from Example 4. The x-axis is Dextran molecular weight in Daltons (Da) on a $\log_{10}$ scale. The area on the y-axis translates from refractive index detector response in milliVolts after integration with the GPC molecular weight standards.

The three feeds have very polydisperse molecular weight distributions ranging by 3 orders of magnitude from 10,000 to 10,000,000 Da, as can be seen in the gel permeation chromatograms of Feed A, as shown in FIG. 8, using 0.0385% w/w Dextrans and gel permeation chromatograms of Feeds B and C, as shown in FIG. 9, using 0.844% and 8.44% w/w Dextrans, where Feed C is 10× Feed B or results in a chromatogram as shown in FIG. 9 when diluted 1:10 with buffer.

The three molecular weights 7,250,000 Da (D7250), 2,000,000 Da (D2000), and 110,000 Da (D110) are selected for the following comparative ultrafiltration and diafiltration Examples.

The chromatogram in FIG. 8 shows that Feed A has a very polydisperse molecular weight distribution covering 3 orders of magnitude from 10,000 to 10,000,000 Daltons. The percentages of the three molecular weights 7,250,000 Da (D7250), 2,000,000 Da (D2000), and 110,000 Da (D110) in Table 3 are from the peak areas of each MW over the total area.

The chromatogram in FIG. 9 shows that Feed B has very polydisperse molecular weight distribution covering 3 orders of magnitude from 10,000 to 10,000,000 Daltons. The percentages of the three molecular weights 7,250,000 Da (D7250), 2,000,000 Da (D2000), and 110,000 Da (D110) in Table 3 are from the peak areas of each MW over the total area. Feed C in Tables 2 and 3 is 10× Feed B or identical to FIG. 9 when diluted 1:10 with buffer.

Table 3 summarizes the actual peak height percentage of Dextrans with MW of 7,250,000 Da (D7250), 2,000,000 Da (D2000), and 110,000 Da (D110) in each of the three feeds. Based on the peak height percentage of 7,250,000 Da (D7250), 2,000,000 Da (D2000), and 110,000 Da (D110) in the feeds and the total Dextran mass percents of 0.0385, 0.844, and 8.44%, the actual percentage of D7250, D2000, and D110 are calculated, as summarized in Table 3.

TABLE 3

Custom Dextran Feeds

| Feed | Total Dextran (% w/w) | D7250 (%) | D2000 (%) | D110 (%) | Actual (% w/w) | | |
|---|---|---|---|---|---|---|---|
| | | | | | D7250 | D2000 | D110 |
| A | 0.0385 | 0.475 | 0.941 | 0.854 | $1.829 \times 10^{-4}$ | $3.623 \times 10^{-4}$ | $3.288 \times 10^{-4}$ |
| B | 0.844 | 0.402 | 0.768 | 1.046 | $3.393 \times 10^{-3}$ | $6.482 \times 10^{-3}$ | $8.828 \times 10^{-3}$ |
| C | 8.44 | | | | $3.393 \times 10^{-2}$ | $6.482 \times 10^{-2}$ | $8.828 \times 10^{-2}$ |

In the subsequent experiments, the concentrations, yields, and selectivity are all calculated based on the actual peak heights at each MW versus the feed chromatograms, as demonstrated by FIGS. 8 and 9 and based on the percentages in Table 3 for the three selected molecular weights under examination of D7250, D2000, and D110.

Samples are diluted as needed to remain on scale of the GPC refractive index detector and adjusted when needed for dilution. A dilution series of Feeds A and B are used to generate the concentration equations for D7250, D2000, and D110 in order to calculate the concentrations of each MW in the Ultrafiltration concentration experiments, as discussed in detail in Example 9.

Example 5. Measurement of Feed Flux Versus TMP

Figure 10:
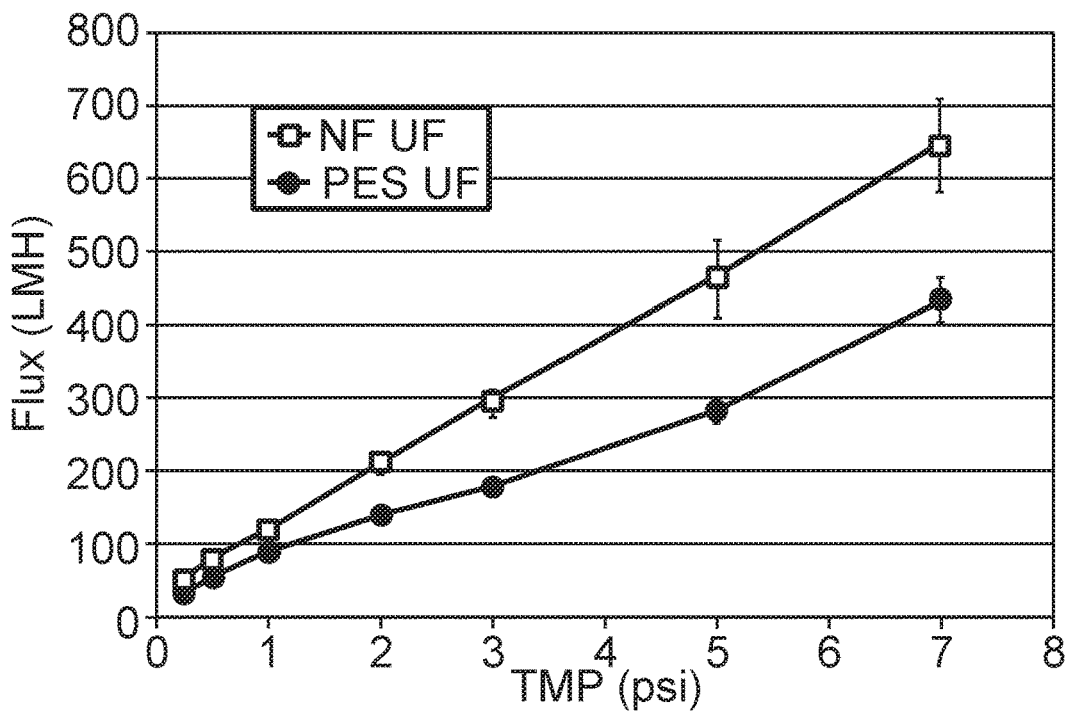
FIG. 10 is a graph depicting the average flux of Feed A in LMH (y-axis) versus trans-membrane pressure (TMP) in psi (x-axis) for duplicate samples of the NF UF membrane and PES UF membrane for Feed A from Example 5. The flux units are Liters of Feed A per square meter of membrane× hours (LMH) on the y-axis. Trans-membrane pressure (TMP) is pounds per square inch of pressure (psi) on the x-axis across the membrane.
Figure 11:
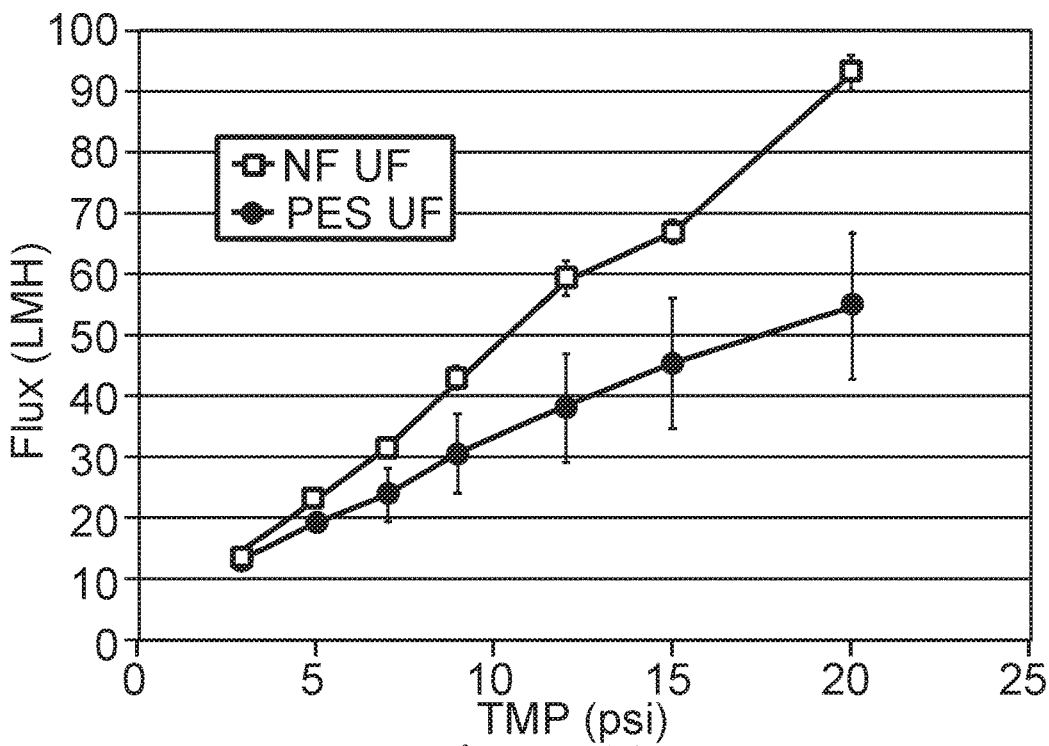
FIG. 11 is a graph depicting the average flux of Feed B in LMH (y-axis) versus trans-membrane pressure (TMP) in psi (x-axis) for duplicate samples of the NF UF membrane and PES UF membrane for Feed B from Example 5. The flux units are Liters of Feed B per square meter of membrane x hours (LMH) on the y-axis. Trans-membrane pressure (TMP) is pounds per square inch of pressure (psi) on the x-axis across the membrane.
Figure 12:
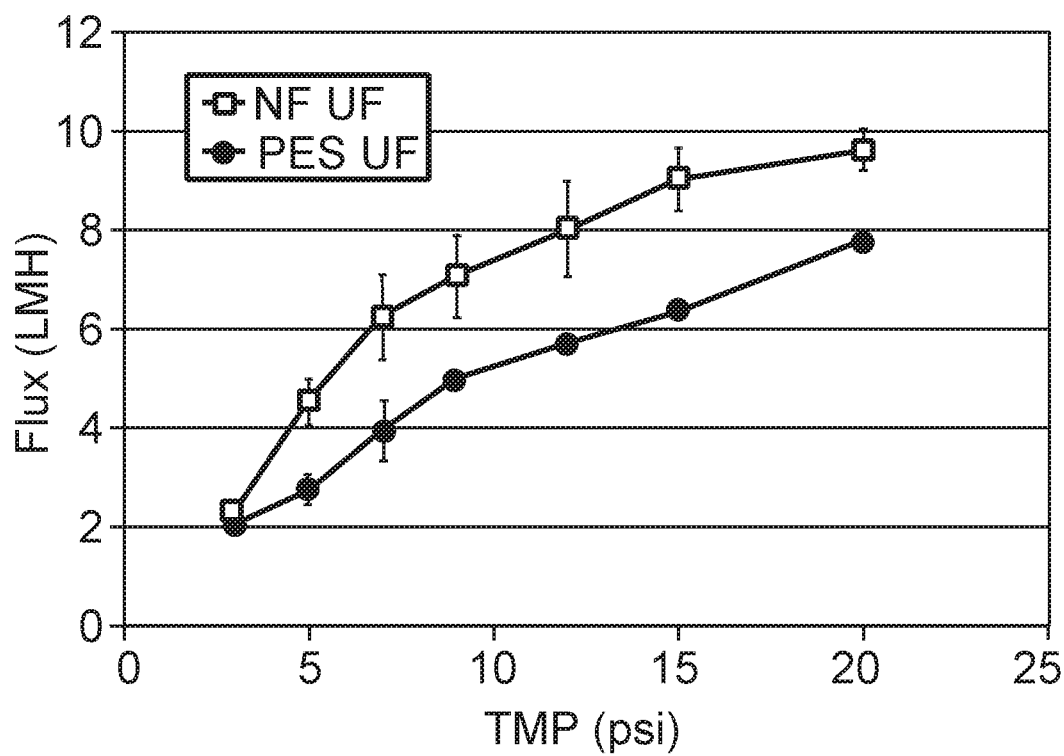
FIG. 12 is a graph depicting the average flux of Feed C in LMH (y-axis) versus trans-membrane pressure (TMP) in psi (x-axis) for duplicate samples of the NF UF membrane and PES UF membranes for Feed C from Example 5. The flux units are Liters of Feed C per square meter of membrane× hours (LMH) on the y-axis. Trans-membrane pressure (TMP) is pounds per square inch of pressure (psi) on the x-axis across the membrane.

Custom Dextran Feeds A, B, and C, demonstrated in Tables 2 and 3, are used to generate average flux versus trans-membrane pressure (TMP) curves. FIGS. 10, 11, and 12 for feeds A, B, and C, respectively, demonstrate that the NF UF membrane has higher average Dextran Feed flux versus TMP than the PES UF membrane having similar Dextran R90 cutoffs. The average flux for feeds A, B, and C cover three orders of magnitude in LMH, as shown in FIGS. 10, 11, 12, respectively, and there is mass transport polarization for the high concentration feed C in case of both the NF UF and PES UF membranes, as shown in FIG. 12.

The NF UF membrane had both higher average Dextran feed flux versus TMP, as demonstrated in FIGS. 10, 11 and 12 as well as higher water flux, as shown in FIG. 7.

Experiments are conducted in Stirred Cells as described in Example 3. Feeds are stirred at 320 RPM and pressurized using house air. Feed and permeate samples are collected at each pressure for GPC analysis.

FIG. 10 shows that the electrospun Nylon-6 NF UF membrane with a Dextran sieving R90 cutoff of 1000 kDa has greater Feed A Flux at the same TMP compared to the PES UF membrane with a higher Dextran sieving R90 cutoff of 1200 kDa.

FIG. 11 shows that the electrospun Nylon-6 NF UF membrane with a Dextran sieving R90 cutoff of 1000 kDa has greater Feed B Flux versus TMP than the PES UF membrane with a higher Dextran sieving R90 cutoff of 1200 kDa.

FIG. 12 shows that the electrospun Nylon-6 NF UF membrane with a Dextran sieving R90 cutoff of 1000 kDa has greater Feed C Flux versus TMP than the PES UF membrane with a higher Dextran sieving R90 cutoff of 1200 kDa.

Example 6. Measurement of Mass Transport Versus TMP

Figure 13:
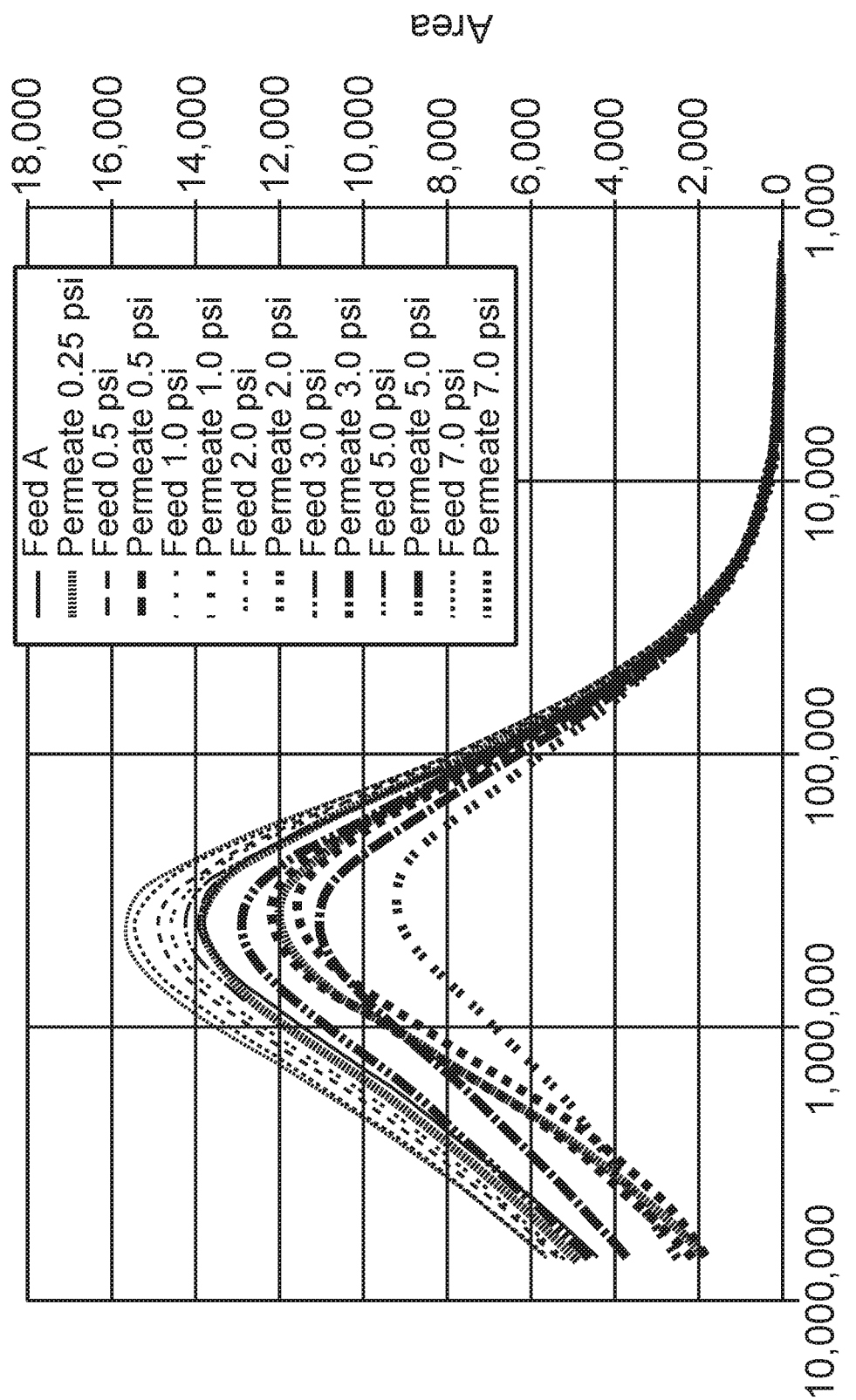
FIG. 13 depicts a gel permeation chromatograms of Feed A (0.0385% w/w) samples of feed and permeate collected from Example 5 at each TMP.
Figure 14:
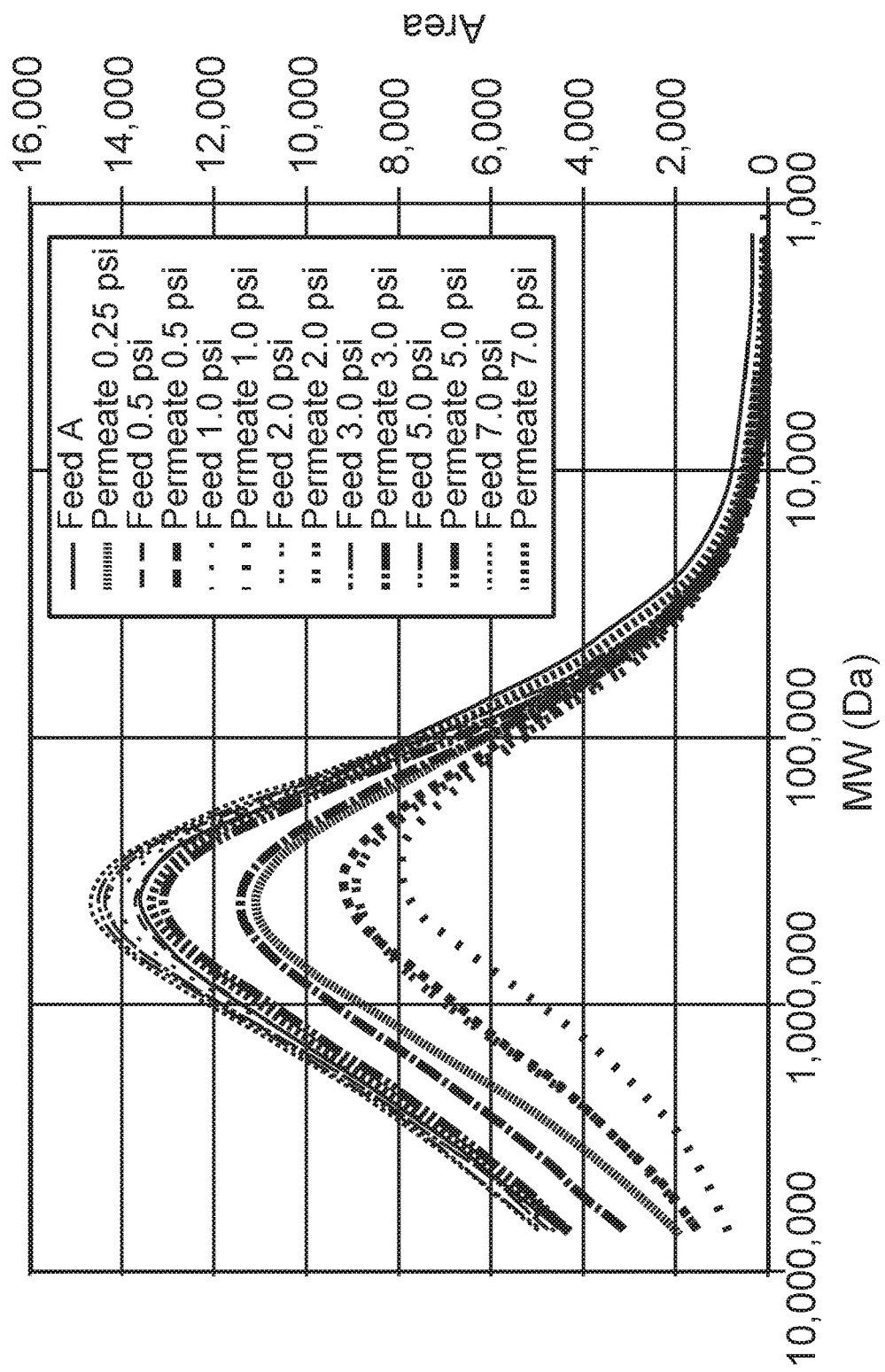
FIG. 14 depicts a gel permeation chromatograms of Feed A (0.0385% w/w) samples of feed and permeate collections during Example 5 at each TMP.

The Dextran mass/concentration transport is measured by collecting feed and permeate samples from Example 5 at each pressure for GPC analysis. FIGS. 13 and 14 demonstrate the gel permeation chromatograms of Feed A for one of the two samples of the NF UF and PES UF membrane samples. The transport of D7250, D2000, and D110 are determined by the ratio $C_P/C_F$ where $C_P$ and $C_F$ are the concentrations in the feed and permeate at each pressure.

FIGS. 13 and 14 demonstrate how the Feed A concentration slightly increases through the Flux versus TMP experiment.

In FIG. 13, the chromatograms overlay shows how the Feed A concentration in the permeate is initially higher and then decreases slightly before increasing again through the Flux versus TMP experiment, indicating that the membrane initially passes more of the D7250, D2000, and D110 before a surface concentration polarization equilibrium can form.

In FIG. 14, the chromatograms overlay show how the Feed A concentration in the permeate is initially higher and then slightly decreases before increasing again through the Flux versus TMP experiment, indicating the membrane initially passes more of the D7250, D2000, and D110 before a surface concentration polarization equilibrium can form.

Figure 15:
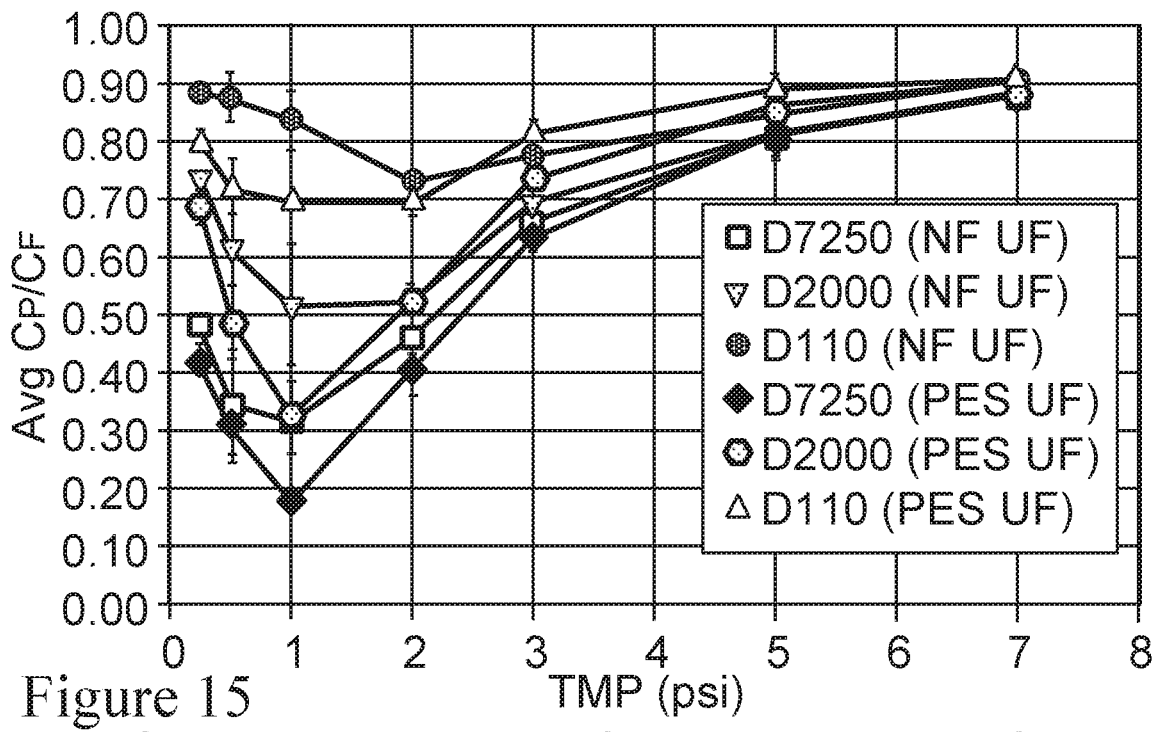
FIG. 15 is a graph depicting the mass/concentration transport or average $C_P/C_F$ of D7250, D2000, D110 on the y-axis for the NF UF and PES UF membranes using Feed A with the Flux versus TMP (psi) experiment from Example 5. Example 6 details how to obtain the Dextran mass/concentration transport from Example 5 by collecting feed and permeate samples at each TMP (psi) on the x-axis for GPC analysis.

In case of FIG. 15, the transport of D7250, D2000, and D110 is the ratio $C_P/C_F$, where $C_P$ and $C_F$ are the concentrations in the feed and permeate at each TMP (psi). FIG. 15 shows that the average mass/concentration transport for Dextrans in Feed A is greater versus TMP for the electrospun Nylon-6 NF UF relative to the PES UF membranes.

Figure 16:
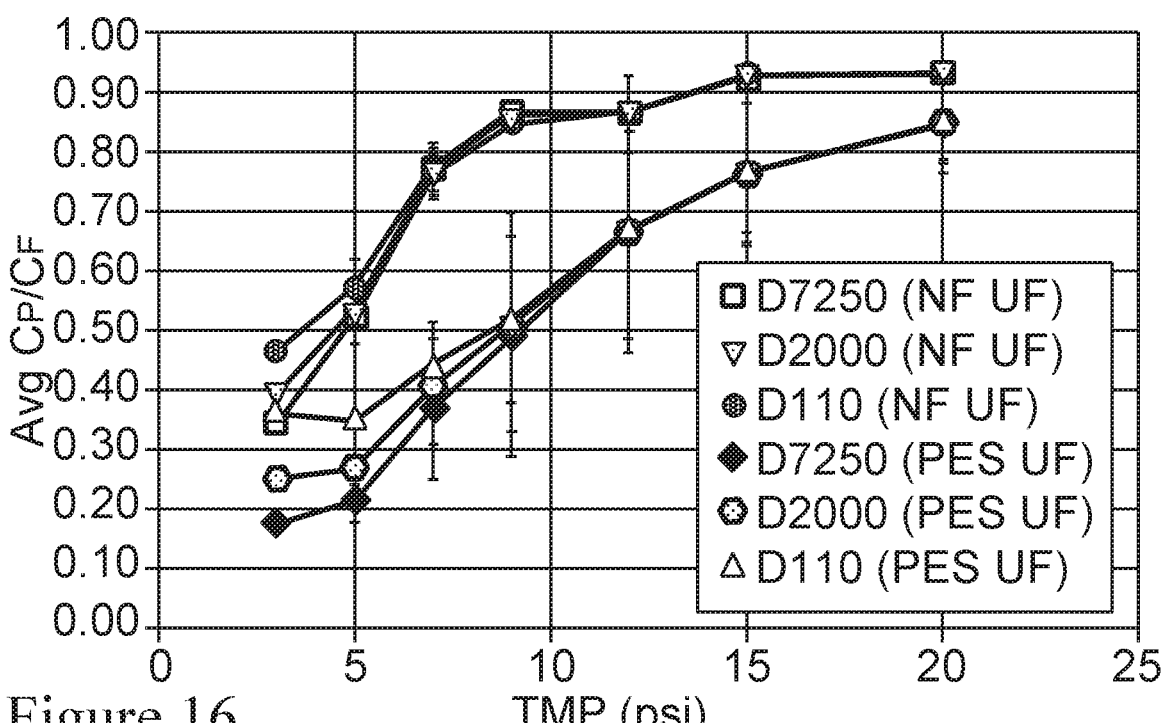
FIG. 16 is a graph depicting the mass/concentration transport or average $C_P/C_F$ of D7250, D2000, D110 on the y-axis for the NF UF and PES UF membranes using Feed B with the Flux versus TMP (psi) experiment from Example 5. As in case of FIG. 15, Example 6 details how to obtain the Dextran mass/concentration transport from Example 5 by collecting feed and permeate samples at each TMP (psi) on the x-axis for GPC analysis.

In case of FIG. 16, the transport of D7250, D2000, and D110 is the ratio $C_P/C_F$, where $C_P$ and $C_F$ are the concentrations in the feed and permeate at each TMP (psi). FIG. 16 shows that the average mass/concentration transport for Dextrans in Feed B is greater versus TMP for the electrospun Nylon-6 NF UF membrane than the PES UF membrane.

To summarize, as observed, the mass transport or concentration passage of Dextrans D7250, D2000, and D110 for the NF UF membrane (as shown in FIG. 13) is higher than for the PES UF membrane (as shown in FIG. 14). The average $C_P/C_F$ is calculated for Feed A and plotted versus the TMP (as shown in FIG. 15). Both the NF UF and PES UF membranes initially pass more of the D7250, D2000, and D110 before a surface concentration polarization equilibrium can form (as shown in FIGS. 13, 14, and 15). The average mass/concentration transport for Dextrans in Feed B is greater for the NF UF membrane relative to the PES UF membrane (as shown in FIG. 16).

Example 7. Measurement of Selectivity Versus Flux

The mass transport relationship $C_P/C_F$ from Example 6 for D7250, D2000, and D110 is used to generate a selectivity factor versus flux from the flux versus TMP data above. The selectivity factor is determined using the equation $[(C_P/C_F)_{D110}/(C_P/C_F)_{D2000\ or\ D7250}]$ in order to determine the average passage selectivity of D110/D2000 and D110/D7250 versus flux.

Figure 17:
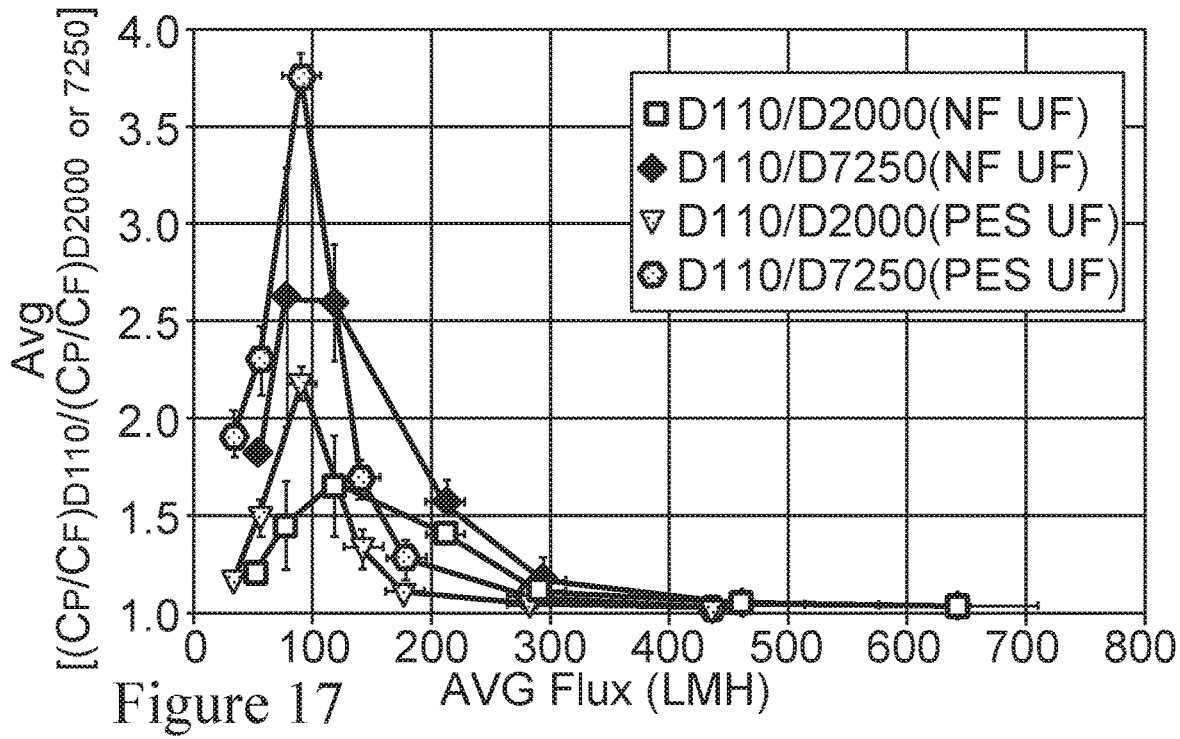
FIG. 17 is a graph depicting the average selectivity of D110/D2000 and D110/D7250 versus average flux in LMH for the NF UF and PES UF membranes using Feed A with the Flux versus TMP (psi) experiment from Examples 5 and 6. Example 7 details how to calculate the selectivity factor from the equation $[(C_P/C_F)_{D110}/(C_P/C_F)_{D2000 \text{ or } D7250}]$ on the y-axis to determine the average passage selectivity of D110/D2000 and D110/D7250 versus average flux (LMH) on the x-axis.
Figure 18:
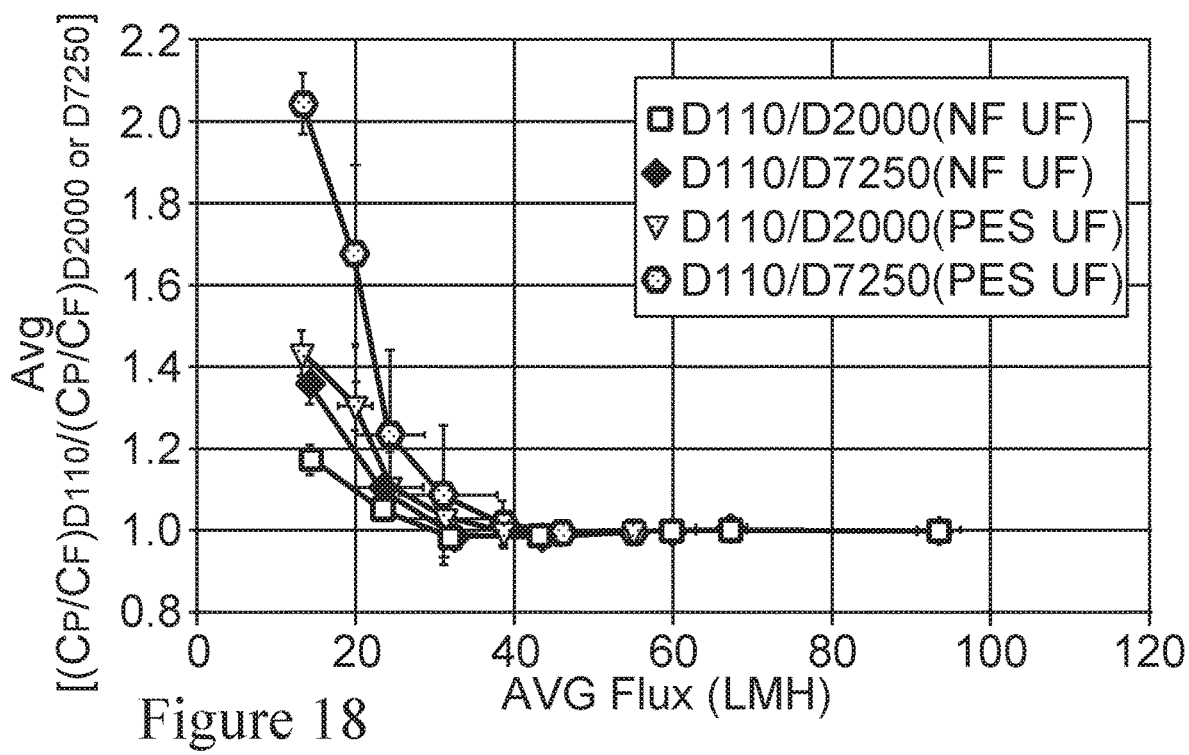
FIG. 18 is a graph depicting the average selectivity of D110/D2000 and D110/D7250 versus average flux in LMH for the NF UF and PES UF membranes using Feed B with the Flux versus TMP (psi) experiment from Examples 5 and 6. Example 7 details how to calculate the selectivity factor from the equation $[(C_P/C_F)_{D110}/(C_P/C_F)_{D2000 \text{ or } D7250}]$ on the y-axis to determine the average passage selectivity of D110/D2000 and D110/D7250 versus average flux (LMH) on the x-axis.

Average selectivity factor versus flux for the NF UF and PES UF membranes using Feeds A and B is shown in FIGS. 17 and 18 respectively. As observed, the PES UF membrane has higher selectivity factors than the NF UF membrane with increase in TMP/Flux, however, the average selectivity approaches 1 at similar flux for both the NF UF and PES UF membranes with Feeds A and B (as shown in FIGS. 17 and 18, respectively). Both membranes have their best selectivity at low constant flux. The hold-up volume of 0.5 mL in the 50 mL Stirred Cell causes some dilution and shift in the actual data versus TMP and flux.

FIG. 17 shows that the electrospun Nylon-6 NF UF and PES UF membranes have similar selectivities of D110/D2000 and D110/D7250 using Feed A versus average flux (LMH) and that both are greater than 1 and approach 1 at similar flux.

FIG. 18 shows that the electrospun Nylon-6 NF UF) and PES UF membranes have similar selectivities of D110/D2000 and D110/D7250 using Feed B versus average flux (LMH) and that both are greater than 1 and approach 1 at similar flux.

Example 8. Measurement of Diafiltration at Constant Flux

Two constant volume Diafiltration experiments in duplicate are conducted to compare the NF UF and PES UF membranes using Feed A. Stirred Cells with membrane samples are prepared, as described above. Peristaltic pumps with matching flow rates equivalent to 30 or 60 LMH (0.68 or 1.36 mL/min) are used to draw from the permeate and feed the retentate with buffer. Retentate and permeate samples are taken at each 40 mL diavolume for analysis by GPC. The 30 LMH experiment is stirred at 640 RPM and the 60 LMH at 320 RPM.

Figure 19:
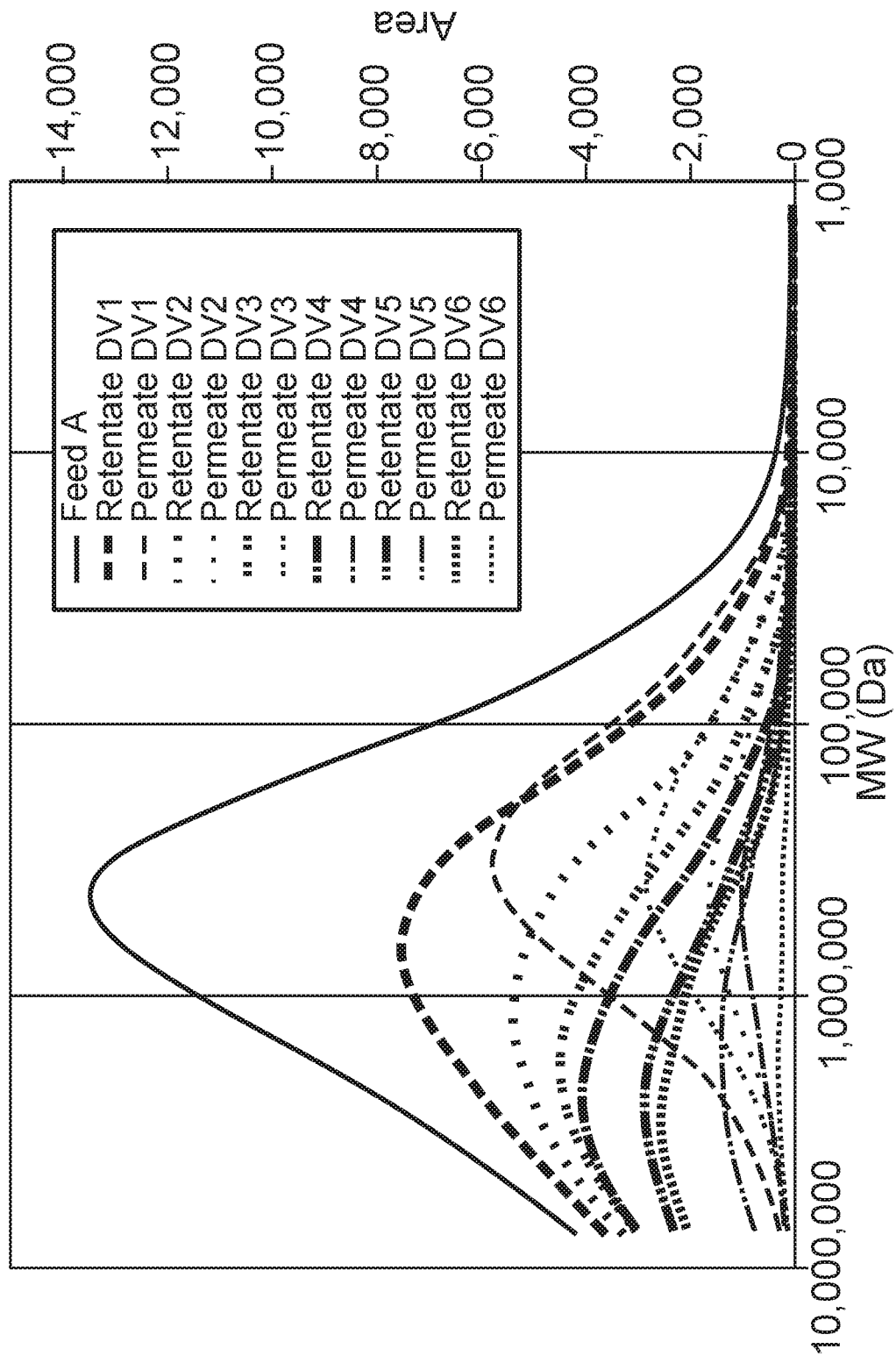
FIG. 19 depicts gel permeation chromatograms of the feed, retentates and permeates during Diafiltration of Feed A at 30 LMH and 640 RPM using the NF UF membrane. The x-axis is Dextran molecular weight in Daltons (Da) on a $\log_{10}$ scale. The area on the y-axis translates from refractive index detector response in milliVolts after integration with the GPC molecular weight standards.
Figure 20:
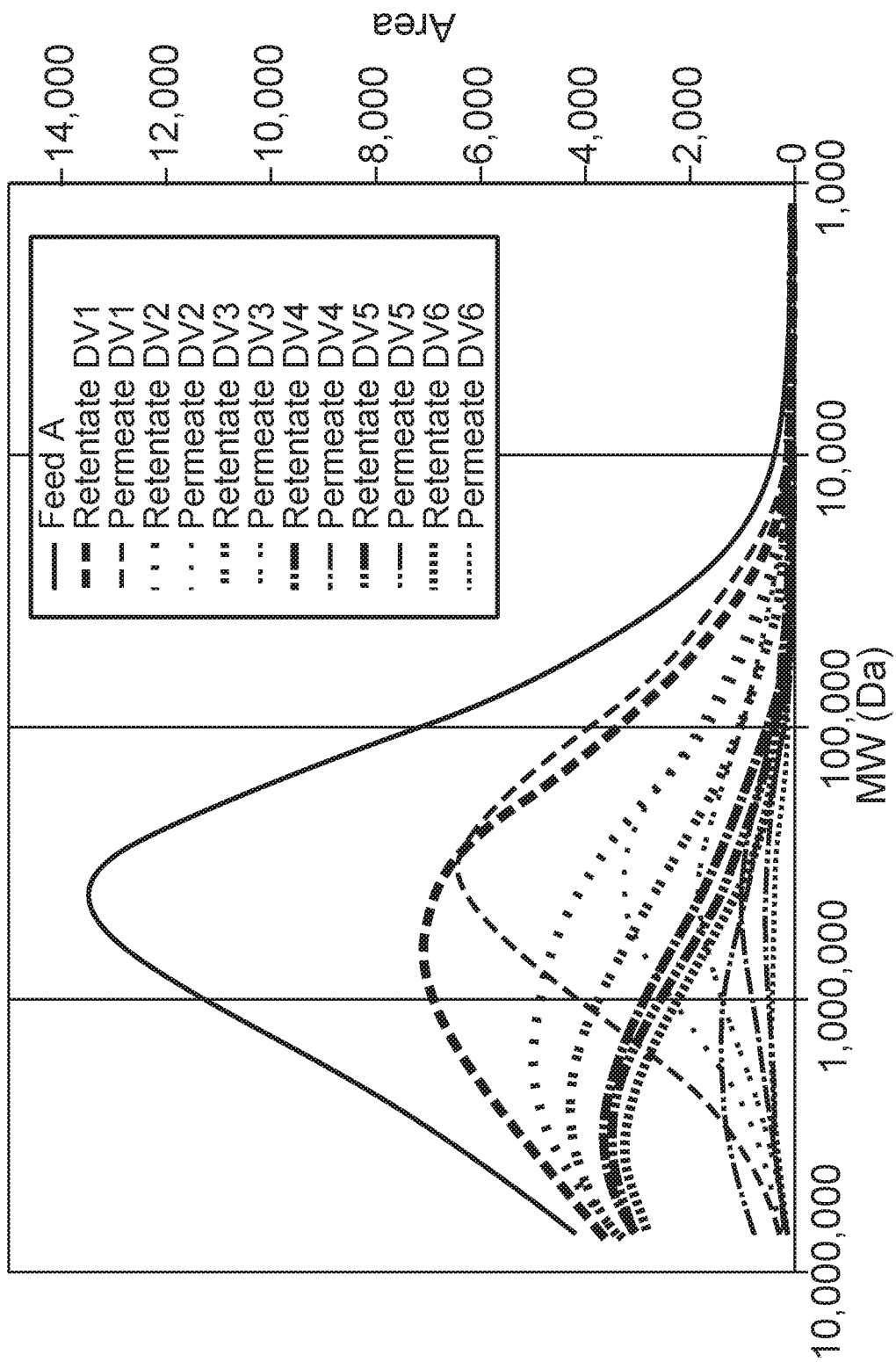
FIG. 20 depicts gel permeation chromatograms of the feed, retentates, and permeates during Diafiltration of Feed A at 30 LMH and 640 RPM using the PES UF membrane. The x-axis is Dextran molecular weight in Daltons (Da) on a $\log_{10}$ scale. The area on the y-axis translates from refractive index detector response in milliVolts after integration with the GPC molecular weight standards.

FIGS. 19 and 20 show the gel permeation chromatograms of the retentate and permeate samples at each diavolume from 1 to 6 for one of the duplicates for the NF UF and PES UF membrane samples from the 30 LMH and 640 RPM experimental run. Both the NF UF and PES UF membranes behave similarly in selectively retaining the higher MW Dextrans (D7250, D2000) and permeating the lower MW Dextrans (D110), as shown in FIGS. 21 and 22.

The chromatogram overlay in FIG. 19 shows how Feed A concentration is initially higher and then with the increasing diavolumes, the retentates MW distribution shifts to the left towards higher MW while the permeates shift to the right towards lower MW.

The chromatogram overlay in FIG. 20 shows how Feed A concentration is initially higher and then with increasing diavolumes, the retentates MW distribution shifts to the left towards higher MW while the permeates shift to the right towards lower MW.

Figure 21:
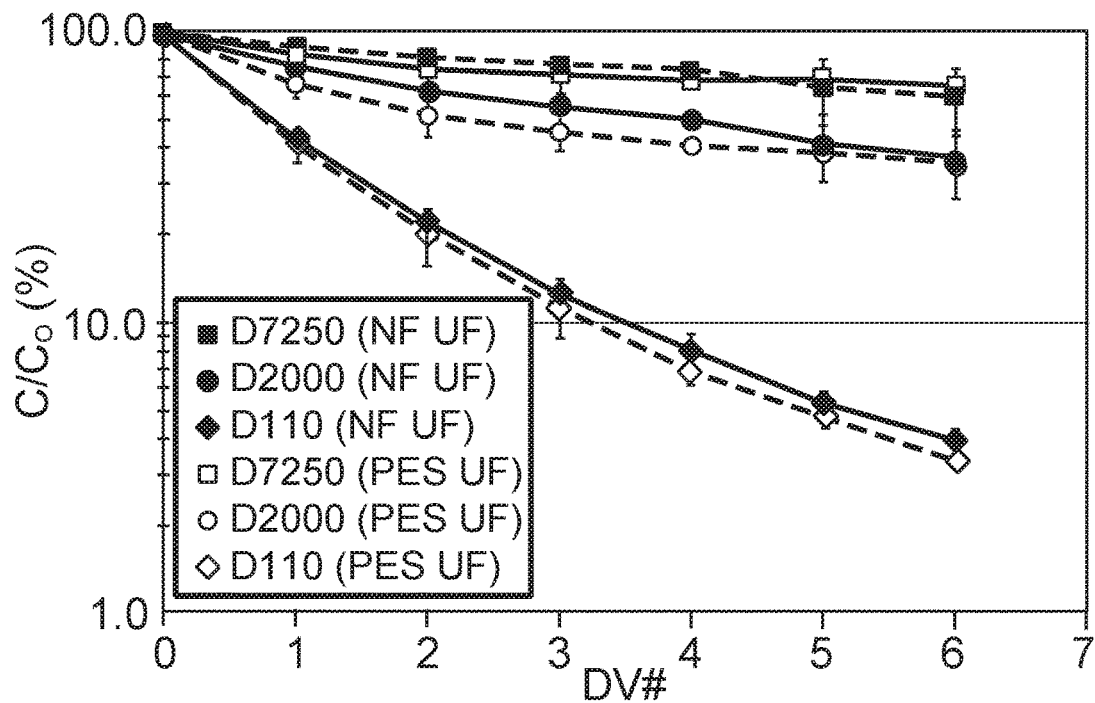
FIG. 21 is a graph depicting the average retentate $C/C_o$ of D7250, D2000, D110 on the y-axis versus diavolume number on the x-axis for the NF UF and PES UF membranes using Feed A from the Diafiltration experiment in Example 8. The diafiltration of Feed A is at a constant Flux of 30 LMH with stirring at 640 RPM.
Figure 22:
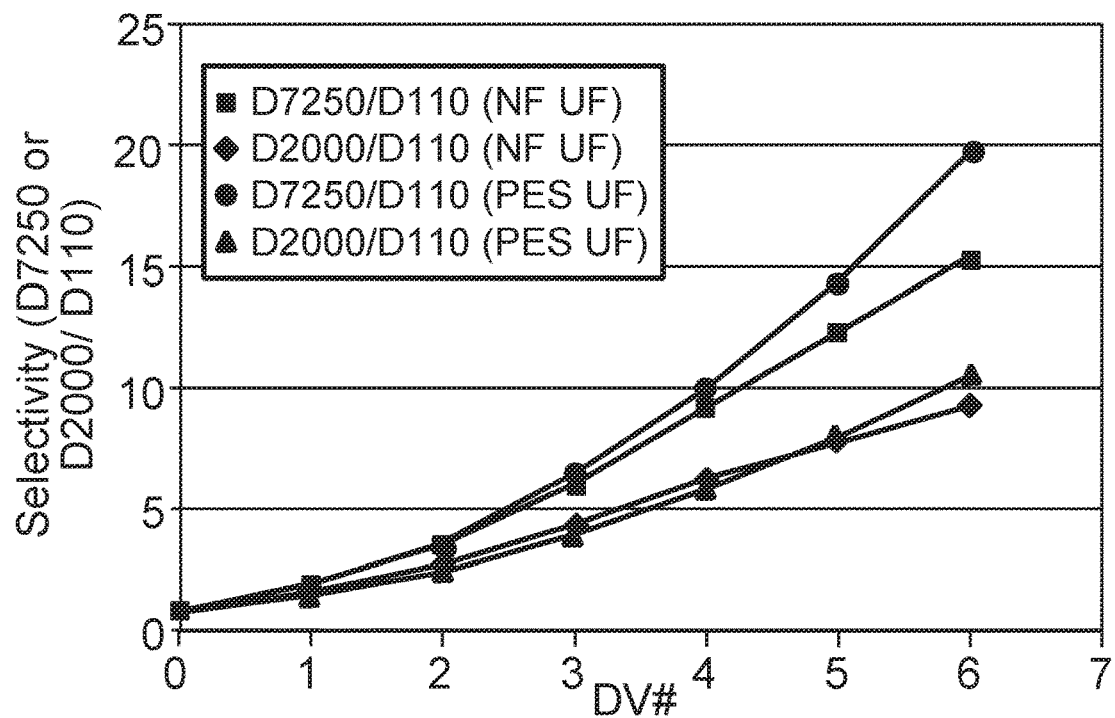
FIG. 22 is a graph depicting the average retentate selectivity D7250/D110 and D2000/D110 on the y-axis versus diavolume number on the x-axis for the NF UF and the PES UF membranes using Feed A from the Diafiltration experiment in Example 8. The diafiltration of Feed A is at a constant Flux of 30 LMH with stirring at 640 RPM. The average retentate selectivities are from the FIG. 21 values as D7250/D110=$(C/C_o)_{D7250}/(C/C_o)_{D110}$ and D2000/D110=$(C/C_o)_{D2000}/(C/C_o)_{D110}$.
Figure 23:
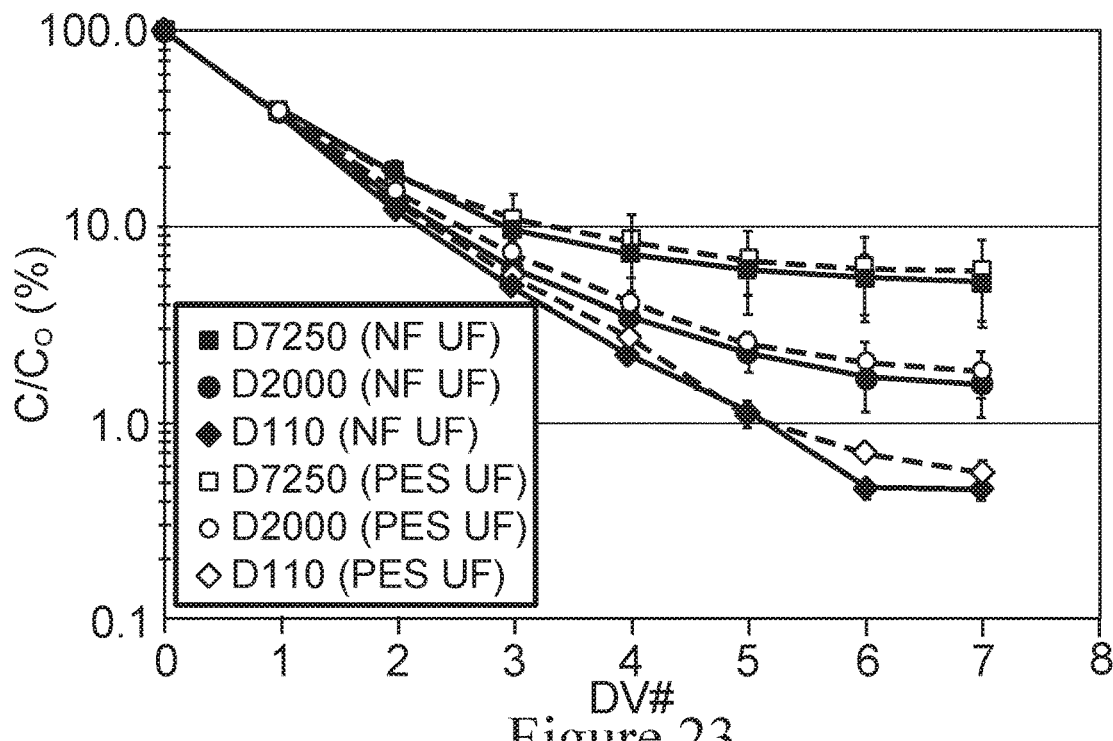
FIG. 23 is a graph depicting the average retentate $C/C_o$ of D7250, D2000, D110 on the y-axis versus diavolume number on the x-axis for the NF UF and the PES UF membranes using Feed A from the Diafiltration experiment in Example 8. The diafiltration of Feed A is at a constant Flux of 60 LMH and stirring at 320 RPM.

The average retentate $C/C_o$ versus diavolumes of Feed A is calculated for the Diafiltration at 30 LMH and 640 RPM (as shown in FIG. 21) and 60 LMH and 320 RPM (as shown in FIG. 23). Under both diafiltration conditions, the NF UF and PES UF membranes have similar average retention yields versus diavolumes for D7250, D2000, and D110 (as shown in FIGS. 21 and 23).

FIG. 21 shows that the NF UF and the PES UF membranes have similar average retention yields versus diavolumes for D7250, D2000, and D110.

FIG. 22 shows that the NF UF and the PES UF membranes have similar average retentate selectivity for D7250/D110 and D2000/D110 versus diavolume.

FIG. 23 shows that the NF UF and the PES UF membranes have similar average retention yields versus diavolumes for D7250, D2000, and D110. Both membranes have similar lower retention at higher flux and lower stirring, than observed in FIG. 21.

Figure 24:
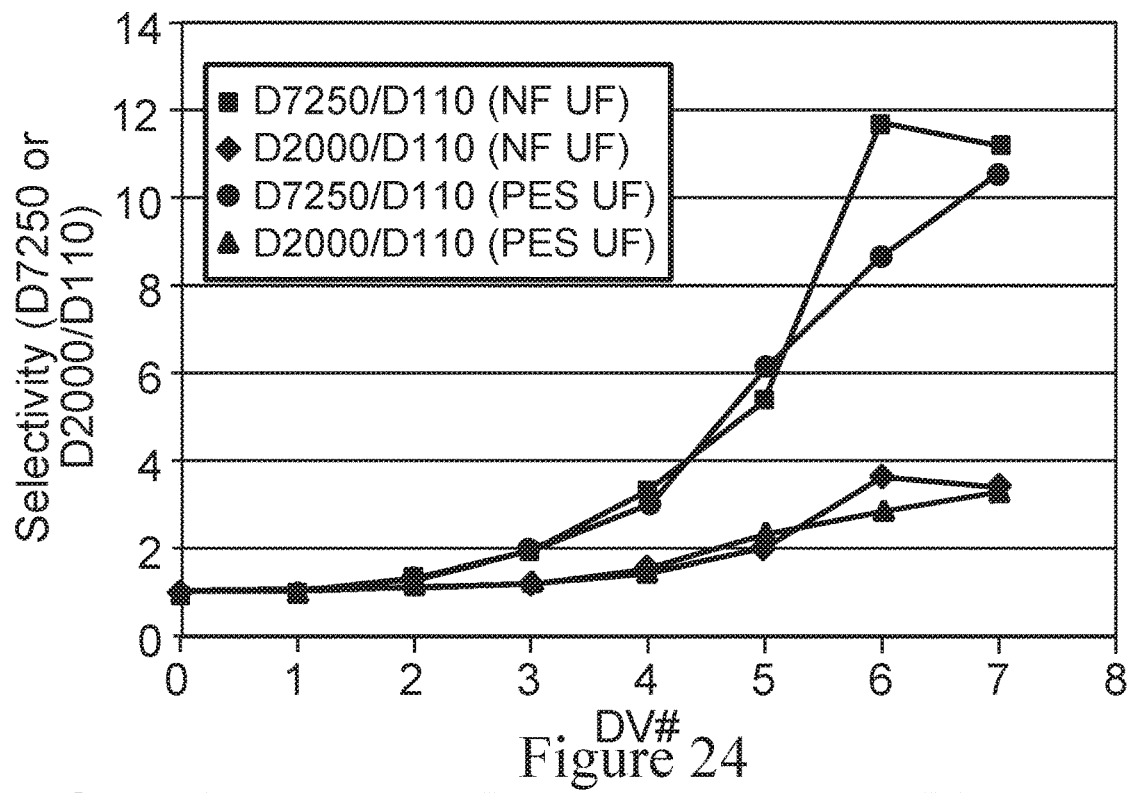
FIG. 24 is a graph depicting the average retentate selectivity of D7250/D110 and D2000/D110 on the y-axis versus diavolume number on the x-axis for the NF UF and the PES UF membranes using Feed A from the Diafiltration experiment in Example 8. The diafiltration of Feed A is at a constant Flux of 60 LMH and stirring at 320 RPM. The average retentate selectivities are from the FIG. 23 values as D7250/D110=$(C/C_o)_{D7250}/(C/C_o)_{D110}$ and D2000/D110=$(C/C_o)_{D2000}/(C/C_o)_{D110}$.

The average retentate selectivities for the NF UF and PES UF membranes in FIGS. 21 and 23 are calculated using $D7250/D110=(C/C_o)_{D7250}/(C/C_o)_{D110}$ and $D2000/D110=(C/C_o)_{D2000}/(C/C_o)_{D110}$ and plotted versus diavolumes (as shown in FIGS. 22 and 24).

FIG. 24 shows that the NF UF and the PES UF membranes have similar average retentate selectivity for D7250/D110 and D2000/D110 versus diavolume. Both membranes have similar lower average retentate selectivity at higher flux and lower stirring than observed in FIG. 22.

The average D7250/D110 and D2000/D110 are very similar for both the NF UF and PES UF membranes at both 30 LMH at 640 RPM and 60 LMH at 320 RPM. Both membranes have similar lower retention (as shown in FIG. 23) and selectivity (as shown in FIG. 24) at higher flux and lower stirring.

Example 9. Ultrafiltration at Constant TMP

Figure 25:
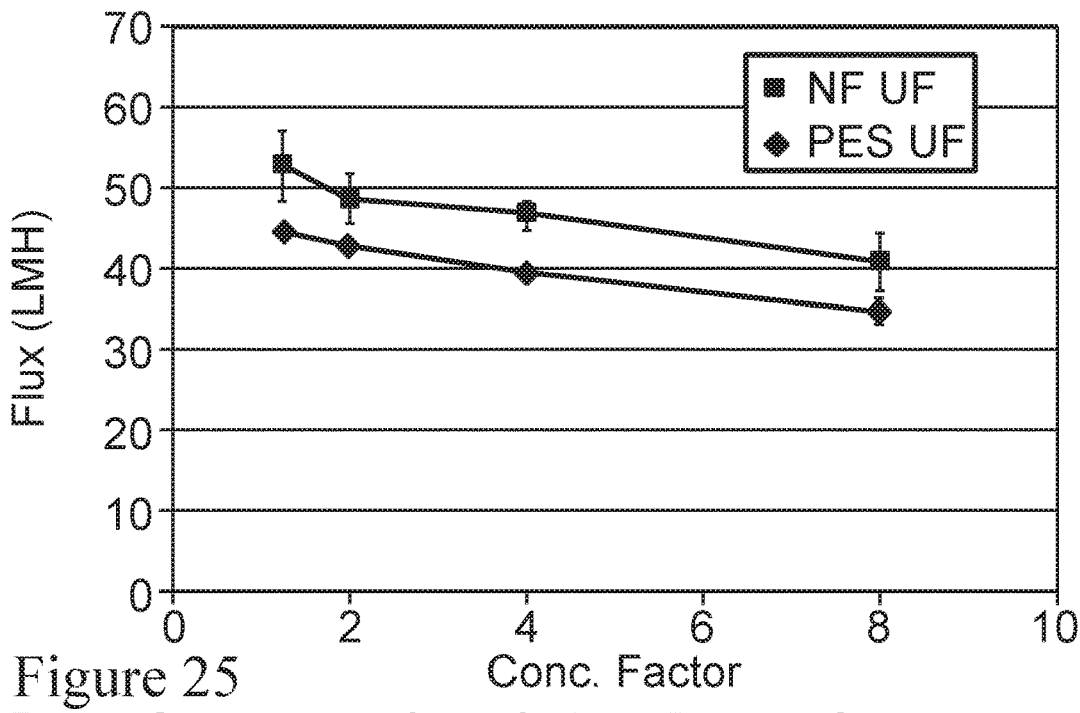
FIG. 25 is a graph depicting the average flux in LMH on the y-axis versus concentration factor on the x-axis during 2, 4, and 8× ultrafiltration concentration of Feed A for the NF UF and the PES UF membranes at 0.5 psi constant TMP and 600 RPM in Example 9. The flux units are Liters of Feed A per square meter of membrane×hours (LMH) on the y-axis. Permeate volume over time determines the flux and tracks concentration factors.
Figure 26:
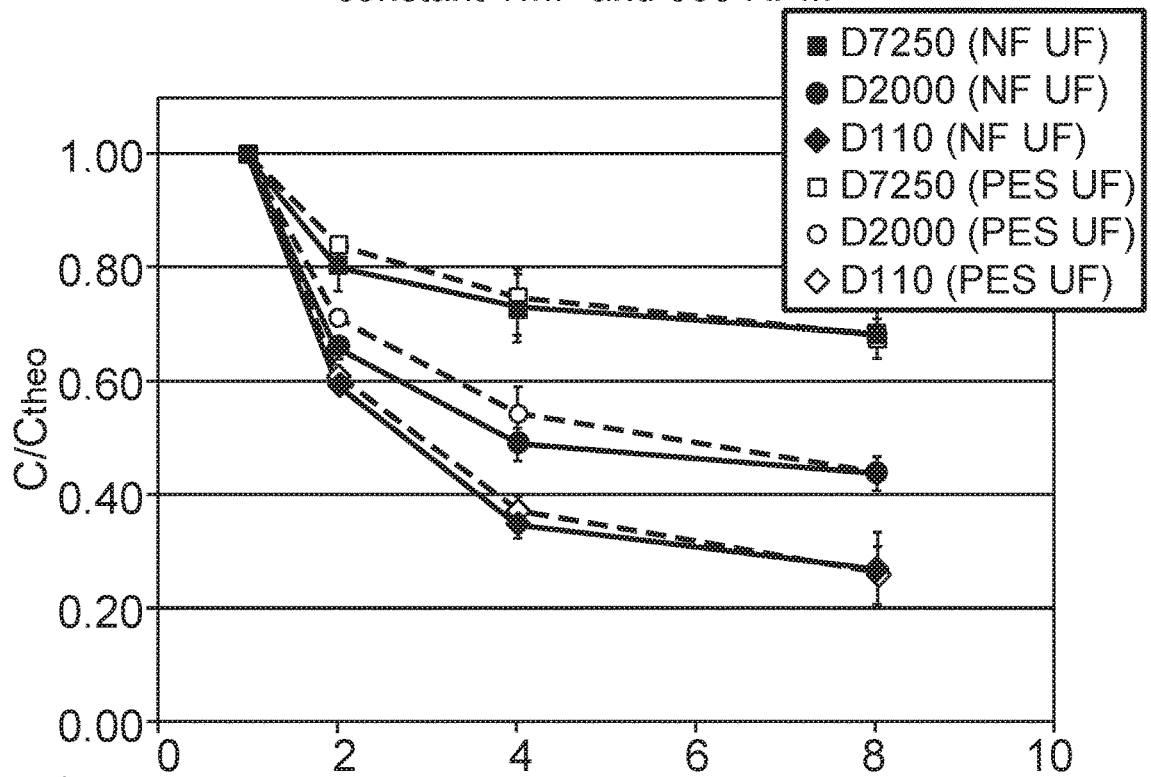
FIG. 26 is a graph depicting the average $C/C_{theo}$ on the y-axis versus concentration factor on the x-axis during 2, 4, and 8× ultrafiltration concentration of Feed A for the NF UF and the PES UF membranes at 0.5 psi constant TMP and 600 RPM in Example 9. Permeate volume over time determines the flux and tracks concentration factors.
Figure 27:
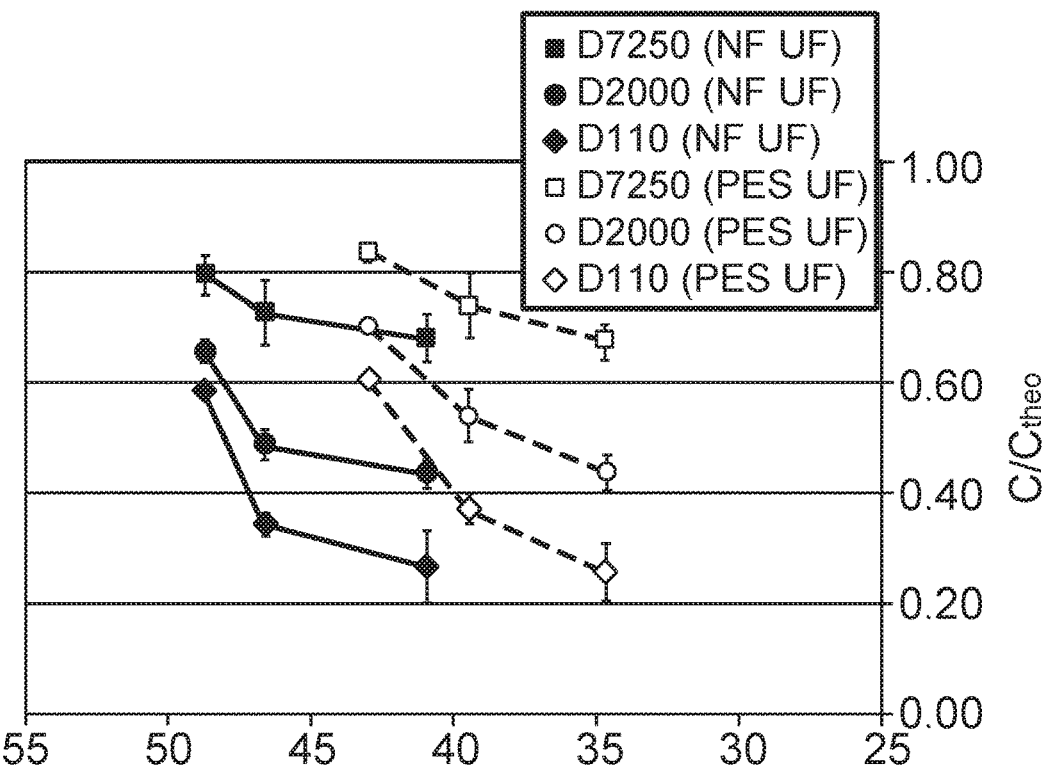
FIG. 27 is a graph depicting the average $C/C_{theo}$ on the y-axis versus average feed flux in LMH on the x-axis during 2, 4, and 8× (Left to Right) ultrafiltration concentration of Feed A for the NF UF and the PES UF membranes at 0.5 psi constant TMP and 600 RPM in Example 9. Permeate volume over time determines the flux and tracks concentration factors. Retentate samples are taken at each concentration factor for GPC analysis to determine yield and selectivity of D7250, D2000, and D110 as described in Example 4. The flux units are Liters of Feed A per square meter of membrane times hours (LMH) on the y-axis.
Figure 28:
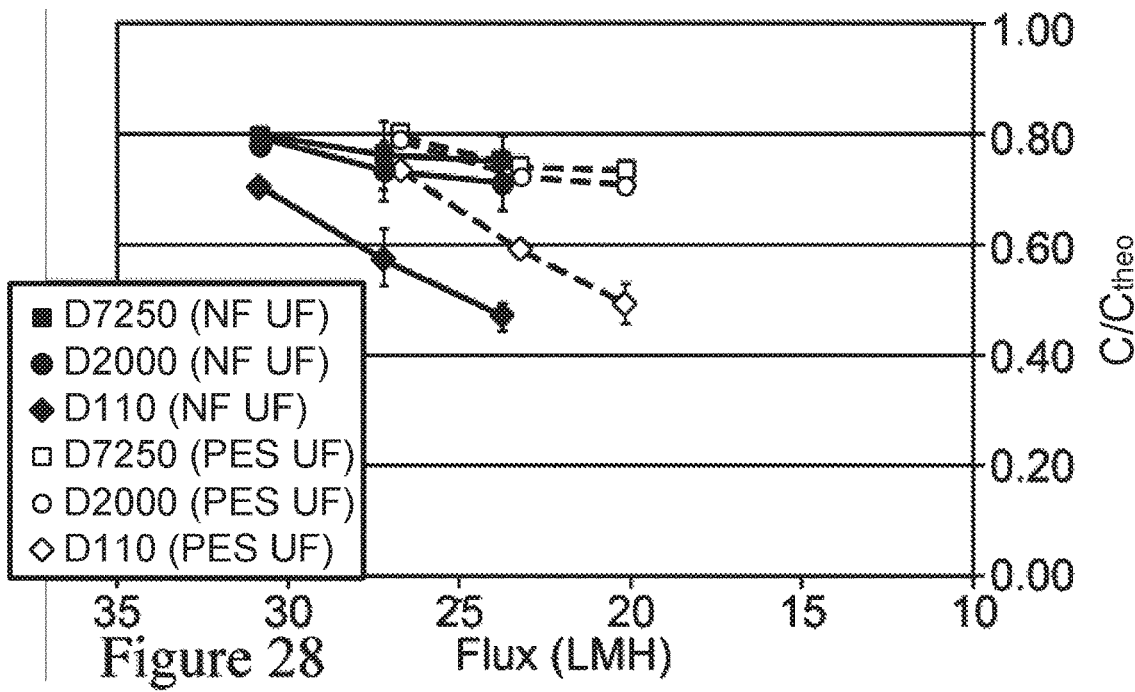
FIG. 28 is a graph depicting the average $C/C_{theo}$ on the y-axis versus average feed flux in LMH on the x-axis during 2, 4, and 8× (Left to Right) ultrafiltration concentration of Feed B for NF UF and the PES UF membranes at 5 psi constant TMP and 600 RPM in Example 9. Permeate volume over time determines the flux and tracks concentration factors. Retentate samples are taken at each concentration factor for GPC analysis to determine yield and selectivity of D7250, D2000, and D110 as described in Example 4. The flux units are Liters of Feed B per square meter of membrane times hours (LMH) on the y-axis.
Figure 29:
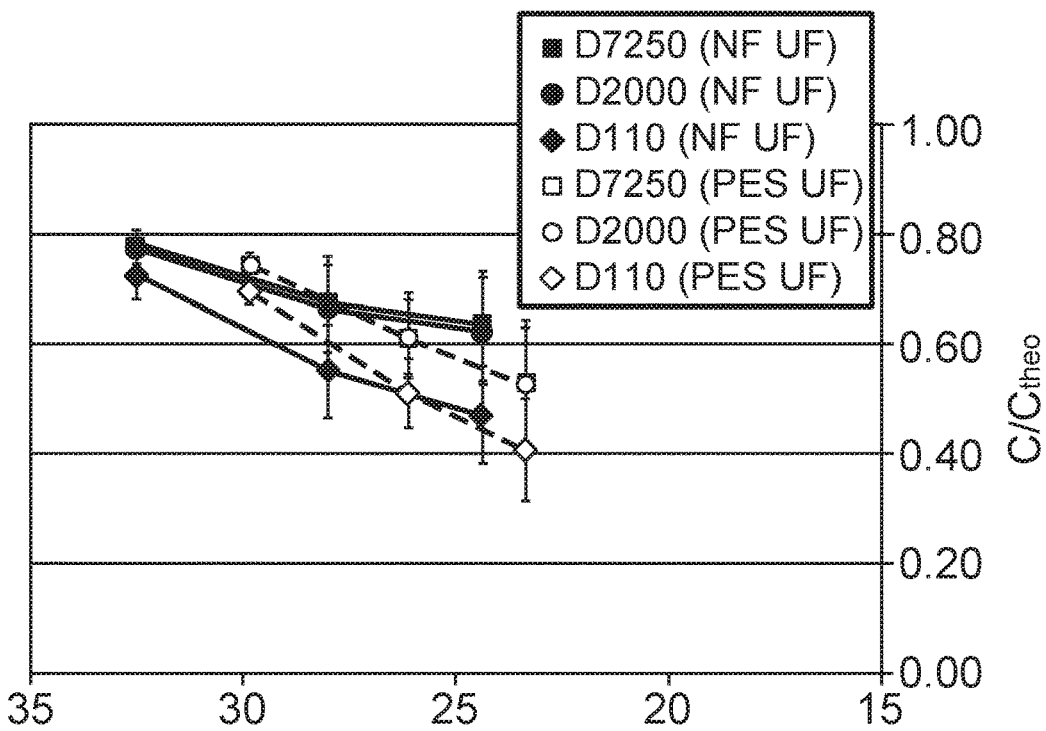
FIG. 29 is a graph depicting the average $C/C_{theo}$ on the y-axis versus average feed flux in LMH on the x-axis during 2, 4, and 8× (Left to Right) ultrafiltration concentration of Feed B for the NF UF and the PES UF membranes at 7 psi constant TMP and 600 RPM in Example 9. Permeate volume over time determines the flux and tracks concentration factors. Retentate samples are taken at each concentration factor for GPC analysis to determine yield and selectivity of D7250, D2000, and D110 as described in Example 4. The flux units are Liters of Feed B per square meter of membrane times hours (LMH) on the y-axis.
Figure 30:
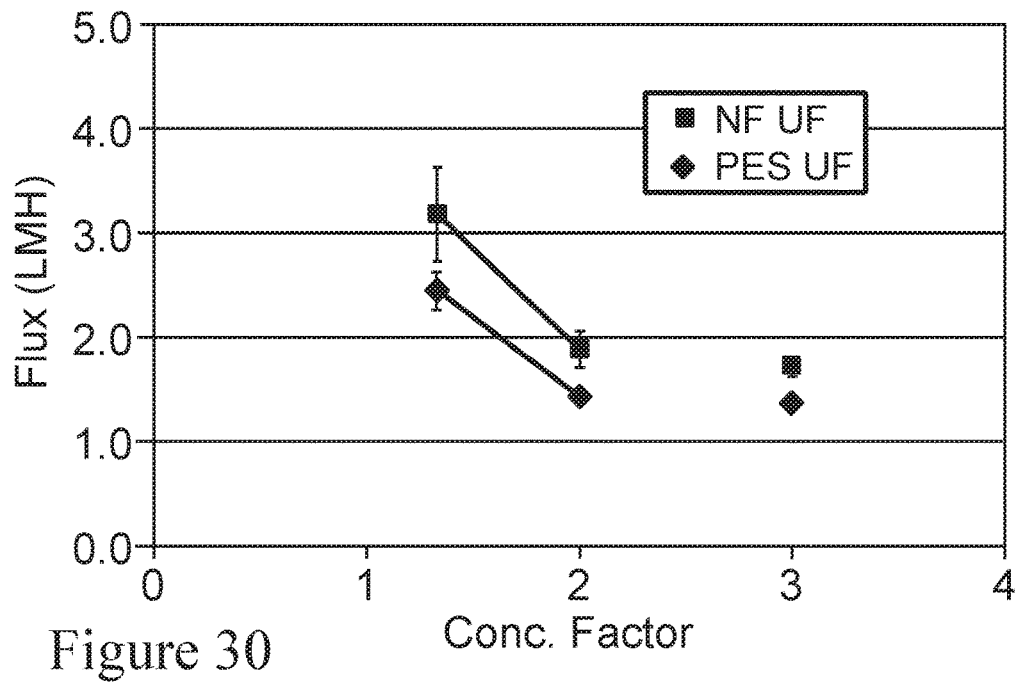
FIG. 30 is a graph depicting the average flux in LMH on the y-axis versus concentration factor on the x-axis during 2 and 3× ultrafiltration concentration of Feed C for the NF UF and the PES UF membranes at 5 psi constant TMP and 300 RPM in Example 9. The flux units are Liters of Feed A per square meter of membrane times hours (LMH) on the y-axis. Permeate volume over time determines the flux and tracks concentration factors.

Five ultrafiltration concentration experiments are conducted in duplicate to compare the NF UF and PES UF membranes at different conditions of constant TMP and stirring using Feeds A, B, and C (summarized in Table 1). Feed A (as shown in FIGS. 25, 26, 27) under 1 condition, Feed B (as shown in FIGS. 28 and 29) under 2 conditions, and Feed C (as shown in FIGS. 30, 31, 32) under 2 conditions.

All five UF concentration runs show that the NF UF and PES UF membranes provide similar average yield and selectivity, while the NF UF membrane has consistently higher average flux over the UF concentration factors for all the feeds and conditions.

Stirred Cells with membrane samples for each condition are prepared in duplicate, as described in Example 3-2. Permeate volume over time is measured in order to determine flux and track concentration factors. Retentate samples are taken at each concentration factor for GPC analysis to determine Yield and Selectivity of D7250, D2000, and D110, as described above.

Feeds A and B with 0.0385 and 0.844% w/w total Dextran mass percent (as set forth in Table 2) are concentrated to 2, 4, and 8× from the initial 50 mL volume. Feed A is concentrated at a constant TMP=0.5 psi and 600 RPM (as shown in FIGS. 25, 26, 27). FIG. 25 shows that NF UF membrane has higher initial average feed flux compared to the PES UF membrane and maintains it throughout the 2, 4 and 8× concentration runs. FIG. 26 shows similar average yield and selectivity for D7250, D2000, and D110 as $C/C_{theo}$ versus concentration factor during 2, 4 and 8× ultrafiltration concentration runs. FIG. 27 shows average $C/C_{theo}$ versus average Flux during the 2, 4, 8× (Left to Right) ultrafiltration concentration where NF UF and PES UF membranes have similar average yield and selectivity, while the NF UF membrane has a consistently higher average flux during the 2, 4 and 8× concentration runs.

Feed B is concentrated at 5 psi and 600 RPM (as shown in FIG. 28) and 7 psi and 600 RPM (as shown in FIG. 29). Better yield and selectivity is observed for both the NF UF and PES NF membranes at the lower pressure (see, FIG. 28 versus 29), but a slightly higher average flux as expected at 7 psi (as shown in FIG. 29).

Feed C with 8.44% w/w total Dextran mass percent (as set forth in Table 2) is concentrated to 2 and 3× from an initial volume of 40 mL. Feed C is concentrated at 5 psi and 300 RPM (as shown in FIGS. 30 and 31) and at 7 psi and 300 RPM (as shown in FIG. 32). In case of Feed C, after 2× concentration, the pressure is increased to 12 psi and it is observed in all cases that the flux and yield decrease for the NF UF and PES UF membranes. FIG. 30 shows the flux decrease for both the NF UF and PES UF membranes at 5 psi. Yields and selectivities are similar for the NF UF and PES UF membranes, while the NF UF membrane has a consistently higher average flux during the 2 and 3× concentration runs (as shown in FIGS. 31 and 32).

Example 10: TFF System for the Purification of a Biological Material Using NF UF Membrane In a representative example, the NF UF membrane is used in a TFF mode to purify a biological material of interest having a molecular weight greater than 500 KDa. Examples of such biological materials include, but are not limited to, conjugated polysaccharide vaccine, other types of vaccines, virus like particles, and proteins with MW>500,000 Daltons.

Figure 33:
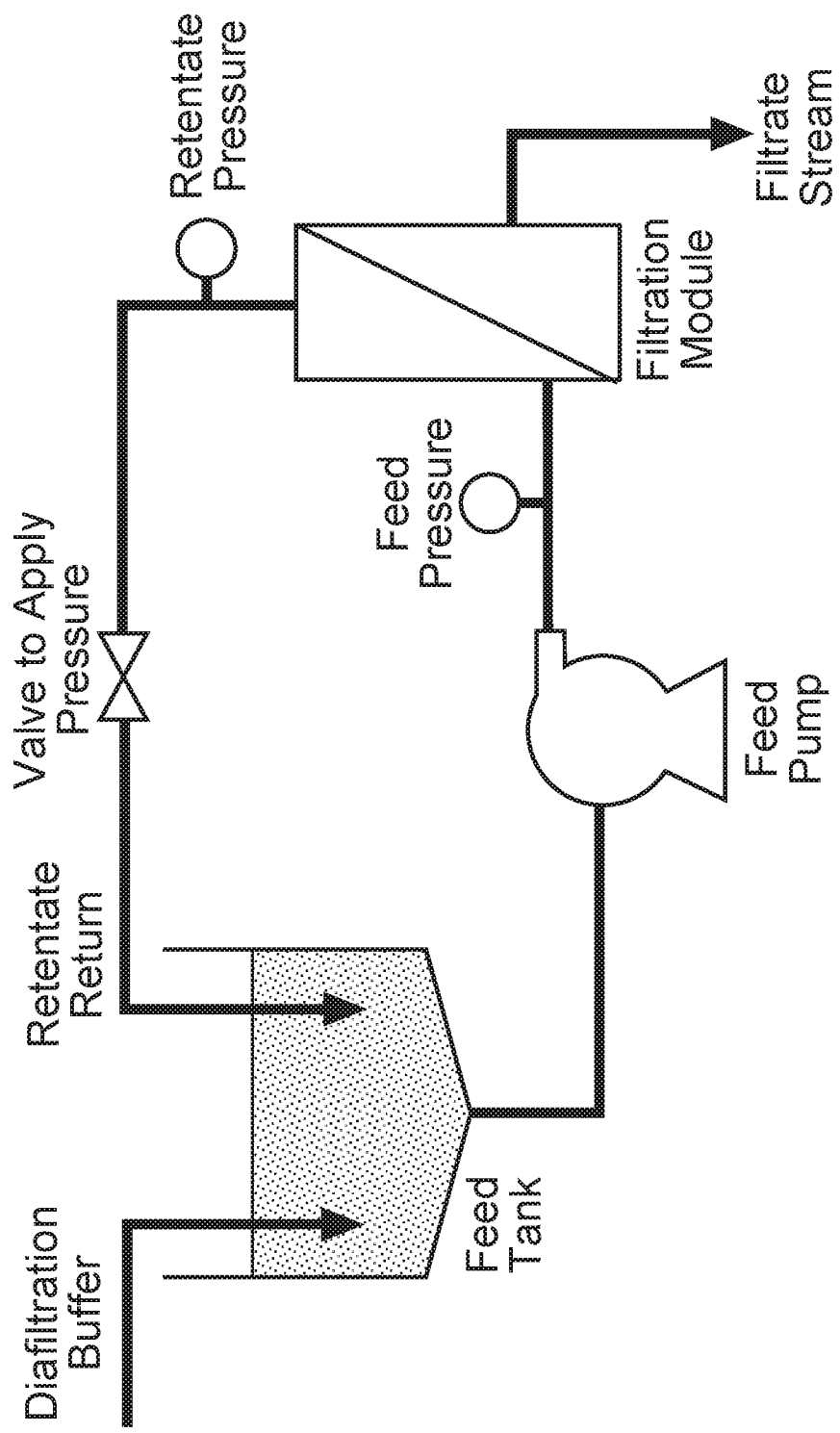
FIG. 33 is a schematic of a TFF system or unit operation employing the NF UF membrane, useful for the purification of a biological material of interest.

A schematic of a TFF system used for the purification of a biological material of interest using the NF UF membrane is shown in FIG. 33. The biological material of interest is present in a feed hold tank or vessel. The typical equipment used are additional buffer tanks or vessels, feed pump, feed valve, feed pressure gauge, TFF modules containing the NF UF membrane such as flat plate cassettes with holders or spiral wound devices with fittings, retentate pressure gauge, retentate valve to control pressure, and permeate vessels. If the feed is being concentrated by ultrafiltration the retentate is returned to the feed tank, if diafiltration is being performed a separate vessel collects the retentate and a diafiltration buffer vessel is plumbed into the feed pump.

The specification is most thoroughly understood in light of the teachings of the references cited within the specification which are hereby incorporated by reference. The embodiments within the specification provide an illustration of embodiments and should not be construed as limiting in scope. The skilled artisan (practitioner) readily recognizes that many other embodiments are encompassed by this disclosure. All publications and reference materials are incorporated by reference in their entirety. To the extent that the material incorporated by reference contradicts or is inconsistent with the present specification, the present specification will supercede any such material. The citation of any references herein is not an admission that such references are prior art.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the embodiments disclosed herein. Unless otherwise indicated, the term "at least" preceding a series of elements is to be understood to refer to every element in the series. Those skilled in the art will recognize, or be able to ascertain using no more than routine experimentation, many equivalents to the specific embodiments described herein. Such equivalents are intended to be encompassed by the following claims.

Many modifications and variations of the embodiments disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the disclosure being indicated by the following claims.

What is claimed is:

1. Method of purifying a biological material of interest in a sample comprising:
   a. providing a sample containing the biological material of interest having a molecular weight equal to or greater than 500 K Da, wherein the biological material of interest is selected from a therapeutic protein, a conjugated polysaccharide vaccine and a virus-like particle;
   b. contacting the sample in tangential filtration (TFF) mode with an electrospun nanofiber membrane composition comprising nylon nanofibers having an average fiber diameter less than 15 nm, thereby resulting in a permeate and a retentate; and
   c. collecting the retentate containing the biological material of interest, thereby purifying the biological material of interest.

2. The method of claim 1, wherein the method results in an increase in the concentration of the biological material of interest.

3. The method of claim 1, wherein the electrospun nanofiber composition exhibits a higher water permeability in TFF mode compared to a solution cast polymeric membrane.

4. The method of claim 1, wherein the electrospun nanofiber membrane composition exhibits a higher flux in TFF mode compared to a solution cast polymeric membrane.

5. The method of claim 1, wherein the collecting step comprises diafiltration.

6. The method of claim 1, wherein the electrospun nanofiber membrane composition is made from Nylon-6.

7. The method of claim 1, wherein the purified biological material of interest has a 90% yield or greater than 90% yield.

8. The method of claim 1, wherein the electrospun nanofiber membrane composition is incorporated into a device suitable for TFF.

9. The method of claim 8, wherein the device is a cassette or a spiral wound device.

* * * * *